US007101886B2

(12) United States Patent
Cho et al.

(10) Patent No.: US 7,101,886 B2
(45) Date of Patent: Sep. 5, 2006

(54) PHENYLALKYL AND PYRIDYLALKYL PIPERAZINE DERIVATIVES

(75) Inventors: Stephen Sung Yong Cho, Northville, MI (US); Jamie Marie Singer, Ann Arbor, MI (US); James M. Graham, Ann Arbor, MI (US); Tracy Fay Gregory, Parma, MI (US); Harry Ralph Howard, Jr., Bristol, CT (US); Sham Shridhar Nikam, Ann Arbor, MI (US); Michael Anthony Walters, Ann Arbor, MI (US)

(73) Assignee: Warner Lambert Company, Morris Plains, NJ (US)

( * ) Notice: Subject to any disclaimer, the term of this patent is extended or adjusted under 35 U.S.C. 154(b) by 272 days.

(21) Appl. No.: 10/703,333

(22) Filed: Nov. 7, 2003

(65) Prior Publication Data

US 2004/0186108 A1 Sep. 23, 2004

Related U.S. Application Data

(60) Provisional application No. 60/425,219, filed on Nov. 8, 2002.

(51) Int. Cl.
*A61K 31/496* (2006.01)
*C07D 417/04* (2006.01)
*C07D 417/14* (2006.01)

(52) U.S. Cl. .............. 514/253.1; 514/249; 514/252.11; 514/253.06; 514/254.04; 544/355; 544/357; 544/363; 544/364; 544/368

(58) Field of Classification Search ................ 544/364, 544/368; 514/253.1, 254.04
See application file for complete search history.

(56) References Cited

U.S. PATENT DOCUMENTS

| | | | | | |
|---|---|---|---|---|---|
| 4,411,901 | A | * | 10/1983 | Temple et al. | 514/253.1 |
| 5,173,490 | A | * | 12/1992 | Peglion et al. | 514/254.04 |
| 5,350,747 | A | * | 9/1994 | Howard | 514/212.07 |
| 6,127,357 | A | * | 10/2000 | Cliffe et al. | 514/210.2 |
| 2004/0067960 | A1 | * | 4/2004 | Davis et al. | 514/253.05 |
| 2004/0138230 | A1 | * | 7/2004 | Andreana et al. | 514/253.07 |

FOREIGN PATENT DOCUMENTS

| | | | |
|---|---|---|---|
| EP | 402644 A | * | 12/1990 |
| EP | 1029861 | * | 8/2000 |
| WO | WO 93/04684 | * | 3/1993 |

* cited by examiner

*Primary Examiner*—Emily Bernhardt
(74) *Attorney, Agent, or Firm*—Karen DeBenedictis; Suzanne M. Harvey; Charles W. Ashbrook

(57) ABSTRACT

This invention relates to compounds of the formula 1

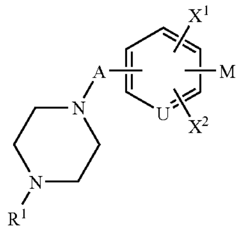

1 wherein $R^1$, $R^3$, $R^4$, $X^1$, and $X^2$ are defined as in the specification, pharmaceutical compositions containing them and their use in the treatment of central nervous system and other disorders.

14 Claims, No Drawings

PHENYLALKYL AND PYRIDYLALKYL PIPERAZINE DERIVATIVES

This application claims priority from U.S. Provisional Application No. 60/425,219 filed Nov. 8, 2002; the entire contents of which are hereby incorporated herein by reference.

BACKGROUND OF THE INVENTION

This invention relates to heterocyclic substituted piperazines, pharmaceutical compositions containing them and their use for the treatment of schizophrenia and other central nervous system (CNS) disorders.

The heterocyclic substituted piperazine derivatives of this invention exhibit activity as antagonists of dopamine D2 receptors and of serotonin 2A (5HT2A) receptors.

Other heterocyclic piperazine derivatives that are useful for the treatment of schizophrenia are referred to in U.S. Pat. No. 5,350,747, which issued on Sep. 27, 1994, and in U.S. Pat. No. 6,127,357, which issued on Oct. 3, 2000. These patents are incorporated herein by reference in their entirety.

Other piperazine and piperidine derivatives that have been stated to be useful as antipsychotic agents are those referred to in PCT patent publication WO 93/04684, which published on Mar. 18, 1993, and European patent application EP 402644A, which was published on Dec. 19, 1990. These patent applications are incorporated herein by reference in their entirety.

SUMMARY OF THE INVENTION

The present invention relates to compounds of the formula 1

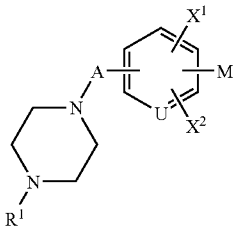

1 wherein M is (i)

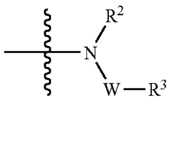

or

-continued (ii)

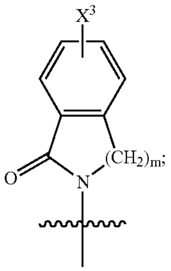

$R^1$ is 1,2-benzisothiazoyl, 1,2-benzisothiazoyl-1-oxide, 1,2-benzisothiazoyl-1-dioxide, 1,2-benzisoxazoyl, naphthyl, pyridyl, quinolyl, isoquinolyl benzothiadiazolyl, benzotriazolyl, benzoxazolyl, benzoxazolonyl, indolyl, indanyl, 1H-indazoyl, or 3-indazolyl, and wherein said $R^1$ can optionally be substituted by one or more substituents, preferably from zero to four substituents, independently selected from halo, preferably chloro or fluoro, cyano, nitro, $(C_1-C_6)$alkyl optionally substituted with from one to three fluorine atoms and $(C_1-C_6)$alkoxy optionally substituted with from one to three fluorine atoms, and wherein the point of attachment of $R^1$ to the piperazine nitrogen of formula 1 is a carbon atom of the heterocyclic ring of $R^1$;

A is $-(CH_2)_nCH_2-$, wherein n is an integer from one to three;

U is carbon or nitrogen;

m is 1 or 2;

each of $X^1$, $X^2$ and $X^3$ is, independently, hydrogen, halo, $(C_1-C_6)$alkyl optionally substituted with from one to three fluorine atoms and $(C_1-C_6)$alkoxy optionally substituted with from one to three fluorine atoms;

$R^2$ is hydrogen, $(C_1-C_6)$alkyl, aryl$(C_1-C_6)$alkyl, $(C_1-C_6)$alkenyl, heteroaryl, or heteroaryl$(C_1-C_6)$alkyl, and where the aryl and heteroaryl moieties of the foregoing $R^2$ groups may be optionally substituted with one or two substituents independently selected from halo, $(C_1-C_6)$alkyl optionally substituted with from one to three fluorine atoms and $(C_1-C_6)$alkoxy optionally substituted with from one to three fluorine atoms;

W is $-C(O)-$, $-C(O)O-$, $-C(O)NH-$, $-S(O)_2-$, or $-S(O_2)N(R^4)-$, wherein the hyphen to the left of each of the foregoing moieties represents the bond to $NR^2$ in structural formula 1, and the hyphen to the right of each of the foregoing moieties represents the bond to $R^3$ in structural formula 1; and $R^3$ and $R^4$ are selected, independently, from $(C_1-C_6)$alkyl, aryl$(C_1-C_6)$alkyl, $(C_1-C_6)$alkenyl, heteroaryl, and heteroaryl$(C_1-C_6)$alkyl, wherein the aryl and heteroaryl moieties of the foregoing $R^3$ and $R^4$ groups can be optionally be substituted with one or two substituents independently selected from halo, $(C_1-C_6)$alkyl optionally substituted with from one to three fluorine atoms and $(C_1-C_6)$alkoxy optionally substituted with from one to three fluorine atoms;

and the pharmaceutically acceptable salts of such compounds.

Preferred compounds of the invention include compounds of the formula 1 wherein $R^2$ is hydrogen, methyl or ethyl.

Other preferred compounds of the invention include compounds of the formula 1 wherein $X^1$ and $X^2$ is hydrogen.

Other preferred compounds of the invention include compounds of the formula 1 wherein W is —CO— and $R^3$ is $(C_1–C_3)$alkyl.

Other embodiments of this invention include compounds of the formula 1 wherein U is carbon.

Other embodiments of this invention include compounds of the formula 1 wherein U is nitrogen.

Examples of specific preferred embodiments of this invention include the following compounds and their pharmaceutically acceptable salts:

N-{2-[2-(4-1,2-Benzisothiazol-3-yl-piperazin-1-yl)-ethyl]-phenyl}-2-(2,5-dimethoxy-phenyl)-acetamide;

N-{4-[2-(4-1,2-Benzisothiazol-3-yl-piperazin-1-yl)-ethyl]-5-chloro-2-methyl-phenyl}-acetamide;

1-{3-[2-(4-1,2-Benzisothiazol-3-yl-piperazin-1-yl)-ethyl]-phenyl}-3-p-tolyl-urea;

N-{4-[2-(4-1,2-Benzisothiazol-3-yl-piperazin-1-yl)-ethyl]-2-methyl-phenyl}-acetamide;

1-{2-[2-(4-1,2-Benzisothiazol-3-yl-piperazin-1-yl)-ethyl]-phenyl}-3-o-tolyl-urea;

1-{4-[2-(4-1,2-Benzisothiazol-3-yl-piperazin-1-yl)-ethyl]-phenyl}-3-cyclopentyl-urea;

N-{2-[2-(4-1,2-Benzisothiazol-3-yl-piperazin-1-yl)-ethyl]-phenyl}-2-(3-methoxy-phenyl)-acetamide;

N-{2-[2-(4-1,2-Benzisothiazol-3-yl-piperazin-1-yl)-ethyl]-phenyl}-2-fluoro-benzenesulfonamide;

1,2-Dimethyl-1H-imidazole-4-sulfonic acid {2-[2-(4-1,2-benzisothiazol-3-yl-piperazin-1-yl)-ethyl]-phenyl}-amide;

N-{4-[2-(4-1,2-Benzisothiazol-3-yl-piperazin-1-yl)-ethyl]-phenyl}-benzenesulfonamide;

N-{4-[2-(4-1,2-Benzisothiazol-3-yl-piperazin-1-yl)-ethyl]-5-chloro-2-methyl-phenyl}-N-methyl-acetamide;

N-{4-[2-(4-1,2-Benzisothiazol-3-yl-piperazin-1-yl)-ethyl]-2,5-dimethyl-phenyl}-acetamide;

N-{4-[2-(4-1,2-Benzisothiazol-3-yl-piperazin-1-yl)-ethyl]-2-methyl-phenyl}-N-methyl-acetamide;

N-{4-[2-(4-1,2-Benzisothiazol-3-yl-piperazin-1-yl)-ethyl]-2-methyl-phenyl}-N-ethyl-acetamide;

N-{4-[3-(4-1,2-Benzisothiazol-3-yl-piperazin-1-yl)-propyl]-phenyl}-2-thiophen-2-yl-acetamide;

N-{2-[2-(4-1,2-Benzisothiazol-3-yl-piperazin-1-yl)-ethyl]-phenyl}-2-benzyloxy-acetamide;

N-{2-[2-(4-1,2-Benzisothiazol-3-yl-piperazin-1-yl)-ethyl]-phenyl}-2-(4-methoxy-phenyl)-acetamide;

N-{4-[2-(4-1,2-Benzisothiazol-3-yl-piperazin-1-yl)-ethyl]-phenyl}-2,5-dimethoxy-benzenesulfonamide;

N-{2-[2-(4-1,2-Benzisothiazol-3-yl-piperazin-1-yl)-ethyl]-phenyl}-2-(4-chloro-phenyl)-acetamide;

N-{2-[2-(4-1,2-Benzisothiazol-3-yl-piperazin-1-yl)-ethyl]-4,5-dimethoxy-phenyl}-2-(4-chloro-phenyl)-acetamide;

1-{3-[2-(4-1,2-Benzisothiazol-3-yl-piperazin-1-yl)-ethyl]-phenyl}-3-benzyl-urea; and N-{2-[2-(4-Benzo[d]isothiazol-3-yl-piperazin-1-yl-ethyl]-6-methyl-pyridin-3-yl}-2-(4-chloro-phenyl)-acetamide.

Other embodiments of this invention include the following compounds and their pharmaceutically acceptable salts:

N-{6-[2-(4-Benzo[d]isoxazol-3-yl-piperazin-1-yl)-ethyl]-4-methyl-pyridin-3-yl}-acetamide;

N-(6-{2-[4-(1H-Indazol-3-yl)-piperazin-1-yl]-ethyl}-4-methyl-pyridin-3-yl)-acetamide;

N-(6-{2-[4-(6-Fluoro-benzo[d]isoxazol-3-yl)-piperazin-1-yl]-ethyl}-4-methyl-pyridin-3-yl)-acetamide;

N-{6-[2-(4-Benzo[d]isoxazol-3-yl-piperazin-1-yl)-ethyl]-2-methyl-pyridin-3-yl}-acetamide;

N-(6-{2-[4-(1H-indazol-3-yl)-piperazin-1-yl]-ethyl}-2-methyl-pyridin-3-yl)-acetamide;

N-(6-{2-[4-(6-Fluoro-benzo[d]isoxazol-3-yl)-piperazin-1-yl]-ethyl}-2-methyl-pyridin-3-yl)-acetamide;

N-{6-[2-(4-Benzo[d]isoxazol-3-yl-piperazin-1-yl)-ethyl]-4-methyl-pyridin-3-yl}-acetamide;

N-{6-[2-(4-Benzo[d]isoxazol-3-yl-piperazin-1-yl)-ethyl]-2-methyl-pyridin-3-yl)-acetamide;

N-(6-{2-[4-(1H-Indazol-3-yl)-piperazin-1-yl]-ethyl}-4-methyl-pyridin-3-yl)-acetamide;

N-(6-{2-[4-(1H-Indazol-3-yl)-piperazin-1-yl]-ethyl}-2-methyl-pyridin-3-yl)-acetamide;

N-(6-{2-[4-(6-Fluoro-benzo[d]isoxazol-3-yl)-piperazin-1-yl]-ethyl}-4-methyl-pyridin-3-yl)-acetamide;

N-(6-{2-[4-(6-Fluoro-benzo[d]isoxazol-3-yl)-piperazin-1-yl]-ethyl}-2-methyl-pyridin-3-yl)-acetamide;

N-{6-[3-(4-Benzo[d]isothiazol-3-yl-piperazin-1-yl)-propyl]-4-methyl-pyridin-3-yl}-acetamide;

N-(6-{3-[4-(1H-Indazol-3-yl)-piperazin-1-yl]-propyl}-4-methyl-pyridin-3-yl)-acetamide;

N-{6-[3-(4-Benzo[d]isoxazol-3-yl-piperazin-1-yl)-propyl]-4-methyl-pyridin-3-yl}-acetamide;

N-(6-{3-[4-(6-Fluoro-benzo[d]isoxazol-3-yl)-piperazin-1-yl]-propyl}-4-methyl-pyridin-3-yl)-acetamide;

N-{6-[3-(4-Benzo[d]isothiazol-3-yl-piperazin-1-yl)-propyl]-2-methyl-pyridin-3-yl}-acetamide;

N-{6-[3-(4-Benzo[d]isothiazol-3-yl-piperazin-1-yl)-propyl]-2-methyl-pyridin-3-yl}-acetamide;

N-{6-[3-(4-Benzo[d]isoxazol-3-yl-piperazin-1-yl)-propyl]-2-methyl-pyridin-3-yl}-acetamide;

N-(6-{3-[4-(6-Fluoro-benzo[d]isoxazol-3-yl)-piperazin-1-yl]-propyl}-2-methyl-pyridin-3-yl)-acetamide;

N-{6-[3-(4-Benzo[d]isoxazol-3-yl-piperazin-1-yl)-propyl]-4-methyl-pyridin-3-yl}-acetamide;

N-{6-[3-(4-Benzo[d]isoxazol-3-yl-piperazin-1-yl)-propyl]-2-methyl-pyridin-3-yl}-acetamide;

N-(6-{3-[4-(1H-Indazol-3-yl)-piperazin-1-yl]-propyl}-4-methyl-pyridin-3-yl)-acetamide;

N-(6-{3-[4-(1H-Indazol-3-yl)-piperazin-1-yl]-propyl}-2-methyl-pyridin-3-yl}-acetamide;

N-{6-[3-(4-Benzo[d]isoxazol-3-yl-piperazin-1-yl)-propyl]-4-methyl-pyridin-3-yl}-acetamide;

N-{6-[3-(4-Benzo[d]isoxazol-3-yl-piperazin-1-yl)-propyl]-2-methyl-pyridin-3-yl}-acetamide;

N-(6-{3-[4-(6-Fluoro-benzo[d]isoxazol-3-yl)-piperazin-1-yl]-propyl}-4-methyl-pyridin-3-yl)-acetamide; and N-(6-{3-[4-(6-Fluoro-benzo[d]isoxazol-3-yl)-piperazin-1-yl]-propyl}-2-methyl-pyridin-3-yl)-acetamide.

The term "aryl", as used herein, unless otherwise indicated, includes an aromatic ring system with no heteroatoms (e.g., phenyl or naphthyl).

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like.

The term "alkoxy", as used herein, unless otherwise indicated, means "alkyl-O-", wherein "alkyl" is as defined above. Examples of "alkoxy" groups include, but are not limited to, methoxy, ethoxy, propoxy, butoxy and pentoxy.

The term "alkenyl", as used herein, unless otherwise indicated, includes unsaturated hydrocarbon radicals having one or more double bonds connecting two carbon atoms, wherein said hydrocarbon radical may have straight, branched or cyclic moieties or combinations thereof.

Examples of "alkenyl" groups include, but are not limited to, ethenyl, propenyl, butenyl, pentenyl.

The term "heteroaryl", as used herein, unless otherwise indicated, includes monocyclic aromatic heterocycles containing five or six ring members, of which from 1 to 4 can be heteroatoms selected, independently, from N, S and O, and bicyclic aromatic heterocycles containing from eight to twelve ring members, of which from 1 to 4 can be heteroatoms selected, independently, from N, S and O.

The term "one or more substituents", as used herein, refers to a number of substituents that equals from one to the maximum number of substituents possible based on the number of available bonding sites.

The terms "halo" and "halogen", as used herein, unless otherwise indicated, include, fluoro, chloro, bromo and iodo.

The term "treating", as used herein, refers to reversing, alleviating, inhibiting the progress of, or preventing the disorder or condition to which such term applies, or preventing one or more symptoms of such condition or disorder.

The term "treatment", as used herein, refers to the act of treating, as "treating" is defined immediately above.

The term "methylene", as used herein, means $—CH_2—$.

The term "ethylene", as used herein, means $—CH_2CH_2—$.

The term "propylene", as used herein, means $—CH_2CH_2CH_2—$.

The compounds of formula 1 and their pharmaceutically acceptable salts are also referred to herein, collectively, as the "novel compounds of this invention" and the "active compounds of this invention".

This invention also relates to a pharmaceutical composition comprising a therapeutically effective amount of a compound of the formula 1, or a pharmaceutically acceptable salt thereof, and a pharmaceutically acceptable carrier.

Compounds of formula 1 may contain chiral centers and therefore may exist in different enantiomeric and diastereomeric forms. This invention relates to all optical isomers and all stereoisomers of compounds of the formula 1, both as racemic mixtures and as individual enantiomers and diastereoisomers of such compounds, and mixtures thereof, and to all pharmaceutical compositions and methods of treatment defined above that contain or employ them, respectively. Individual isomers can be obtained by known methods, such as optical resolution, optically selective reaction, or chromatographic separation in the preparation of the final product or its intermediate. Individual enantiomers of the compounds of formula 1 may have advantages, as compared with the racemic mixtures of these compounds, in the treatment of various disorders or conditions.

In so far as the compounds of formula 1 of this invention are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts.

The present invention also includes isotopically labelled compounds, which are identical to those recited in formula 1, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples below, by substituting a readily available isotopically labelled reagent for a non-isotopically labelled reagent.

The compounds of formula 1 of this invention have useful pharmaceutical and medicinal properties.

This invention also relates to a method of treating a disorder or condition selected from the group consisting of single episodic or recurrent major depressive disorders, dysthymic disorders, depressive neurosis and neurotic depression, melancholic depression including anorexia, weight loss, insomnia, early morning waking or psychomotor retardation; a typical depression (or reactive depression) including increased appetite, hypersomnia, psychomotor agitation or irritability, seasonal affective disorder and pediatric depression; bipolar disorders or manic depression, for example, bipolar I disorder, bipolar II disorder and cyclothymic disorder; conduct disorder; disruptive behavior disorder; behavioral disturbances associated with mental retardation, autistic disorder, and conduct disorder; anxiety disorders such as panic disorder with or without agoraphobia, agoraphobia without history of panic disorder, specific phobias, for example, specific animal phobias, social anxiety, social phobia, obsessive-compulsive disorder, stress disorders including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia; delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple aetiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; chemical dependencies and addictions (e.g., dependencies on, or addictions to, alcohol, heroin, cocaine, benzodiazepines, nicotine, or phenobarbitol) and behavioral addictions such as an addiction to gambling; and ocular disorders such as glaucoma and ischemic retinopathy in a mammal, including a human, comprising administering to a mammal in need of such treatment an amount of a compound of the formula 1, or a pharmaceutically acceptable salt thereof, that is effective in treating such disorder or condition.

The compounds of formula 1 and their pharmaceutically acceptable salts are also referred to herein, collectively, as the "novel compounds of this invention" and the "active compounds of this invention".

This invention also relates to a pharmaceutical composition comprising a therapeutically effective amount of a compound of the formula 1, or a pharmaceutically acceptable salt thereof, and a pharmaceutically acceptable carrier.

This invention also relates to a pharmaceutical composition for treating a disorder or condition selected from single episodic or recurrent major depressive disorders, dysthymic disorders, depressive neurosis and neurotic depression, melancholic depression including anorexia, weight loss, insomnia, early morning waking or psychomotor retardation; a typical depression (or reactive depression) including increased appetite, hypersomnia, psychomotor agitation or irritability, seasonal affective disorder and pediatric depression; bipolar disorders or manic depression, for example, bipolar I disorder, bipolar II disorder and cyclothymic disorder; conduct disorder; disruptive behavior behavioral disturbances associated with mental retardation, autistic disorder, and conduct disorder; anxiety disorders such as panic disorder with or without agoraphobia, agoraphobia without history of panic disorder, specific phobias, for example, specific animal phobias, social anxiety, social phobia, obsessive-compulsive disorder, stress disorders including post-traumatic stress disorder and acute stress disorder, and generalized anxiety disorders; borderline personality disorder; schizophrenia and other psychotic disorders, for example, schizophreniform disorders, schizoaffective disorders, delusional disorders brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia; delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple aetiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; chemical dependencies and addictions (e.g., dependencies on, or addictions to, alcohol, heroin, cocaine, benzodiazepines, nicotine, or phenobarbitol) and behavioral addictions such as an addiction to gambling; and ocular disorders such as glaucoma and ischemic retinopathy in a mammal in need of such treatment, including a human, comprising an amount of a compound of the formula 1, or a pharmaceutically acceptable salt thereof, that is effective in treating such disorder or condition, and a pharmaceutically acceptable carrier.

A more specific embodiment of this invention relates to the above method wherein the disorder or condition that is being treated is selected from major depression, single episode depression, recurrent depression, child abuse induced depression, postpartum depression, dysthymia, cyclothymia and bipolar disorder.

Another more specific embodiment of this invention relates to the above method wherein the disorder or condition that is being treated is selected from schizophrenia, schizoaffective disorder, delusional disorder, substance-induced psychotic disorder, brief psychotic disorder, shared psychotic disorder, psychotic disorder due to a general medical condition, and schizophreniform disorder.

Another more specific embodiment of this invention relates to the above method wherein the disorder or condition that is being treated is selected from autism, pervasive development disorder, and attention deficit hyperactivity disorder.

Another more specific embodiment of this invention relates to the above method wherein the disorder or condition that is being treated is selected from generalized anxiety disorder, panic disorder, obsessive-compulsive disorder, post-traumatic stress disorder, and phobias, including social phobia, agoraphobia, and specific phobias.

Another more specific embodiment of this invention relates to the above method wherein the disorder or condition that is being treated is selected from movement disorders such as akinesias, dyskinesias, including familial paroxysmal dyskinesias, spasticities, Tourette's syndrome, Scott syndrome, PALSYS and akinetic-rigid syndrome; and extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour.

Another more specific embodiment of this invention relates to the above method wherein the disorder or condition that is being treated is selected from delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple aetiologies.

Another more specific embodiment of this invention relates to the above method wherein the compound of formula 1 is administered to a human for the treatment of any two or more comorbid disorders or conditions selected from those disorders and conditions referred to in any of the above methods.

For the treatment of depression, anxiety, schizophrenia or any of the other disorders and conditions referred to above in the descriptions of the methods and pharmaceutical compositions of this invention, the novel compounds of this invention can be used in conjunction with one or more other antidepressants or anti-anxiety agents. Examples of classes of antidepressants that can be used in combination with the active compounds of this invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and a typical antidepressants. Suitable norepinephrine reuptake inhibitors include tertiary amine tricyclics and secondary amine tricyclics. Suitable tertiary amine tricyclics and secondary amine tricyclics include amitriptyline, clomipramine, doxepin, imipramine, trimipramine, dothiepin, butripyline, iprindole, lofepramine, nortriptyline, protriptyline, amoxapine, desipramine and maprotiline. Suitable selective serotonin reuptake inhibitors include fluoxetine, fluvoxamine, paroxetine and sertraline. Examples of monoamine oxidase inhibitors include isocarboxazid, phenelzine, and tranylcyclopramine. Suitable reversible inhibitors of monoamine oxidase include moclobemide. Suitable serotonin and noradrenaline reuptake inhibitors of use in the present invention include venlafaxine. Suitable CRF antagonists include those compounds described in International Patent Application Nos. WO 94/13643, WO 94/13644, WO 94/13661, WO 94/13676 and WO 94/13677. Suitable a typical anti-depressants include bupropion, lithium, nefazodone, trazodone and viloxazine. Suitable NK-1 receptor antagonists include those referred to in World Patent Publication WO 01/77100.

Suitable classes of anti-anxiety agents that can be used in combination with the active compounds of this invention include benzodiazepines and serotonin IA (5-$HT_{IA}$) agonists or antagonists, especially 5-$HT_{IA}$ partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-$HT_{IA}$ receptor agonists or antagonists include buspirone, flesinoxan, gepirone and ipsapirone.

This invention also relates to a method of treating a disorder or condition selected from single episodic or recurrent major depressive disorders, dysthymic disorders, depressive neurosis and neurotic depression, melancholic depression including anorexia, weight loss, insomnia, early morning waking or psychomotor retardation; a typical depression (or reactive depression) including increased appetite, hypersomnia, psychomotor agitation or irritability, seasonal affective disorder and pediatric depression; bipolar disorders or manic depression, for example, bipolar I disorder, bipolar II disorder and cyclothymic disorder; conduct disorder; disruptive behavior disorder; behavioral disturbances associated with mental retardation, autistic disorder, and conduct disorder; anxiety disorders such as panic disorder with or without agoraphobia, agoraphobia without history of panic disorder, specific phobias, for example, specific animal phobias, social anxiety, social phobia, obsessive-compulsive disorder, stress disorders including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia; delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple aetiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; chemical dependencies and addictions (e.g., dependencies on, or addictions to, alcohol, heroin, cocaine, benzodiazepines, nicotine, or phenobarbitol) and behavioral addictions such as an addiction to gambling; and ocular disorders such as glaucoma and ischemic retinopathy in a mammal in need of such treatment, including a human, comprising administering to said mammal:

(a) a compound of the formula 1 or a pharmaceutically acceptable salt thereof; and (b) another pharmaceutically active compound that is an antidepressant or anti-anxiety agent, or a pharmaceutically acceptable salt thereof;

wherein the active compounds "a" and "b" are present in amounts that render the combination effective in treating such disorder or condition.

A more specific embodiment of this invention relates to the above method wherein the disorder or condition that is being treated is selected from major depression, single episode depression, recurrent depression, child abuse induced depression, postpartum depression, dysthymia, cyclothymia and bipolar disorder.

Another more specific embodiment of this invention relates to the above method wherein the disorder or condition that is being treated is selected from schizophrenia, schizoaffective disorder, delusional disorder, substance-induced psychotic disorder, brief psychotic disorder, shared psychotic disorder, psychotic disorder due to a general medical condition, and schizophreniform disorder.

Another more specific embodiment of this invention relates to the above method wherein the disorder or condition that is being treated is selected from autism, pervasive development disorder, and attention deficit hyperactivity disorder.

Another more specific embodiment of this invention relates to the above method wherein the disorder or condition that is being treated is selected from generalized anxiety disorder, panic disorder, obsessive-compulsive disorder, post-traumatic stress disorder, and phobias, including social phobia, agoraphobia, and specific phobias.

Another more specific embodiment of this invention relates to the above method wherein the disorder or condition that is being treated is selected from movement disorders such as akinesias, dyskinesias, including familial paroxysmal dyskinesias, spasticities, Tourette's syndrome, Scott syndrome, PALSYS and akinetic-rigid syndrome; and extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour.

Another more specific embodiment of this invention relates to the above method wherein the disorder or condition that is being treated is selected from delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple aetiologies.

Another more specific embodiment of this invention relates to the above method wherein the compound of formula 1 and the additional antidepressant or anti-anxiety agent are administered to a human for the treatment of any two or more comorbid disorders or conditions selected from those disorders and conditions referred to in any of the above methods.

This invention also relates to a pharmaceutical composition for treating a disorder or condition selected from single episodic or recurrent major depressive disorders, dysthymic disorders, depressive neurosis and neurotic depression, melancholic depression including anorexia, weight loss, insomnia, early morning waking or psychomotor retardation; a typical depression (or reactive depression) including increased appetite, hypersomnia, psychomotor agitation or irritability, seasonal affective disorder and pediatric depression; bipolar disorders or manic depression, for example, bipolar I disorder, bipolar II disorder and cyclothymic disorder; conduct disorder; disruptive behavior disorder; behavioral disturbances associated with mental retardation, autistic disorder, and conduct disorder; anxiety disorders such as panic disorder with or without agoraphobia, agoraphobia without history of panic disorder, specific phobias, for example, specific animal phobias, social anxiety, social phobia, obsessive-compulsive disorder, stress disorders including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia; delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple aetiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; chemical dependencies and addictions (e.g., dependencies on, or addictions to, alcohol, heroin, cocaine, benzodiazepines, nicotine, or phenobarbitol) and behavioral addictions such as an addiction to gambling; and ocular disorders such as glaucoma and ischemic retinopathy in a mammal in need of such treatment, including a human, comprising:

(a) a compound of the formula 1 or a pharmaceutically acceptable salt thereof;

(b) another pharmaceutically active compound that is an antidepressant or anti-anxiety agent, or a pharmaceutically acceptable salt thereof; and (c) a pharmaceutically acceptable carrier;

wherein the active compounds "a" and "b" are present in amounts that render the composition effective in treating such disorder or condition.

DETAILED DESCRIPTION OF THE INVENTION

The compounds of formula 1 of the present invention may be prepared as described in the following reaction schemes. Unless otherwise indicated, in the reaction schemes and discussion that follow, $R^1$ through $R^3$, n, m, W, U, A, $X^1$, $X^2$ and $X^3$ are defined as above.

Scheme A

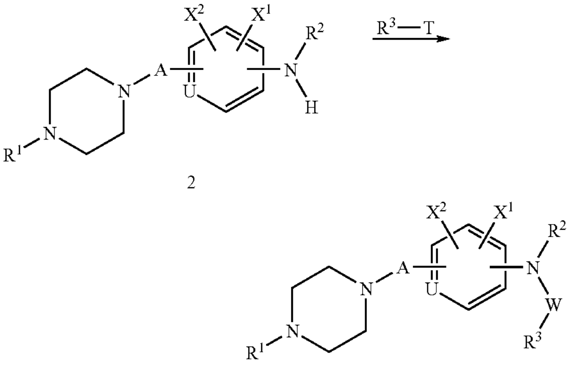

2

1

Scheme A illustrates a method for preparing compounds of the formula 1 by reaction of compound of the formula 2 with a compound of the formula $R^3$-T wherein T is —COCl, an acid or a suitably activated acid derivative such as the mixed anhydride, —OCOCl, —N=C=O, or —$SO_2Cl$, or $R^3$-T is $ClSO_2N(Me)_2$ or $ClSO_2R^3R^4$. The reaction above may be carried out in an inert solvent such as methylene chloride, dichloroethane, benzene, toluene, or pyridine, preferably methylene chloride. This reaction is typically carried out at a temperature from about −78° C. to about the reflux temperature of the solvent, preferably from about 0° C. to about 25° C., for a period of about 5 minutes to 48 hours, preferably from 0.5 to 16 hours. The reaction is typically performed in the presence of organic base such as diisopropylethylamine, or pyridine, or triethylamine, preferably triethylamine, or in the presence of a polymer supported base such as tris-(2-aminoethyl)amine polystyrene.

Scheme B

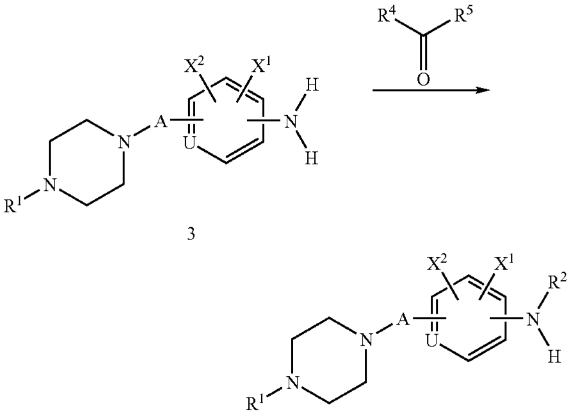

3

2

Scheme B illustrates a method for preparing compounds of the formula 2 by the reductive amination of compounds of the formula 3 with compounds of the formula $R^5R^6C{=}O$, wherein $R^5$ and $R^6$ are independently selected from hydrogen, $(C_1$–$C_3)$alkyl, aryl, aryl$(C_1$–$C_6)$alkyl, $(C_1$–$C_3)$alkenyl, heteroaryl, and heteroaryl$(C_1$–$C_6)$alkyl, wherein the aryl and heteroaryl moieties of the foregoing $R^5$ and $R^6$ groups can be optionally substituted with one or two substituents that are independently selected from halo, $(C_1$–$C_6$ alkyl) optionally substituted with from one to three fluorine atoms and $(C_1$–$C_6$ alkoxy) optionally substituted with from one to three fluorine atoms.

The above reaction may be carried in one vessel without isolation of the imine intermediate, or $R^5R^6C{=}O$ and the compound of formula 3 may be combined in an inert solvent such as methylene chloride, dichloroethane, toluene or benzene, either at about room temperature or at about the reflux temperature of the solvent, with or without removal of the by product water, to form the imine, which is then reduced. The reduction can be carried out using methods well known to those of skill in the art, for example, by catalytic hydrogenation, or, preferably, with several hydride reagents in a reaction inert solvent. The catalytic hydrogenation can be carried out in the presence of a metal catalyst such as palladium or Raney nickel. Suitable hydride reagents include borohydrides such as sodium borohydride ($NaBH_4$), sodium cyanoborohydride ($NaBH_3CN$) and sodium triacetoxyborohydride ($NaB(OAc)_3H$), boranes, aluminum based reagents and trialkylsilanes. Suitable solvents include polar solvents such as methanol, ethanol, methylene chloride, dichloroethane, tetrahydrofuran (THF), dioxane, toluene, benzene and ethylacetate. This reaction is typically carried out at a temperature from about −78° C. to about the reflux temperature of the solvent, preferably from about 0° C. to about 25° C., for a period of about 5 minutes to about 48 hours, preferably from about 0.5 to 16 hours. The reduction is typically carried out using $NaB(OAc)_3H$, with or without the addition of acetic acid (HOAc), preferably in a polar solvent like methylene chloride ($CH_2Cl_2$) or dichloroethane. Alternatively, when $R^4$ and $R^5$ are hydrogen, the reaction product of formula 2, wherein $R^2$ is —$CH_3$, can be formed by using the method reported in Barluenga, J.; Bayon, A. M.; Asensio, G., *JCSCC* 1984, 1334–1335.

Scheme C

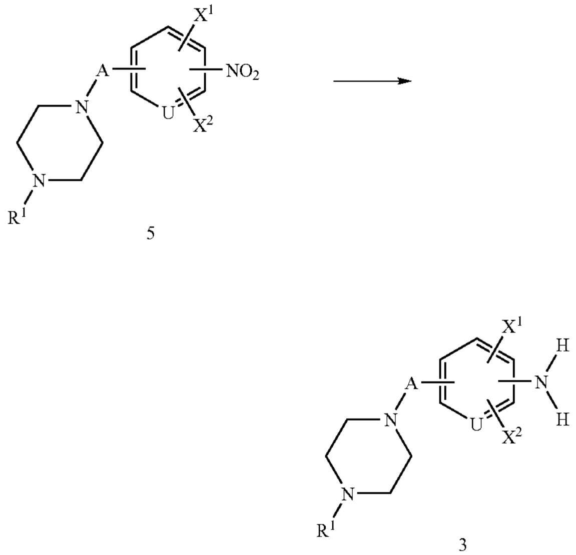

5

3

Scheme C illustrates a method for the preparation of compounds of the formula 3 by the reduction of compounds of the formula 5. This reduction can be achieved using standard methodology well known to those of skill in the art, preferably using a Raney nickel catalyst with hydrogen in a solvent such as dimethylformamide (DMF), tetrahydrofuran (THF), 1,4-dioxane, isopropanol, methanol or ethanol, preferably ethanol, in the presence of triethylamine. Other reducing agents that can be employed for this reduction include, but are not limited to, palladium with hydrogen ($Pd/H_2$) or ammonium formate, tin(II) chloride ($SnCl_2$), iron/hydrochloric acid (Fe/HCl), iron/acetic acid (Fe/HOAc), or sodium hydrogen sulfide/sodium sulfide ($NaSH/NaS_2$), in appropriate solvents such as ethyl acetate, DMF, N-methylpyrrolidinone (NMP), methanol, ethanol, isopropanol, dimethylacetamide (DMA), water or THF.

Scheme D

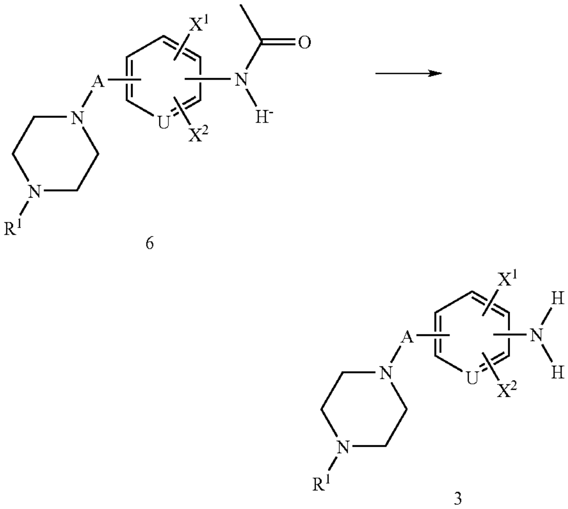

6

3

Scheme D illustrates a method of preparing compounds of the formula 3 by basic hydrolysis of the corresponding compounds of the formula 6. This can be done employing standard methodology well known to those of skill in the art, preferably using aqueous sodium hydroxide (NaOH) at reflux for several days.

Scheme E

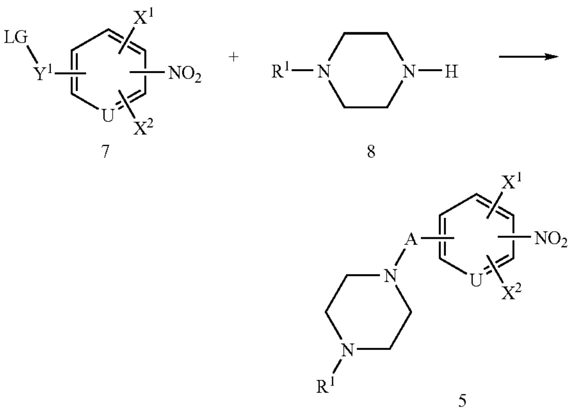

7 8

5

Scheme E illustrates a method for preparing compounds of the formula 5 wherein $y^1$ is $(CH_2)_p$, p is an integer from one to four and LG is Cl, Br, —OTs (tosylate), or —OMes (mesylate), by the alkylation of compounds of the formula 7 with a readily available piperazine of formula 8. This alkylation can be performed in a suitable polar solvent such as DMF, DMSO, ethyl acetate or acetonitrile, preferably acetonitrile, in the presence of a suitable base such as triethylamine or potassium carbonate, preferably $K_2CO_3$, with or without the addition of a small amount of water. The reaction is maintained at a temperature from about 25° C. to about the reflux temperature of the solvent for about 1 to about 24 hours, preferably 15 hours, or heated in a microwave reactor at about 150° C. for about 1–2 hours.

Scheme F

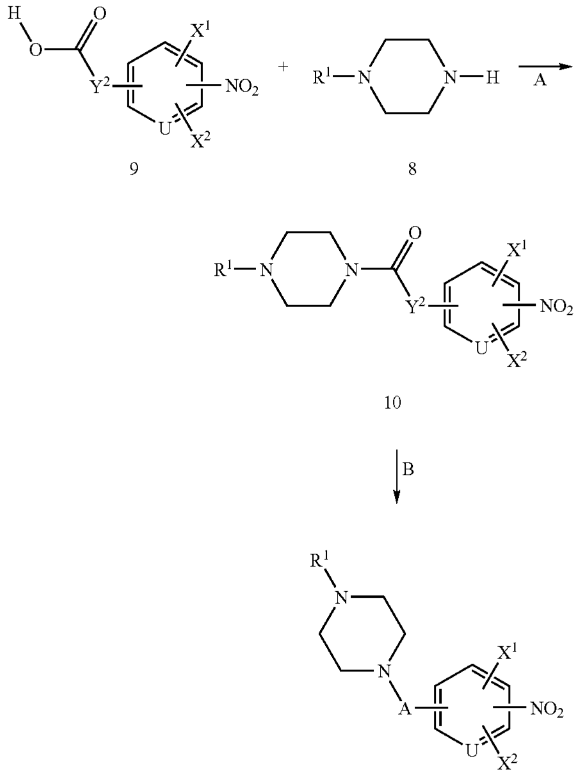

9 8

10

5

Scheme F illustrates a method for preparing compounds of the formula 5 from the corresponding compounds of the formula 9 wherein $Y^2$ is $(CH_2)_p$ and p is an integer of from one to three, by amide bond coupling with piperidines of the formula 8 followed by reduction of the amide bond in 10. Step A can be accomplished using any standard peptide coupling agent, preferably bis(2-oxo-3-oxazolidinyl)phosphonic chloride (BOP-Cl) at 0° C. to about ambient temperature, for a period of about 1 hour to about 24 hours, in an inert solvent such as dichloroethane or $CH_2Cl_2$, preferably $CH_2Cl_2$, to form the corresponding compounds of formula 10. The reduction of compounds of the formula 10 to those of the formula 5 can be performed using any standard reducing agent, preferably using borane dimethylsulfide in toluene at reflux for about 1 hour to about 24 hours.

Scheme G

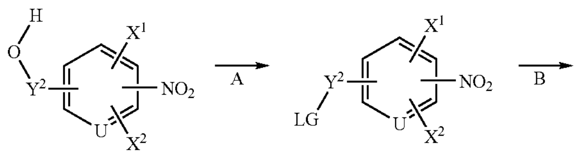

11 7

-continued

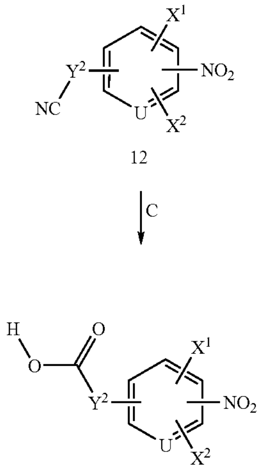

12

9

Scheme G illustrates a method for preparing compounds of the formula 9 wherein $Y^2$ is $(CH_2)_p$ and p is an integer from one to four, from the corresponding compounds of formula 11. Compounds of the formula 11 can be converted into compounds of the formula 7 wherein LG is Cl, Br, —OTs, or —OMs (Reaction A), using standard methodology well known to those of skill in the art. Compounds of the formula 7 can be converted into compounds of the formula 12 by displacement of the leaving group (LG) with a suitable source of cyanide anion such as sodium cyanide (NaCN) or, preferably, potassium cyanide, in a polar solvent such as dimethylformamide, dimethylsulfoxide, or a water/ethanol mixture, at a temperature from about 0° C. to about 100° C., for about 1 hour to 24 hours (Reaction B). The preferred conditions are potassium cyanide in a 50:50 mixture of water:ethanol at about 60° C. for about 1 hour. Compounds of the formula 9 can then be prepared by hydrolysis of the nitrile functionality under standard basic or, preferably, acidic conditions, preferably employing a $H_2O$/AcOH/HCl mixture at a temperature from about 0° C. to about 100° C., preferably at about 90° C., for about 5 hours, to give the desired acids (Reaction C).

Scheme H

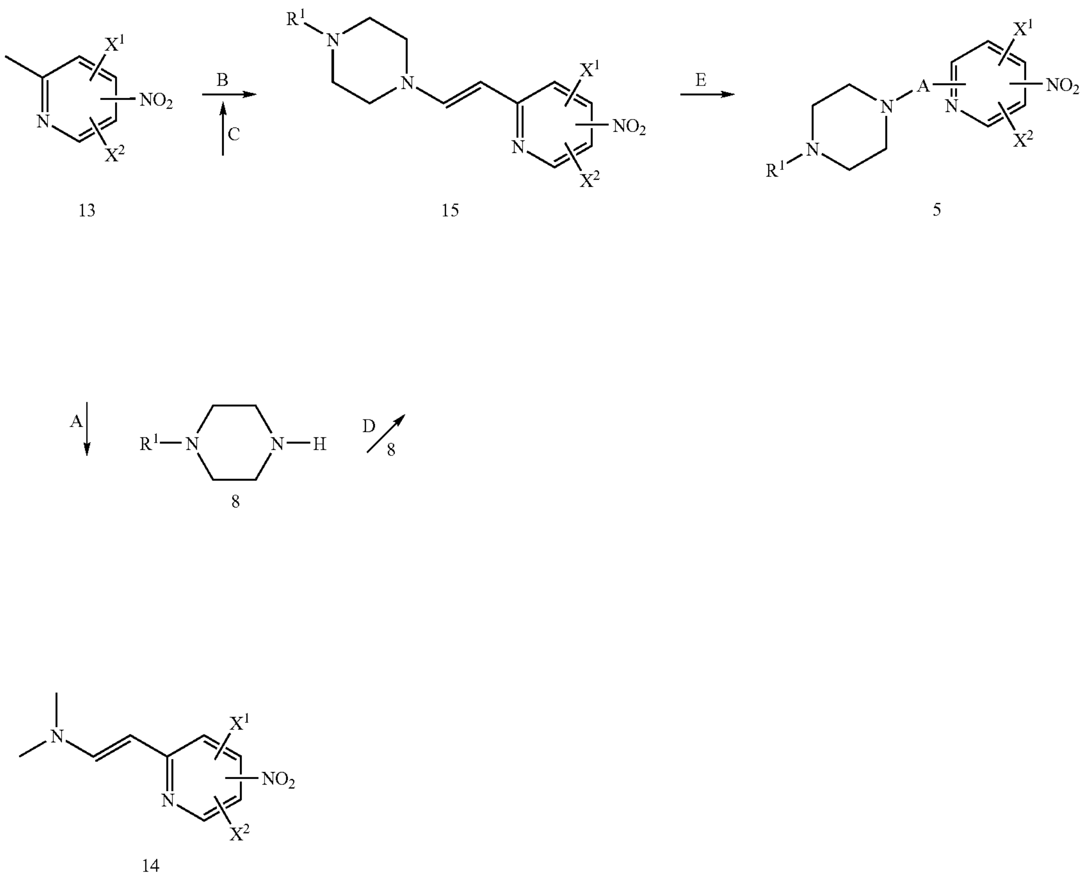

13

15

5

8

14

Scheme H illustrates a method for preparing compounds of the formula 5 wherein A is —$CH_2CH_2$—, $X^1$ is methyl and $X^2$ is hydrogen, from compounds of the formula 13 by formation of the enamine of the formula 15 followed by reduction of this enamine using standard methodology. The reaction of compounds of the formula 13 with dimethylformamide dimethylacetal in DMF gives compounds of the formula 14. This reaction is carried out as described in Vetelino, M. G.; Coe, J. W., TL 1994, 35, 219–222. The addition of piperazines of the formula 8 to compounds of the formula 14, followed by reduction of the resulting enamine, as described in Urban, F. J.; Breitenbach, R.; Gonyaw, D., *Synth. Commun.* 1996, 26, 1629–1638, gives the corresponding compounds of formula 5. Alternatively, the piperazines of the formula 8 can be initially condensed with dimethylformamide dimethylacetal, preferably at about 100° C. for about 6 hours, and then reacted further with compounds of the formula 13 in DMF, preferably at about 100° C., for about 1–2 days, to give the enamines of formula 15, which can then be carried forward to form compounds of the formula 5 as previously described.

Scheme I

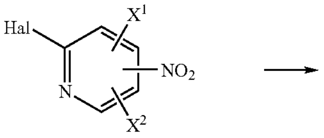

15

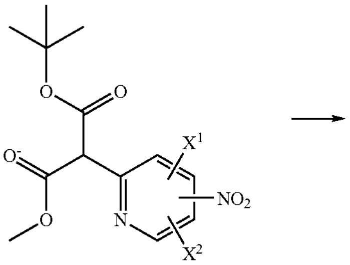

16

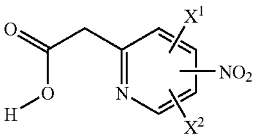

9

Scheme I illustrates a method for preparing compounds of the formula 9 wherein U is nitrogen and $y^2$ is methylene. Substituted 2-halopyridines of the formula 15 wherein Hal is halo, preferably chlorine, can be converted into compounds of the formula 16 by the process described in Ujjainwalla, F., Walsh, T. F., *TL* 2001, 42, 6441–6445. Reaction of compounds of the formula 15 with sodium hydride and t-butyl methyl malonate yields the corresponding compounds of formula 16. Treatment of compounds of the formula 16 with trifluoroacetic acid in dichloromethane, at a temperature from about 0° C. to about 50° C., preferably at about 25° C., leads to the formation of the corresponding compounds of formula 9.

Scheme J

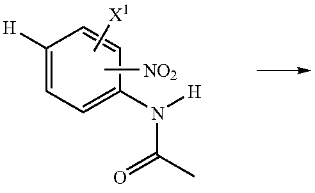

17

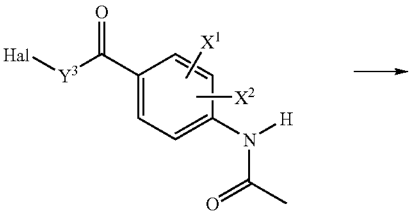

18

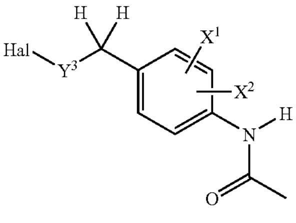

6

Scheme J illustrates a method for preparing compounds of the formula 6 wherein $Y^3$ is $(CH_2)_p$ wherein p is an integer from one to three and $X^1$ and $X^2$ are alkyl, from compounds of the formula 17. Compounds of the formula 17 can be reacted with compounds of the formula Hal-$Y^3$—COCl (wherein Hal is bromo or chloro, preferably chloro) in an appropriate inert solvent like carbon disulfide or dichloromethane, preferably dichloromethane, in the presence of a Lewis acid like aluminum chloride, at a temperature of about −78° C. to about 25° C., preferably at about 25° C., for about 1 to about 24 hours. Compounds of the formula 18 can be reduced to the corresponding compounds of formula 6 using triethylsilane/trifluoroacetic acid at a temperature between about −78° C. and about 50° C., preferably from about 0° C. to about 45° C., in a polar solvent such as dichloroethane or dichloromethane, preferably dichloromethane.

Scheme K

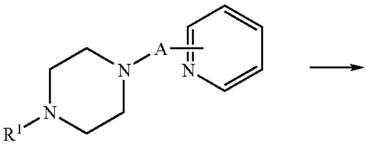

19

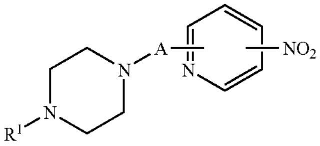

5a

Scheme K illustrates a method for preparing compounds of the formula 5 wherein $X^1$ and $X^2$ are hydrogen. Nitration of compounds of the formula 19, employing standard conditions well known to those of skill in the art, such as nitric acid or potassium nitrate in the presence of an acid such as hydrochloric acid or sulfuric acid, or, preferably, ammonium nitrate in the presence of trifluoroacetic acid anhydride, leads to the formation of the corresponding compounds of formula 5a.

Scheme L

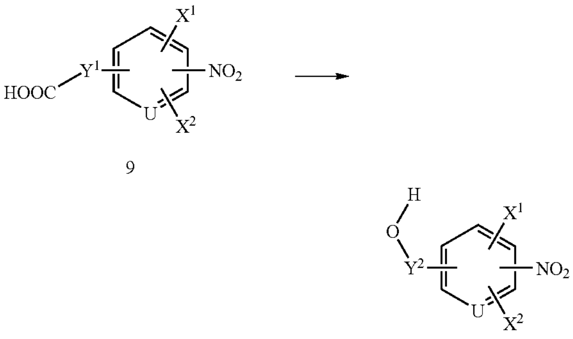

9

11

Scheme L illustrates a method of preparing compounds of formula 11, wherein $Y^2$ is $(CH_2)_{p+1}$ and p is an integer from 0 to 3, from compounds of formula 9, wherein $Y^1$ is $(CH_2)_p$ and p is defined as above. Compounds of the formula 11 can be prepared from compounds of formula 9 by reduction using lithium aluminum hydride or borane in an appropriate solvent such as THF or ether. A preferred solvent is borane in THF.

Scheme M illustrates a method of preparing compounds of the formula 22 from compounds of the formula 3.

Scheme M

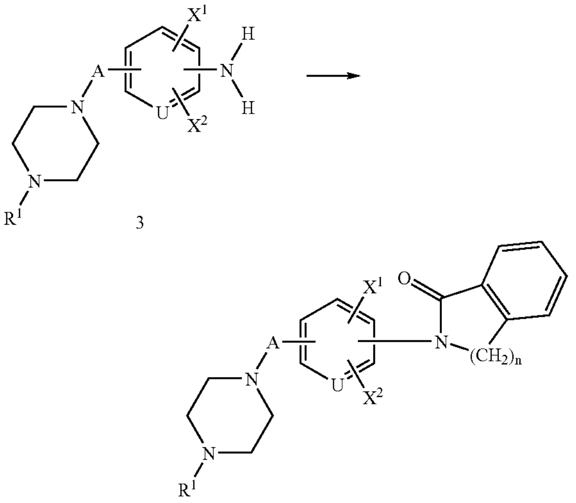

3

22

Referring to Scheme M, compounds of formula 22 (wherein n=1) can be prepared from compounds of formula 3 by treatment of compounds of formula 3 with o-phthaldialdehyde in acetonitrile at reflux in the presence of a catalytic amount of acetic acid as described in Azumaya, I, et. al. *J. Amer. Chem. Soc.,* 1991, 2833. Compounds of formula 22 (wherein n=2) can be prepared from compounds of formula 3 using the procedures described in Cheng, C., et. al. *J. Heterocyclic Chem.,* 1995, 73.

The preparation of other compounds of the formula 1 not specifically described in the foregoing experimental section can be accomplished using combinations of the reactions described above that will be apparent to those skilled in the art.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of the formula 1, and the intermediates shown in the above reaction schemes can be isolated and purified by conventional procedures, such as recrystallization or chromatographic separation.

The compounds of the formula 1 and their pharmaceutically acceptable salts can be administered to mammals via either the oral, parenteral (such as subcutaneous, intravenous, intramuscular, intrasternal and infusion techniques), rectal, buccal or intranasal routes. In general, these compounds are most desirably administered in doses ranging from about 3 mg to about 600 mg per day, in single or divided doses (i.e., from 1 to 4 doses per day), although variations will necessarily occur depending upon the species, weight and condition of the patient being treated, the patient's individual response to said medicament, the nature and severity of the particular disorder being treated, as well as on the type of pharmaceutical formulation chosen and the overall time period and intervals over which such administration is carried out. However, a dosage level that is in the range of about 25 mg to about 100 mg per day is most desirably employed. In some instances, dosage levels below the lower limit of the aforesaid range may be more than adequate, while in other cases still larger doses may be employed without causing any harmful side effects, provided that such higher dose levels are first divided into several small doses for administration throughout the day.

The compounds of the present invention may be administered alone or in combination with pharmaceutically acceptable carriers or diluents by any of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, suppositories, jellies, gels, pastes, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the weight ratio of the novel compounds of this invention to the pharmaceutically acceptable carrier will be in the range from about 1:6 to about 2:1, and preferably from about 1:4 to about 1:1.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art.

This invention relates to methods of treating anxiety, depression, schizophrenia and the other disorders referred to in the description of the methods of the present invention, wherein a novel compound of this invention and one or more of the other active agents referred to above (e.g., an NK1 receptor antagonist, tricyclic antidepressant, 5HT1D receptor antagonist, or serotonin reuptake inhibitor) are administered together, as part of the same pharmaceutical composition, as well as to methods in which such active agents are administered separately as part of an appropriate dose regimen designed to obtain the benefits of the combination therapy. The appropriate dose regimen, the amount of each dose of an active agent administered, and the specific intervals between doses of each active agent will depend upon the subject being treated, the specific active agent being administered and the nature and severity of the specific disorder or condition being treated. In general, the novel compounds of this invention, when used as a single active agent or in combination with another active agent, will be administered to an adult human in an amount from about 3 mg to about 600 mg per day, in single or divided doses, preferably from about 25 to about 100 mg per day. Such compounds may be administered on a regimen of up to 6 times per day, preferably 1 to 4 times per day, especially 2 times per day and most especially once daily. Variations may nevertheless occur depending on the species, weight and condition of the patient being treated, the patient's individual response to said medicament, the nature and severity of the particular disorder being treated, as well as on the type of pharmaceutical formulation chosen and the overall time period and intervals over which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

A proposed daily dose of a 5HT reuptake inhibitor, preferably sertraline, in the combination methods and compositions of this invention, for oral, parenteral or buccal administration to the average adult human for the treatment of the conditions referred to above, is from about 0.1 mg to about 2000 mg, preferably from about 1 mg to about 200 mg of the 5HT reuptake inhibitor per unit dose, which could be administered, for example, 1 to 4 times per day. A proposed daily dose of a 5HT1 D receptor antagonist in the combination methods and compositions of this invention, for oral, parenteral, rectal or buccal administration to the average adult human for the treatment of the conditions referred to above, is from about 0.01 mg to about 2000 mg, preferably from about 0.1 mg to about 200 mg of the 5HT1D receptor antagonist per unit dose, which could be administered, for example, 1 to 4 times per day.

For intranasal administration or administration by inhalation, the novel compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch. Formulations of the active compounds of this invention for treatment of the conditions referred to above in the average adult human are preferably prepared so that each metered dose or "puff" of aerosol contains 20 μg to 1000 μg of active compound. The overall daily dose with an aerosol will be within the range 100 μg to 10 mg. Administration may be several times daily, for example 2, 3, 4 or 8 times, giving for example, 1, 2 or 3 doses each time.

The ability of the compounds of this invention to bind to the dopamine D2 and serotonin 2A (5HT2A) receptors can be determined using conventional radioligand receptor binding assays. All receptors can be heterologously expressed in cell lines and experiments conducted in membrane preparations from the cell lines using procedures outlined below. $IC_{50}$ concentrations can be determined by nonlinear regression of concentration-dependent reduction in specific binding. The Cheng-Prussoff equation can be used to convert the $IC_{50}$ to Ki concentrations.

Dopamine D2 Receptor Binding:

$[^3H]$Spiperone binding to a membrane preparation from CHO-hD2L cells is carried out in 250 μl of 50 mM Tris-HCl buffer containing 100 mM NaCl, 1 mM $MgCl_2$ and 1% DMSO at pH 7.4. Duplicate samples containing (in order of addition) the test compounds, 0.4 nM $[^3H]$spiperone and approximately 12 μg protein are incubated for 120 minutes at room temperature. Bound radioligand is separated by rapid filtration under reduced pressure through Whatman GF/B glass fiber filters previously treated with 0.3% polyethyleneimine. Radioactivity retained on the filter is determined by liquid scintillation spectrophotometry.

The title compounds of Examples 1–524 were tested using the above assay, in which specific binding determined in the presence of 1 mM haloperidol was 95%. All of the title compounds of Examples 1–524 exhibited $IC_{50}$ values less than or equal to 1 uM. The title compound of Example 102 exhibited a Ki of 8.2 nM. The title compound of Example 364 exhibited a Ki of 8.58 nM. The title compound of Example 27 exhibited a Ki of 6.32 nM.

Serotonin 2A Binding:

[$^3$H] Ketanserin binding to Swiss-h5HT2A cell membranes can be carried out in 250 µl of 50 mM Tris-HCl buffer pH 7.4. Duplicate samples containing (in order of addition) test compounds, 1.0 nM [$^3$H]ketanserin, and approximately 75 µg protein are incubated for 120 minutes at room temperature. Bound radioligand is separated by rapid filtration under reduced pressure through Whatman GF/B glass fiber filters previously treated with 0.3% polyethyleneimine. Radioactivity retained on the filter is determined by liquid scintillation spectrophotometry.

The title compounds of Examples 1–524 were tested using the above assay, in which specific binding determined in the presence of 1 mM ketanserin was 90%. All of the title compounds of Examples 1–524 exhibited $IC_{50}$ values less than or equal to 1 uM. The title compound of Example 102 exhibited a Ki of 0.25 nM. The title compound of Example 27 exhibited a Ki of 1.46 nM. The title compound of Example 364 exhibited a Ki of 0.29 nM.

The following Examples illustrate the preparation of the compounds of the present invention. Melting points are uncorrected. NMR data are reported in parts per million and are referenced to the deuterium lock signal from the sample solvent.

EXAMPLES

Preparation 1

4-NITROPHENETHYL TOSYLATE

4-Nitrophenethyl alcohol (15 g, 89.7 mmol) was dissolved in 450 mL methylene chloride. Triethylamine (37.5 mL, 269 mmol) was added over 10 min and the reaction mixture was stirred at 0° C. for 1 hour (h). Tosyl chloride (20.52 g, 110 mmol) was added slowly to the mixture at 0° C. The reaction was stirred at room temperature (rt) overnight and was concentrated. The residue was dissolved in methylene chloride and washed with water, 1 N HCl, then water. The organic layer was dried over sodium sulfate and evaporated. The residue was triturated with hexanes and 25.32 g of white solid was collected. Yield 88%; $^1$H NMR (400 MHz, $CDCl_3$) δ 8.07 (d, J=8 Hz, 2H), 7.63 (d, J=8 Hz, 2H), 7.24 (d, 4H), 4.26 (t, J=6 Hz, 2H), 3.04 (t, J=6 Hz, 2H), 2.41 (s, 3H).

Preparation 2

3-{4-[2-(4-NITRO-PHENYL)-ETHYL]-PIPERAZIN-1-YL}-1,2-BENZISOTHIAZOLE

Excess dried, −325 mesh potassium carbonate (20 g) was diluted in 500 mL acetone and 3-piperazin-1-yl-benzoisothiazole hydrochloride (13.05 g, 51.2 mmol) was added. The mixture was stirred for 15 min before 4-nitrophenethyl tosylate (14.93 g, 46.5 mmol) and catalytic 18-crown-6 (0.5 g, 1.9 mmol) was added. The mixture was stirred at reflux for 42 h. After cooling, the salts were filtered off and washed with acetone and the filtrate was concentrated. The residue was taken up in methylene chloride and washed with water. The organic layer was dried over sodium sulfate, and concentrated. The residue was triturated with ethyl acetate and the collected solid was washed with ethyl ether and dried in vacuo to afford 14.86 g of a bright yellow solid. Yield 84%; mp 99° C.; MS (APCI): 369 $[M+H]^+$.

Preparation 3

4-[2-(4-1,2-BENZISOTHIAZOL-3-YL-PIPERAZIN-1-YL)-ETHYL]-PHENYLAMINE

3-{4-[2-(4-Nitro-phenyl)-ethyl]-piperazin-1-yl}-1,2-benzisothiazole (942 mg, 2.56 mmol) was dissolved in 50 mL of THF treated with triethylamine (0.3 mL) and with wet Raney nickel (0.14 g). The resulting mixture was placed on a shaker type hydrogenator, purged with hydrogen, pressurized (two re-pressurizations were needed to maintain the pressure between 3 and 17 psig) and shaken at room temperature for 64 hours. The resulting mixture was filtered to remove the catalyst then filtered a second time over celite before the filtrate was concentrated. The resultant white solid was dried in vacuo (830 mg, 2.45 mmol). Yield 96%; mp 154° C.; MS (APCI): 339 $[M+H]^+$.

Example 1

N-{4-[2-(4-1,2-BENZISOTHIAZOL-3-YL-PIPERAZIN-1-YL)-ETHYL]-PHENYL}-2,2-DIMETHYL-PROPIONAMIDE

4-[2-(4-1,2-Benzisothiazol-3-yl-piperazin-1-yl)-ethyl]-phenylamine (135 mg, 0.4 mmol) was dissolved in 5 ml THF and triethylamine was added (112 µL, 0.8 mmol). Trimethyl acetyl chloride (49.3 µL, 0.4 mmol) was added under stirring and the reaction stirred at room temperature overnight. The reaction mixture was concentrated under nitrogen and dissolved in 5 ml methylene chloride and then washed with water. The organic layer was concentrated and evaluated by LCMS. The mixture was purified by MPLC using a Biotage 40s prepacked silica gel cartridge eluting with 3% methanol in methylene chloride. N-{4-[2-(4-1,2-Benzisothiazol-3-yl-piperazin-1-yl)-ethyl]-phenyl}-2,2-dimethyl-propionamide (156 mg) was isolated in 98.2% purity @ 254 nm; LCMS (APCI): 423 [M+H]+

The amides of Examples 2–36 were synthesized in combinatorial library format using appropriate acid chloride starting materials and phenyl amines on a 0.4 mmol scale and following the steps as outlined in Example 1. The crude products were dissolved in $CH_2Cl_2$ and purified by MPLC using a Biotage 40s prepacked silica gel cartridge and eluting with 3% methanol in methylene chloride.

Preparation 4

2-NITROPHENETHYL TOSYLATE

2-Nitrophenethyl tosylate was prepared according to the general method as outlined in Preparation 1 starting from 2-nitrophenethyl alcohol (15 g, 89.7 mmol) and tosyl chloride (20.52 g, 110 mmol). The residue was triturated with hexanes and 26.44 g of off white crystals were collected. Yield 92%; $^1$H NMR (400 MHz, $CDCl_3$) δ 7.93 (d, J=9.7 Hz, 1H), 7.91 (d, J=9.7 Hz, 2H), 7.64 (t, 1H), 7.39 (m, 2H), 7.24 (s, 2H), 4.32 (t, J=6 Hz, 2H), 3.24 (t, J=6 Hz, 2H), 2.41 (s, 3H).

Preparation 5

3-{4-[2-(2-NITRO-PHENYL)-ETHYL]-PIPERAZIN-1-YL}-1,2-BENZISOTHIAZOLE

3-{4-[2-(2-Nitro-phenyl)-ethyl]-piperazin-1-yl}-1,2-benzisothiazole was prepared according to the general method as outlined in Preparation 2 starting with 3-piperazin-1-yl-benzoisothiazole hydrochloride (13.37 g, 52.4 mmol) and 2-nitrophenethyl tosylate (15.3 g, 47.7 mmol). The product was isolated via column chromatography to afford 13.08 g of a viscous, brown liquid. Yield 75%; MS (APCI): 369 $[M+H]^+$.

Preparation 6

2-[2-(4-1,2-BENZISOTHIAZOL-3-YL-PIPERAZIN-1-YL)-ETHYL]-PHENYLAMINE

2-[2-(4-1,2-Benzisothiazol-3-yl-piperazin-1-yl)-ethyl]-phenylamine was prepared according to the general method as outlined in Preparation 3 starting from 3-{4-[2-(2-nitro-phenyl)-ethyl]-piperazin-1-yl}-1,2-benzisothiazole (12.93 g, 35.13 mmol). The resultant white solid was triturated with ethyl ether and dried in vacuo (7.88 g). Yield 66%; mp 149° C.; MS (APCI): 339 $[M+H]^+$.

Example 2

N-{2-[2-(4-1,2-BENZISOTHIAZOL-3-YL-PIPERAZIN-1-YL)-ETHYL]-PHENYL}-2,2-DIMETHYL-PROPIONAMIDE

Starting from 2-[2-(4-1,2-benzisothiazol-3-yl-piperazin-1-yl)-ethyl]-phenylamine, 109 mg of N-{2-[2-(4-1,2-benzisothiazol-3-yl-piperazin-1-yl)-ethyl]-phenyl}-2,2-dimethyl-propionamide was isolated in 99% purity @ 254 nm; LCMS (APCI): 423 $[M+H]^+$; $^1H$ NMR (400 MHz, $CDCl_3$) δ 8.27 (s, 1H), 7.84 (d, J=8 Hz, 1H), 7.78 (d, J=8 Hz, 1H), 7.74 (d, J=8 Hz, 1H), 7.46 (t, 1H), 7.34 (t, 1H), 7.30 (m, 2H), 7.10 (t, 1H), 3.53 (m, 4H), 2.82 (m, 2H), 2.67 (m, 6H), 1.35 (s, 9H).

Preparation 7

3-NITROPHENETHYL TOSYLATE

3-Nitrophenethyl tosylate was prepared according to the general method as outlined in Preparation 1 starting from 3-nitrophenethyl alcohol (15 g, 89.7 mmol) and tosyl chloride (20.52 g, 110 mmol). The product was isolated as an off white powder (21.5 g). Yield 96%; $^1H$ NMR (400 MHz, $CDCl_3$) δ 8.06 (d, 1H), 7.87 (t, 1H), 7.63 (d, 2H), 7.46 (m, 2H), 7.25 (m, 2H), 4.26 (t, J=6 Hz, 2H), 3.04 (t, J=6 Hz, 2H), 2.40 (s, 3H).

Preparation 8

3-{4-[2-(3-NITRO-PHENYL)-ETHYL]-PIPERAZIN-1-YL}-1,2-BENZISOTHIAZOLE

3-{4-[2-(3-Nitro-phenyl)-ethyl]-piperazin-1-yl}-1,2-benzisothiazole was prepared according to the general method as outlined in Preparation 2 starting from 3-piperazin-1-yl-benzoisothiazole hydrochloride (12.51 g, 49.1 mmol) and 2-nitrophenethyl tosylate (15 g, 46.7 mmol). The product was isolated via column chromatography to afford 15.5 g of a yellow powder. Yield 90%; mp 101° C.; MS (APCI): 369 $[M+H]^+$.

Preparation 9

3-[2-(4-1,2-BENZISOTHIAZOL-3-YL-PIPERAZIN-1-YL)-ETHYL]-PHENYLAMINE

3-[2-(4-1,2-Benzisothiazol-3-yl-piperazin-1-yl)-ethyl]-phenylamine was prepared according to the general method as outlined in Preparation 3 starting from 3-{4-[2-(3-nitro-phenyl)-ethyl]-piperazin-1-yl}-1,2-benzisothiazole (10 g, 27.1 mmol). The resultant white solid was dried in vacuo (9.52 g). Yield 95%; mp 108° C.; MS (APCI): 339 $[M+H]^+$.

Example 3 (PD 333575)

N-{3-[2-(4-1,2-BENZISOTHIAZOL-3-YL-PIPERAZIN-1-YL)-ETHYL]-PHENYL}-2,2-DIMETHYL-PROPIONAMIDE

Starting from 3-[2-(4-1,2-benzisothiazol-3-yl-piperazin-1-yl)-ethyl]-phenylamine, 144 mg of N-{3-[2-(4-1,2-benzisothiazol-3-yl-piperazin-1-yl)-ethyl]-phenyl}-2,2-dimethyl-propionamide was isolated in 100% purity @ 254 nm; LCMS (APCI): 423 $[M+H]^+$; $^1H$ NMR (400 MHz, $CDCl_3$) δ 7.89 (d, J=8 Hz, 1H), 7.80 (d, J=8 Hz, 1H), 7.57 (s, 1H), 7.51 (m, 1H), 7.47 (m, 1H), 7.33 (m, 2H), 6.97 (d, J=7 Hz, 1H), 3.61 (m, 4H), 2.78 (m, 8H), 1.30 (s, 9H).

Example 4 (PD 334464)

N-{2-[2-(4-1,2-BENZISOTHIAZOL-3-YL-PIPERAZIN-1-YL)-ETHYL]-PHENYL}-SUCCINAMIC ACID ETHYL ESTER

Starting from 2-[2-(4-1,2-benzisothiazol-3-yl-piperazin-1-yl)-ethyl]-phenylamine, 75 mg of N-{2-[2-(4-1,2-benzisothiazol-3-yl-piperazin-1-yl)-ethyl]-phenyl}-succinamic acid ethyl ester was isolated. LCMS (APCI): 467 $[M+H]^+$; $^1H$ NMR (400 MHz, $CDCl_3$) δ 9.87 (s, 1H), 7.86 (d, J=8 Hz, 2H), 7.80 (d, J=8 Hz, 1H), 7.45 (t, 1H), 7.34 (t, 1H), 7.20 (t, 1H), 7.18 (d, 1H), 7.03 (t, 1H), 4.10 (q, 2H), 3.61 (m, 4H), 2.85 (m, 6H), 2.82 (m, 6H), 1.20 (t, 3H).

Example 5

N-{3-[2-(4-1,2-BENZISOTHIAZOL-3-YL-PIPERAZIN-1-YL)-ETHYL]-PHENYL}-SUCCINAMIC ACID ETHYL ESTER

Starting from 3-[2-(4-1,2-benzisothiazol-3-yl-piperazin-1-yl)-ethyl]-phenylamine, 193 mg of N-{3-[2-(4-1,2-benzisothiazol-3-yl-piperazin-1-yl)-ethyl]-phenyl}-succinamic acid ethyl ester was isolated in 94% purity @ 254 nm; LCMS (APCI): 467 $[M+H]^+$.

Example 6

N-{4-[2-(4-1,2-BENZISOTHIAZOL-3-YL-PIPERAZIN-1-YL)-ETHYL]-PHENYL}-SUCCINAMIC ACID ETHYL ESTER

Starting from 4-[2-(4-1,2-benzisothiazol-3-yl-piperazin-1-yl)-ethyl]-phenylamine, 133 mg of N-{4-[2-(4-1,2-benzisothiazol-3-yl-piperazin-1-yl)-ethyl]-phenyl}-succinamic acid ethyl ester was isolated in 86% purity @ 254 nm; LCMS (APCI): 467 $[M+H]^+$.

Example 7

N-{2-[2-(4-1,2-BENZISOTHIAZOL-3-YL-PIPERAZIN-1-YL)-ETHYL]-PHENYL}-PROPIONAMIDE

Starting from 2-[2-(4-1,2-benzisothiazol-3-yl-piperazin-1-yl)-ethyl]-phenylamine, 63 mg of N-{2-[2-(4-1,2-benzisothiazol-3-yl-piperazin-1-yl)-ethyl]-phenyl}-propionamide was isolated in 99% purity @ 254 nm; LCMS (APCI): 395 $[M+H]^+$.

Example 8

N-{2-[2-(4-1,2-BENZISOTHIAZOL-3-YL-PIPERAZIN-1-YL)-ETHYL]-PHENYL}-2-PHENOXY-PROPIONAMIDE

Starting from 2-[2-(4-1,2-benzisothiazol-3-yl-piperazin-1-yl)-ethyl]-phenylamine, 78 mg of N-{2-[2-(4-1,2-benzisothiazol-3-yl-piperazin-1-yl)-ethyl]-phenyl}-2-phenoxy-propionamide was isolated; LCMS (APCI): 487 $[M+H]^+$. $^1H$ NMR (400 MHz, $CDCl_3$) δ 9.20 (s, 1H), 7.76 (m, 3H), 7.39 (t, 1H), 7.23 (m, 4H), 7.03 (m, 2H), 6.92 (m, 3H), 4.67 (q, 1H), 3.44 (m, 4H), 2.51 (m, 8H), 1.62 (m, 3H).

Example 9

N-{3-[2-(4-1,2-BENZISOTHIAZOL-3-YL-PIPERAZIN-1-YL)-ETHYL]-PHENYL}-2-PHENOXY-PROPIONAMIDE

Starting from 3-[2-(4-1,2-benzisothiazol-3-yl-piperazin-1-yl)-ethyl]-phenylamine, 29 mg of N-{3-[2-(4-1,2-benzisothiazol-3-yl-piperazin-1-yl)-ethyl]-phenyl}-2-phenoxy-propionamide was isolated in 95% purity @ 254 nm; LCMS (APCI): 487 $[M+H]^+$.

Example 10

N-{2-[2-(4-1,2-BENZISOTHIAZOL-3-YL-PIPERAZIN-1-YL)-ETHYL]-PHENYL}-2-THIOPHEN-2-YL-ACETAMIDE

Starting from 2-[2-(4-1,2-benzisothiazol-3-yl-piperazin-1-yl)-ethyl]-phenylamine, 29 mg of N-{2-[2-(4-1,2-benzisothiazol-3-yl-piperazin-1-yl)-ethyl]-phenyl}-2-thiophen-2-yl-acetamide was isolated in 99% purity @ 254 nm; LCMS (APCI): 463 $[M+H]^+$.

Example 11

N-{3-[2-(4-1,2-BENZISOTHIAZOL-3-YL-PIPERAZIN-1-YL)-ETHYL]-PHENYL}-2-THIOPHEN-2-YL-ACETAMIDE

Starting from 3-[2-(4-1,2-benzisothiazol-3-yl-piperazin-1-yl)-ethyl]-phenylamine, 178 mg of N-{3-[2-(4-1,2-benzisothiazol-3-yl-piperazin-1-yl)-ethyl]-phenyl}-2-thiophen-2-yl-acetamide was isolated in 93% purity @ 254 nm; LCMS (APCI): 463 $[M+H]^+$.

Example 12

N-{4-[2-(4-1,2-BENZISOTHIAZOL-3-YL-PIPERAZIN-1-YL)-ETHYL]-PHENYL}-2-THIOPHEN-2-YL-ACETAMIDE

Starting from 4-[2-(4-1,2-benzisothiazol-3-yl-piperazin-1-yl)-ethyl]-phenylamine, 60 mg of N-{4-[2-(4-1,2-benzisothiazol-3-yl-piperazin-1-yl)-ethyl]-phenyl}-2-thiophen-2-yl-acetamide was isolated in 97% purity @ 254 nm; LCMS (APCI): 463 $[M+H]^+$.

Example 13

N-{2-[2-(4-1,2-BENZISOTHIAZOL-3-YL-PIPERAZIN-1-YL)-ETHYL]-PHENYL}-2-(4-METHOXY-PHENYL)-ACETAMIDE

Starting from 2-[2-(4-1,2-benzisothiazol-3-yl-piperazin-1-yl)-ethyl]-phenylamine, 95 mg of N-{2-[2-(4-1,2-benzisothiazol-3-yl-piperazin-1-yl)-ethyl]-phenyl}-2-(4-methoxy-phenyl)-acetamide was isolated in 98% purity @ 254 nm; LCMS (APCI): 487 $[M+H]^+$.

Example 14

N-{3-[2-(4-1,2-BENZISOTHIAZOL-3-YL-PIPERAZIN-1-YL)-ETHYL]-PHENYL}-2-(4-METHOXY-PHENYL)-ACETAMIDE

Starting from 3-[2-(4-1,2-benzisothiazol-3-yl-piperazin-1-yl)-ethyl]-phenylamine, 127 mg of N-{3-[2-(4-1,2-benzisothiazol-3-yl-piperazin-1-yl)-ethyl]-phenyl}-2-(4-methoxy-phenyl)-acetamide was isolated in 99% purity @ 254 nm; LCMS (APCI): 487 $[M+H]^+$.

Example 15

N-{4-[2-(4-1,2-BENZISOTHIAZOL-3-YL-PIPERAZIN-1-YL)-ETHYL]-PHENYL}-2-(4-METHOXY-PHENYL)-ACETAMIDE

Starting from 4-[2-(4-1,2-benzisothiazol-3-yl-piperazin-1-yl)-ethyl]-phenylamine, 88 mg of N-{4-[2-(4-1,2-benzisothiazol-3-yl-piperazin-1-yl)-ethyl]-phenyl}-2-(4-methoxy-phenyl)-acetamide was isolated in 90% purity @ 254 nm; LCMS (APCI): 487 $[M+H]^+$.

Example 16

N-{2-[2-(4-1,2-BENZISOTHIAZOL-3-YL-PIPERAZIN-1-YL)-ETHYL]-PHENYL}-2-PHENOXY-BUTYRAMIDE

Starting from 2-[2-(4-1,2-benzisothiazol-3-yl-piperazin-1-yl)-ethyl]-phenylamine, 107 mg of N-{2-[2-(4-1,2-benzisothiazol-3-yl-piperazin-1-yl)-ethyl]-phenyl}-2-phenoxy-butyramide was isolated; LCMS (APCI): 501 $[M+H]^+$. $^1H$ NMR (400 MHz, $CDCl_3$) δ 9.15 (s, 1H), 7.77 (m, 3H), 7.41 (t, 1H), 7.20 (m, 4H), 7.06 (m, 2H), 6.95 (m, 3H), 4.53 (q, 1H), 3.47 (m, 4H), 2.47 (m, 8H), 2.02 (m, 2H), 1.07 (m, 3H).

Example 17

N-{3-[2-(4-1,2-BENZISOTHIAZOL-3-YL-PIPERAZIN-1-YL)-ETHYL]-PHENYL}-2-PHENOXY-BUTYRAMIDE

Starting from 3-[2-(4-1,2-benzisothiazol-3-yl-piperazin-1-yl)-ethyl]-phenylamine, 37 mg of N-{3-[2-(4-1,2-benzisothiazol-3-yl-piperazin-1-yl)-ethyl]-phenyl}-2-phenoxy-butyramide was isolated in 92% purity @ 254 nm; LCMS (APCI): 501 $[M+H]^+$.

Example 18

N-{4-[2-(4-1,2-BENZISOTHIAZOL-3-YL-PIPERAZIN-1-YL)-ETHYL]-PHENYL}-2-PHENOXY-BUTYRAMIDE

Starting from 4-[2-(4-1,2-benzisothiazol-3-yl-piperazin-1-yl)-ethyl]-phenylamine, 58 mg of N-{4-[2-(4-1,2-benzisothiazol-3-yl-piperazin-1-yl)-ethyl]-phenyl}-2-phenoxy-butyramide was isolated in 86% purity @ 254 nm; LCMS (APCI): 501 $[M+H]^+$.

Example 19

N-{2-[2-(4-1,2-BENZISOTHIAZOL-3-YL-PIPERAZIN-1-YL)-ETHYL]-PHENYL}-2-(3-METHOXY-PHENYL)-ACETAMIDE

Starting from 2-[2-(4-1,2-benzisothiazol-3-yl-piperazin-1-yl)-ethyl]-phenylamine, 50 mg of N-{2-[2-(4-1,2-benzisothiazol-3-yl-piperazin-1-yl)-ethyl]-phenyl}-2-(3-methoxy-phenyl)-acetamide was isolated in 97% purity @ 254 nm; LCMS (APCI): 487 $[M+H]^+$.

Example 20

N-{3-[2-(4-1,2-BENZISOTHIAZOL-3-YL-PIPERAZIN-1-YL)-ETHYL]-PHENYL}-2-(3-METHOXY-PHENYL)-ACETAMIDE

Starting from 3-[2-(4-1,2-benzisothiazol-3-yl-piperazin-1-yl)-ethyl]-phenylamine, 105 mg of N-{3-[2-(4-1,2-benzisothiazol-3-yl-piperazin-1-yl)-ethyl]-phenyl}-2-(3-methoxy-phenyl)-acetamide was isolated in 94% purity @ 254 nm; LCMS (APCI): 487 $[M+H]^+$.

Example 21

N-{4-[2-(4-1,2-BENZISOTHIAZOL-3-YL-PIPERAZIN-1-YL)-ETHYL]-PHENYL}-2-(3-METHOXY-PHENYL)-ACETAMIDE

Starting from 4-[2-(4-1,2-benzisothiazol-3-yl-piperazin-1-yl)-ethyl]-phenylamine, 32 mg of N-{4-[2-(4-1,2-benzisothiazol-3-yl-piperazin-1-yl)-ethyl]-phenyl}-2-(3-methoxy-phenyl)-acetamide was isolated in 97% purity @ 254 nm; LCMS (APCI): 487 $[M+H]^+$.

Example 22

3,5-DIMETHYL-ISOXAZOLE-4-CARBOXYLIC ACID {2-[2-(4-1,2-BENZISOTHIAZOL-3-YL-PIPERAZIN-1-YL)-ETHYL]-PHENYL}-AMIDE

Starting from 2-[2-(4-1,2-benzisothiazol-3-yl-piperazin-1-yl)-ethyl]-phenylamine, 65 mg of 3,5-dimethyl-isoxazole-4-carboxylic acid {2-[2-(4-1,2-benzisothiazol-3-yl-piperazin-1-yl)-ethyl]-phenyl}-amide was isolated in 95% purity @ 254 nm; LCMS (APCI): 462 $[M+H]^+$.

Example 23

3,5-DIMETHYL-ISOXAZOLE-4-CARBOXYLIC ACID {3-[2-(4-1,2-BENZISOTHIAZOL-3-YL-PIPERAZIN-1-YL)-ETHYL]-PHENYL}-AMIDE

Starting from 3-[2-(4-1,2-benzisothiazol-3-yl-piperazin-1-yl)-ethyl]-phenylamine, 223 mg of 3,5-dimethyl-isoxazole-4-carboxylic acid {3-[2-(4-1,2-benzisothiazol-3-yl-piperazin-1-yl)-ethyl]-phenyl}-amide was isolated in 95% purity @ 254 nm; LCMS (APCI): 462 $[M+H]^+$.

Example 24

3,5-DIMETHYL-ISOXAZOLE-4-CARBOXYLIC ACID {4-[2-(4-1,2-BENZISOTHIAZOL-3-YL-PIPERAZIN-1-YL)-ETHYL]-PHENYL}-AMIDE

Starting from 4-[2-(4-1,2-benzisothiazol-3-yl-piperazin-1-yl)-ethyl]-phenylamine, 114 mg of 3,5-dimethyl-isoxazole-4-carboxylic acid {4-[2-(4-1,2-benzisothiazol-3-yl-piperazin-1-yl)-ethyl]-phenyl}-amide was isolated in 95% purity @ 254 nm; LCMS (APCI): 462 $[M+H]^+$.

Example 25

2,5-DIMETHYL-FURAN-3-CARBOXYLIC ACID {2-[2-(4-1,2-BENZISOTHIAZOL-3-YL-PIPERAZIN-1-YL)-ETHYL]-PHENYL}-AMIDE

Starting from 2-[2-(4-1,2-benzisothiazol-3-yl-piperazin-1-yl)-ethyl]-phenylamine, 60 mg of 2,5-dimethyl-furan-3-carboxylic acid {2-[2-(4-1,2-benzisothiazol-3-yl-piperazin-1-yl)-ethyl]-phenyl}-amide was isolated in 97% purity @ 254 nm; LCMS (APCI): 461 $[M+H]^+$.

Example 26

2,5-DIMETHYL-FURAN-3-CARBOXYLIC ACID {3-[2-(4-12-BENZISOTHIAZOL-3-YL-PIPERAZIN-1-YL)-ETHYL]-PHENYL}-AMIDE

Starting from 3-[2-(4-1,2-benzisothiazol-3-yl-piperazin-1-yl)-ethyl]-phenylamine, 209 mg of 2,5-dimethyl-furan-3-carboxylic acid {3-[2-(4-1,2-benzisothiazol-3-yl-piperazin-1-yl)-ethyl]-phenyl}-amide was isolated in 96% purity @ 254 nm; LCMS (APCI): 461 $[M+H]^+$.

Example 27

2,5-DIMETHYL-FURAN-3-CARBOXYLIC ACID {4-[2-(4-1,2-BENZISOTHIAZOL-3-YL-PIPERAZIN-1-YL)-ETHYL]-PHENYL}-AMIDE

Starting from 4-[2-(4-1,2-benzisothiazol-3-yl-piperazin-1-yl)-ethyl]-phenylamine, 93 mg of 2,5-dimethyl-furan-3-carboxylic acid {4-[2-(4-1,2-benzisothiazol-3-yl-piperazin-1-yl)-ethyl]-phenyl}-amide was isolated in 99% purity @ 254 nm; LCMS (APCI): 461 $[M+H]^+$.

Example 28

ACETIC ACID 1-{2-[2-(4-1,2-BENZISOTHIAZOL-3-YL-PIPERAZIN-1-YL)-ETHYL]-PHENYLCARBAMOYL}-ETHYL ESTER

Starting from 2-[2-(4-1,2-benzisothiazol-3-yl-piperazin-1-yl)-ethyl]-phenylamine, 184 mg of acetic acid 1-{2-[2-(4-

1,2-benzisothiazol-3-yl-piperazin-1-yl)-ethyl]-phenylcarbamoyl}-ethyl ester was isolated in 96% purity @ 254 nm; LCMS (APCI): 453 $[M+H]^+$.

Example 29

ACETIC ACID 1-{3-[2-(4-1,2-BENZISOTHIAZOL-3-YL-PIPERAZIN-1-YL)-ETHYL]-PHENYLCARBAMOYL}-ETHYL ESTER

Starting from 3-[2-(4-1,2-benzisothiazol-3-yl-piperazin-1-yl)-ethyl]-phenylamine, 198 mg of acetic acid 1-{3-[2-(4-1,2-benzisothiazol-3-yl-piperazin-1-yl)-ethyl]-phenylcarbamoyl}-ethyl ester was isolated in 91% purity @ 254 nm; LCMS (APCI): 453 $[M+H]^+$.

Example 30

ACETIC ACID 1-{4-[2-(4-1,2-BENZISOTHIAZOL-3-YL-PIPERAZIN-1-YL)-ETHYL]-PHENYLCARBAMOYL}-ETHYL ESTER

Starting from 4-[2-(4-1,2-benzisothiazol-3-yl-piperazin-1-yl)-ethyl]-phenylamine, 121 mg of acetic acid 1-{4-[2-(4-1,2-benzisothiazol-3-yl-piperazin-1-yl)-ethyl]-phenylcarbamoyl}-ethyl ester was isolated in 98% purity @ 254 nm; LCMS (APCI): 453 $[M+H]^+$.

Example 31

N-{2-[2-(4-1,2-BENZISOTHIAZOL-3-YL-PIPERAZIN-1-YL)-ETHYL]-PHENYL}-2-(2.5-DIMETHOXY-PHENYL)-ACETAMIDE

Starting from 2-[2-(4-1,2-benzisothiazol-3-yl-piperazin-1-yl)-ethyl]-phenylamine, 185 mg of N-{2-[2-(4-1,2-benzisothiazol-3-yl-piperazin-1-yl)-ethyl]-phenyl}-2-(2,5-dimethoxy-phenyl)-acetamide was isolated in 97% purity @ 254 nm; LCMS (APCI): 517 $[M+H]^+$.

Example 32

N-{3-[2-(4-1,2-BENZISOTHIAZOL-3-YL-PIPERAZIN-1-YL)-ETHYL]-PHENYL}-2-(2.5-DIMETHOXY-PHENYL)-ACETAMIDE

Starting from 3-[2-(4-1,2-benzisothiazol-3-yl-piperazin-1-yl)-ethyl]-phenylamine, 332 mg of N-{3-[2-(4-1,2-benzisothiazol-3-yl-piperazin-1-yl)-ethyl]-phenyl}-2-(2,5-dimethoxy-phenyl)-acetamide was isolated in 97% purity @ 254 nm; LCMS (APCI): 517 $[M+H]^+$.

Example 33

N-{4-[2-(4-1,2-BENZISOTHIAZOL-3-YL-PIPERAZIN-1-YL)-ETHYL]-PHENYL}-2-(2,5-DIMETHOXY-PHENYL)-ACETAMIDE

Starting from 4-[2-(4-1,2-benzisothiazol-3-yl-piperazin-1-yl)-ethyl]-phenylamine, 325 mg of N-{4-[2-(4-1,2-benzisothiazol-3-yl-piperazin-1-yl)-ethyl]-phenyl}-2-(2,5-dimethoxy-phenyl)-acetamide was isolated in 93% purity @ 254 nm; LCMS (APCI): 517 $[M+H]^+$.

Example 34

N-{2-[2-(4-1,2-BENZISOTHIAZOL-3-YL-PIPERAZIN-1-YL)-ETHYL]-PHENYL}-2-HYDROXY-PROPIONAMIDE

Starting from 2-[2-(4-1,2-benzisothiazol-3-yl-piperazin-1-yl)-ethyl]-phenylamine, 75 mg of N-{2-[2-(4-1,2-benzisothiazol-3-yl-piperazin-1-yl)-ethyl]-phenyl}-2-hydroxy-propionamide was isolated in 97% purity @ 254 nm; LCMS (APCI): 411 $[M+H]^+$.

Example 35

N-{3-[2-(4-1,2-BENZISOTHIAZOL-3-YL-PIPERAZIN-1-YL)-ETHYL]-PHENYL}-2-HYDROXY-PROPIONAMIDE

Starting from 3-[2-(4-1,2-benzisothiazol-3-yl-piperazin-1-yl)-ethyl]-phenylamine, 108 mg of N-{3-[2-(4-1,2-benzisothiazol-3-yl-piperazin-1-yl)-ethyl]-phenyl}-2-hydroxy-propionamide was isolated in 99% purity @ 254 nm; LCMS (APCI): 411 $[M+H]^+$.

Example 36

N-{4-[2-(4-1,2-BENZISOTHIAZOL-3-YL-PIPERAZIN-1-YL)-ETHYL]-PHENYL}-2-HYDROXY-PROPIONAMIDE

Starting from 4-[2-(4-1,2-benzisothiazol-3-yl-piperazin-1-yl)-ethyl]-phenylamine, 122 mg of N-{4-[2-(4-1,2-benzisothiazol-3-yl-piperazin-1-yl)-ethyl]-phenyl}-2-hydroxy-propionamide was isolated in 99% purity @ 254 nm; LCMS (APCI): 411 $[M+H]^+$.

Example 37

N-{4-[2-(4-1,2-BENZISOTHIAZOL-3-YL-PIPERAZIN-1-YL)-ETHYL]-PHENYL}-PROPIONAMIDE

Starting from 4-[2-(4-1,2-benzisothiazol-3-yl-piperazin-1-yl)-ethyl]-phenylamine, 135 mg of N-{4-[2-(4-1,2-benzisothiazol-3-yl-piperazin-1-yl)-ethyl]-phenyl}-propionamide was isolated in 100% purity @ 254 nm; MS (APCI): 395 $[M+H]^+$. Anal. Calcd for $C_{22}H_{26}N_4OS$: C, 66.98; H, 6.64; N, 14.20. Found: C, 66.72; H, 6.50; N, 14.10.

Example 38

N-{4-[2-(4-1,2-BENZISOTHIAZOL-3-YL-PIPERAZIN-1-YL)-ETHYL]-PHENYL}-2-PHENOXY-PROPIONAMIDE

Starting from 4-[2-(4-1,2-benzisothiazol-3-yl-piperazin-1-yl)-ethyl]-phenylamine, 224 mg of N-{4-[2-(4-1,2-benzisothiazol-3-yl-piperazin-1-yl)-ethyl]-phenyl}-2-phenoxy-propionamide was isolated; MS (APCI): 487 $[M+H]^+$. Anal. Calcd for $C_{28}H_{30}N_4O_2S$: C, 69.11; H, 6.21; N, 11.51. Found: C, 68.75; H, 6.20; N, 11.43.

Preparation 10

3-{4-[2-(4-NITRO-PHENOXY)-ETHYL]-PIPERAZIN-1-YL}-1,2-BENZISOTHIAZOLE

Excess dried, −325 mesh potassium carbonate (257 mg, 1.86 mmol) was diluted in 4 mL acetonitrile and 3-piperazin-1-yl-benzoisothiazole hydrochloride (395 mg, 1.55 mmol), catalytic potassium iodide, and 1(2-chloroethoxy)-4-nitrobenzene (250 mg, 1.20 mmol) were added. This mixture was sealed in a Smith microwave vial and heated on the Smith Workstation at 150° C. for 1.5 h. After cooling, the salts were filtered off and washed with acetonitrile and the filtrate was concentrated. The residue was taken up in methylene chloride and washed with water. The organic layer was dried over sodium sulfate, and concentrated to afford 530 mg of a yellow solid. Yield 89%; 92% HPLC purity at 214 nm; mp 115° C.; MS (APCI): 385 $[M+H]^+$.

Preparation 11

4-[2-(4-1,2-BENZISOTHIAZOL-3-YL-PIPERAZIN-1-YL)-ETHOXY]-PHENYLAMINE

4-[2-(4-1,2-Benzisothiazol-3-yl-piperazin-1-yl)-ethoxy]-phenylamine was prepared according to the general method as outlined in Preparation 3 starting from 3-{4-[2-(4-nitro-phenoxy)-ethyl]-piperazin-1-yl}-1,2-benzisothiazole (4.37 g, 11.4 mmol). The resultant white solid was dried in vacuo (3.83 g). Yield 95%; mp 128° C.; LCMS (APCI): 355 $[M+H]^+$.

The amides of Examples 39–43 were synthesized in combinatorial library format using appropriate acid chloride starting materials and 4-[2-(4-1,2-Benzisothiazol-3-yl-piperazin-1-yl)-ethoxy]-phenylamine on a 0.35 mmol scale and following the steps as outlined in Example 1. The crude products were dissolved in $CH_2Cl_2$ and purified by MPLC using a Biotage 40s prepacked silica gel cartridge and eluting with 3% methanol in methylene chloride.

Example 39

N-{4-[2-(4-1,2-BENZISOTHIAZOL-3-YL-PIPERAZIN-1-YL)-ETHOXY]-PHENYL}-2-(4-CHLORO-PHENYL)-ACETAMIDE 91 mg was isolated in 100% purity @ 254 nm; LCMS (APCI): 509 $[M+2H]^+$; mp 170° C.

Example 40

N-{4-[2-(4-1,2-BENZISOTHIAZOL-3-YL-PIPERAZIN-1-YL)-ETHOXY]-PHENYL}-PROPIONAMIDE 97 mg was isolated in 100% purity @ 254 nm; LCMS (APCI): 411 $[M+H]^+$.

Example 41

N-{4-[2-(4-1,2-BENZISOTHIAZOL-3-YL-PIPERAZIN-1-YL)-ETHOXY]-PHENYL}-2-THIOPHEN-2-YL-ACETAMIDE 74 mg was isolated in 100% purity @ 254 nm; LCMS (APCI): 479 $[M+H]^+$; mp 142° C.

Example 42

N-{4-[2-(4-1,2-BENZISOTHIAZOL-3-YL-PIPERAZIN-1-YL)-ETHOXY]-PHENYL}-2-(3-METHOXY-PHENYL)-ACETAMIDE 40 mg was isolated in 100% purity @ 254 nm; LCMS (APCI): 503 $[M+H]^+$.

Example 43

ACETIC ACID 1-{4-[2-(4-1,2-BENZISOTHIAZOL-3-YL-PIPERAZIN-1-YL)-ETHOXY]-PHENYLCARBAMOYL}-ETHYL ESTER 123 mg was isolated in 90% purity @ 254 nm; LCMS (APCI): 469 $[M+H]^+$; mp 90° C.

Example 44

1-METHYL-1H-IMIDAZOLE-4-SULFONIC ACID {4-[2-(4-1,2-BENZISOTHIAZOL-3-YL-PIPERAZIN-1-YL)-ETHOXY]-PHENYL}-AMIDE

4-[2-(4-1,2-Benzisothiazol-3-yl-piperazin-1-yl)-ethyl]-phenylamine (130 mg, 0.37 mmol) was dissolved in 2 mL pyridine and 1-methylimidazole-3-sulfonyl chloride (72 mg, 0.37 mmol) was added. The reaction mixtures were stirred at 40° C. overnight. Methylene chloride was added to the vial and the reaction mixture was washed with water. The organic layer was concentrated and evaluated by LCMS. The mixture was purified by MPLC using a Biotage 40s prepacked silica gel cartridge eluting with 3% methanol in methylene chloride. 1-Methyl-1H-imidazole-4-sulfonic acid {4-[2-(4-1,2-benzisothiazol-3-yl-piperazin-1-yl)-ethoxy]-phenyl}-amide (96 mg) was isolated in 100% purity @ 254 nm; LCMS (APCI): 499 $[M+H]^+$; mp 176° C.; $^1H$ NMR (400 MHz, $CDCl_3$) δ 8.14 (s, 1H), 7.87 (d, 1H), 7.79 (d, 1H), 7.48 (m, 2H), 7.32 (m, 1H), 7.18 (m, 2H), 6.77 (m, 2H), 4.10 (m, 2H), 3.62 (m, 4H), 3.58 (s, 3H), 2.88 (m, 6H).

The sulfonamides amides of Examples 45–49 were synthesized in combinatorial library format using appropriate sulfonyl chloride starting materials and 4-[2-(4-1,2-benzisothiazol-3-yl-piperazin-1-yl)-ethoxy]-phenylamine on a 0.37 mmol scale and following the steps as outlined in Example 44.

Example 45

5-CHLORO-1,3-DIMETHYL-1H-PYRAZOLE-4-SULFONIC ACID {4-[2-(4-1,2-BENZISOTHIAZOL-3-YL-PIPERAZIN-1-YL)-ETHOXY]-PHENYL}-AMIDE 117 mg was isolated in 100% purity @ 254 nm; LCMS (APCI): 547 $[M+H]^+$; mp 85° C.

Example 46

N-{4-[2-(4-1,2-BENZISOTHIAZOL-3-YL-PIPERAZIN-1-YL)-ETHOXY]-PHENYL}-2,5-DIMETHOXY-BENZENESULFONAMIDE 164 mg was isolated in 100% purity @ 254 nm; LCMS (APCI): 555 $[M+H]^+$; mp 78° C.

Example 47

N-{4-[2-(4-1,2-BENZISOTHIAZOL-3-YL-PIPERAZIN-1-YL)-ETHOXY]-PHENYL}-BENZENESULFONAMIDE 145 mg was isolated in 100% purity @ 254 nm; LCMS (APCI): 495 $[M+H]^+$; mp 65° C.

Example 48

1,2-DIMETHYL-1H-IMIDAZOLE-4-SULFONIC ACID {4-[2-(4-1,2-BENZISOTHIAZOL-3-YL-PIPERAZIN-1-YL)-ETHOXY]-PHENYL}-AMIDE 117 mg was isolated in 100% purity @ 254 nm; LCMS (APCI): 513 $[M+H]^+$; mp 227° C.

Example 49

N-(4-{4-[2-(4-1,2-BENZISOTHIAZOL-3-YL-PIPERAZIN-1-YL)-ETHOXY]-PHENYLSULFAMOYL}-PHENYL)-ACETAMIDE 62 mg was isolated in 100% purity @ 254 nm; LCMS (APCI): 552 $[M+H]^+$; mp 120° C.

Example 50

3-METHYL-BUT-2-ENOIC ACID {2-[2-(4-1,2-BENZISOTHIAZOL-3-YL-PIPERAZIN-1-YL)-ETHYL]-PHENYL}-AMIDE

Starting from 2-[2-(4-1,2-benzisothiazol-3-yl-piperazin-1-yl)-ethyl]-phenylamine (1 g, 2.82 mmol) and 3,3 dimethyl acryloyl chloride (0.33 mL, 2.97 mmol) and following the procedure as outlined in Example 1, 1.25 g of 3-methyl-but-2-enoic acid {2-[2-(4-1,2-benzisothiazol-3-yl-piperazin-1-yl)-ethyl]-phenyl}-amide was isolated as a white foam in 93% purity @ 214 nm; LCMS (APCI): 421 $[M+H]^+$; mp 52° C.

Preparation 12

1-(4-1,2-BENZISOTHIAZOL-3-YL-PIPERAZIN-1-YL)-2-(4,5-DIMETHOXY-2-NITRO-PHENYL)-ETHANONE 3-piperazin-1-yl-benzoisothiazole hydrochloride (5.29 g, 20.7 mmol) and 4,5-dimethoxy-2-nitrophenylacetic acid (5 g, 20.7 mmol) were combined in 200 mL methylene chloride with triethylamine (5.77 mL, 41.4 mmol). This solution stirred for 15 min before bis-(2-oxo-3-oxazolidinyl) phosphinic chloride (5.26 g, 20.7 mmol) was added. After stirring overnight at rt, the reaction was quenched with water and extracted into methylene chloride. The organic layer was washed with 0.5 N HCl, water, sodium bicarbonate then water before it was dried over $Na_2SO_4$ and concentrated. The residue was taken up in methylene chloride and washed with water. The organic layer was dried over sodium sulfate, and concentrated then purified by MPLC using a Biotage prepacked silica gel cartridge eluting with 3% methanol in methylene chloride to afford 6.5 g of a tan solid. Yield 71%; 100% purity at 214 nm; LCMS (APCI): 443 $[M+H]^+$; mp 170° C.

Preparation 13

3-{4-[2-(4,5-DIMETHOXY-2-NITRO-PHENYL)-ETHYL]-PIPERAZIN-1-YL}-1,2-BENZISOTHIAZOLE 1-(4-1,2-Benzisothiazol-3-yl-piperazin-1-yl)-2-(4,5-dimethoxy-2-nitro-phenyl)-ethanone (6.08 g, 13.8 mmol) was diluted in 50 mL of toulene. Borane methyl sulfide complex (2.0 M in tolulene, 7.22 mL) was slowly added to the stirring mixture. The reaction mixture was heated to 110° C. in an oil bath overnight. Upon cooling, excess sodium bicarbonate was added dropwise and the mixture was heated to 85° C. until gas evolution subsided. The water layer was removed and extracted in methylene chloride. The organic layers were combined, dried over $Na_2SO_4$ then concentrated and purified by column chromatography to afford 4.40 g of a brown solid. Yield 74%; 100% purity at 254 nm; LCMS (APCI): 428 $[M+H]^+$; mp 135° C.

Preparation 14

2-[2-(4-1,2-BENZISOTHIAZOL-3-YL-PIPERAZIN-1-YL)-ETHYL]-4,5-DIMETHOXY-PHENYLAMINE

2-[2-(4-1,2-Benzisothiazol-3-yl-piperazin-1-yl)-ethyl]-4,5-dimethoxy-phenylamine was prepared according to the general method as outlined in Preparation 3 starting from 3-{4-[2-(4,5-dimethoxy-2-nitro-phenyl)-ethyl]-piperazin-1-yl}-1,2-benzisothiazole (4.2 g, 9.8 mmol). The resultant tan solid was dried in vacuo (2.25 g). Yield 58%; mp 55° C.; 100% purity at 254 nm; LCMS (APCI): 399 $[M+H]^+$.

The amides of Examples 51–55 were synthesized in combinatorial library format using appropriate acid chloride starting materials and 2-[2-(4-1,2-benzisothiazol-3-yl-piperazin-1-yl)-ethyl]-4,5-dimethoxy-phenylamine on a 0.4 mmol scale and following the steps as outlined in Example 1. The crude products were dissolved in $CH_2Cl_2$ and purified by MPLC using a Biotage 40s prepacked silica gel cartridge and eluting with 3% methanol in methylene chloride.

Example 51

N-{2-[2-(4-1,2-BENZISOTHIAZOL-3-YL-PIPERAZIN-1-YL)-ETHYL]-4,5-DIMETHOXY-PHENYL}-ACETAMIDE 30 mg was isolated in 100% purity @ 254 nm; LCMS (APCI): 441 $[M+H]^+$; mp 120° C.

Example 52

N-{2-[2-(4-1,2-BENZISOTHIAZOL-3-YL-PIPERAZIN-1-YL)-ETHYL]-4,5-DIMETHOXY-PHENYL}-2-THIOPHEN-2-YL-ACETAMIDE 83 mg was isolated in 100% purity @ 254 nm; LCMS (APCI): 523 $[M+H]^+$; mp 135° C.

Example 53

N-{2-[2-(4-1,2-BENZISOTHIAZOL-3-YL-PIPERAZIN-1-YL)-ETHYL]-4,5-DIMETHOXY-PHENYL}-2-(4-CHLORO-PHENYL)-ACETAMIDE 121 mg was isolated in 100% purity @ 254 nm; LCMS (APCI): 551 [M]+; mp 152° C.

Example 54

N-{2-[2-(4-1,2-BENZISOTHIAZOL-3-YL-PIPERAZIN-1-YL)-ETHYL]-4,5-DIMETHOXY-PHENYL}-2.2-DIMETHYL-PROPIONAMIDE 38 mg was isolated in 100% purity @ 254 nm; LCMS (APCI): 483 $[M+H]^+$; mp 156° C.

Example 55

N-{2-[2-(4-1,2-BENZISOTHIAZOL-3-YL-PIPERAZIN-1-YL)-ETHYL]-4,5-DIMETHOXY-PHENYL}-2-PHENYL-ACETAMIDE 113 mg was isolated in 100% purity @ 254 nm; LCMS (APCI): 517 $[M+H]^+$; mp 142° C.

The sulfonamides of Examples 56–59 were synthesized in combinatorial library format using appropriate sulfonyl chloride starting materials and 2-[2-(4-1,2-benzisothiazol-3-yl-piperazin-1-yl)-ethyl]-4,5-dimethoxy-phenylamine on a 0.4 mmol scale and following the steps as outlined in Example 44. The crude products were dissolved in $CH_2Cl_2$ and purified by MPLC using a Biotage 40s prepacked silica gel cartridge and eluting with 3% methanol in methylene chloride.

Example 56

N-{2-[2-(4-1,2-BENZISOTHIAZOL-3-YL-PIPERAZIN-1-YL)-ETHYL]-4,5-DIMETHOXY-PHENYL}-2-FLUORO-BENZENESULFONAMIDE 148 mg was isolated in 100% purity @ 254 nm; MS (APCI): 557 $[M+H]^+$; mp 167° C.

Example 57

1,2-DIMETHYL-1H-IMIDAZOLE-4-SULFONIC ACID {2-[2-(4-1,2-BENZISOTHIAZOL-3-YL-PIPERAZIN-1-YL)-ETHYL]-4,5-DIMETHOXY-PHENYL}-AMIDE 155 mg was isolated in__ 100% purity @ 254 nm; LCMS (APCI): 557 $[M+H]^+$; mp 233° C.

Example 58

N-{2-[2-(4-1,2-BENZISOTHIAZOL-3-YL-PIPERAZIN-1-YL)-ETHYL]-4,5-DIMETHOXY-PHENYL}-2-METHYL-BENZENESULFONAMIDE 9 mg was isolated in 100% purity @ 254 nm; LCMS (APCI): 553 [M]+; mp 187° C.

Example 59

1,3,5-TRIMETHYL-1H-PYRAZOLE-4-SULFONIC ACID {2-[2-(4-1,2-BENZISOTHIAZOL-3-YL-PIPERAZIN-1-YL)-ETHYL]-4,5-DIMETHOXY-PHENYL}-AMIDE 174 mg was isolated in 100% purity @ 254 nm; LCMS (APCI): 571 $[M+H]^+$; mp 196° C.

Example 60

1-{2-[2-(4-1,2-BENZISOTHIAZOL-3-YL-PIPERAZIN-1-YL)-ETHYL]-4,5-DIMETHOXY-PHENYL}-3-O-TOLYL-UREA

2-[2-(4-1,2-Benzisothiazol-3-yl-piperazin-1-yl)-ethyl]-4,5-dimethoxy-phenylamine (160 mg, 0.4 mmol) was dissolved in 4 mL methylene chloride and 2-tolyl isocyanate (49 µL, 0.4 mmol) was added. The reaction mixtures were stirred at 40° C. overnight. Methylene chloride was added to the vial and the reaction mixture was washed with water. The product was recrystallized in isopropyl alcohol. 1-{2-[2-(4-1,2-Benzisothiazol-3-yl-piperazin-1-yl)-ethyl]-4,5-dimethoxy-phenyl}-3-o-tolyl-urea (168 mg) was isolated in 100% purity @ 254 nm; LCMS (APCI): 532 $[M+H]^+$; mp 200° C.; $^1H$ NMR (400 MHz, $CDCl_3$) δ 8.20 (s, 1H), 7.87 (d, J=8 Hz, 1H), 7.80 (m, 2H), 7.47 (t, 1H), 7.33 (t, 1H), 7.18 (t, 1H), 7.11 (m, 2H), 7.02 (t, 1H), 6.74 (s, 1H), 6.35 (s, 1H), 3.88 (s, 3H), 3.87 (s, 3H), 3.61 (t, 4H), 2.77 (m, 2H), 2.73 (m, 4H), 2.67 (m, 2H), 2.12 (s, 3H).

The sulfonamides of Examples 61–63 were synthesized in combinatorial library format using appropriate isocyanate starting materials and 2-[2-(4-1,2-benzisothiazol-3-yl-piperazin-1-yl)-ethyl]-4,5-dimethoxy-phenylamine on a 0.4 mmol scale and following the steps as outlined in Example 60. The crude products were recrystallized in isopropyl alcohol.

Example 61

1-{2-[2-(4-1,2-BENZISOTHIAZOL-3-YL-PIPERAZIN-1-YL)-ETHYL]-4,5-DIMETHOXY-PHENYL}-3-(2,6-DIMETHYL-PHENYL)-UREA 30 mg was isolated in 91% purity @ 214 nm; mp 96° C.; $^1H$ NMR (400 MHz, $CDCl_3$) δ 7.87 (d, J=8 Hz, 1H), 7.81 (d, J=8 Hz, 1H), 7.47 (t, 1H), 7.37 (t, 1H), 7.25 (s, 4H), 6.70 (s, 1H), 3.87(s, 3H), 3.86 (s, 3H), 3.55 (m, 4H), 2.64 (m, 8H), 2.33 (s, 6H).

Example 62

1-{2-[2-(4-1,2-BENZISOTHIAZOL-3-YL-PIPERAZIN-1-YL)-ETHYL]-4,5-DIMETHOXY-PHENYL}-3-(4-FLUORO-PHENYL)-UREA 141 mg was isolated in 94% purity @ 254 nm; LCMS (APCI): 536 $[M+H]^+$; mp 211° C.

Example 63

1-{2-[2-(4-1,2-BENZISOTHIAZOL-3-YL-PIPERAZIN-1-YL)-ETHYL]-4,5-DIMETHOXY-PHENYL}-3-CYCLOHEXYL-UREA 119 mg was isolated in 100% purity @ 254 nm; LCMS (APCI): 524 $[M+H]^+$; mp 156° C.

Preparation 15

(5-FLUORO-2-NITRO-PHENYL)-ACETIC ACID 3-methyl phenethyl alcohol (5 g, 36.7 mmol) was diluted in 30 mL of chloroform and ammonium nitrate (3.12 g, 38.9 mmol) was added. The reaction mixture was cooled to 0° C. and trifluoro acetic acid anhydride (16.02 mL, 113 mmol) was added dropwise. The reaction stirred at 0° C. for 3 hours before water was added to slowly quench the reaction. The chloroform layer was washed with water then collected and dried over $Na_2SO_4$ then concentrated. The desired isomer crystallized out of the crude solution in ethyl acetate and was then triturated with acetonitrile to afford 5.25 g of the desired isomer as a brown solid. Yield 87%; MS (APCI): 199 $[M-H]^-$.

Preparation 16

1-(4-1,2-BENZISOTHIAZOL-3-YL-PIPERAZIN-1-YL)-2-(5-FLUORO-2-NITRO-PHENYL)-ETHANONE 1-(4-1,2-Benzisothiazol-3-yl-piperazin-1-yl)-2-(5-fluoro-2-nitro-phenyl)-ethanone was prepared according to the general method as outlined in Preparation 12 starting from 3-piperazin-1-yl-benzoisothiazole hydrochloride (1.31 g, 5.1 mmol) and (5-fluoro-2-nitro-phenyl)-acetic acid (800 mg, 4.3 mmol). The product was isolated via column chromatography to afford 870 mg of an off white foam. Yield 50%; mp 72° C.; MS (APCI): 401 $[M+H]^+$.

Preparation 17

3-{4-[2-(5-FLUORO-2-NITRO-PHENYL)-ETHYL]-PIPERAZIN-1-YL}-1,2-BENZISOTHIAZOLE

3-{4-[2-(5-Fluoro-2-nitro-phenyl)-ethyl]-piperazin-1-yl}-1,2-benzisothiazole was prepared according to the general method as outlined in Preparation 13 starting from 1-(4-1,2-benzisothiazol-3-yl-piperazin-1-yl)-2-(5-fluoro-2-nitro-phenyl)-ethanone (870 mg, 2.18 mmol). The product was isolated via column chromatography and recrystallized in isopropyl alcohol to afford 411 mg of yellow crystals. Yield 49%; mp 131° C.; MS (APCI): 387 $[M+H]^+$.

Preparation 18

2-[2-(4-1,2-BENZISOTHIAZOL-3-YL-PIPERAZIN-1-YL)-ETHYL]-4-FLUORO-PHENYLAMINE

2-[2-(4-1,2-Benzisothiazol-3-yl-piperazin-1-yl)-ethyl]-4-fluoro-phenylamine was prepared according to the general method as outlined in Preparation 3 starting from 3-{4-[2-(5-fluoro-2-nitro-phenyl)-ethyl]-piperazin-1-yl}-1,2-benzisothiazole (2.27 g, 4.7 mmol). The product was isolated via column chromatography and recrystallized in isopropyl alcohol to afford 555 mg off white crystals. Yield 51%; mp 115° C.; MS (APCI): 357 $[M+H]^+$.

Example 64

3-METHYL-BUT-2-ENOIC ACID {2-[2-(4-1,2-BENZISOTHIAZOL-3-YL-PIPERAZIN-1-YL)-ETHYL]-4-FLUORO-PHENYL}-AMIDE

Starting from 2-[2-(4-1,2-benzisothiazol-3-yl-piperazin-1-yl)-ethyl]-4-fluoro-phenylamine (300 mg, 0.84 mmol) and 3,3 dimethyl acryloyl chloride (98 μL, 0.88 mmol) and following the procedure as outlined in Example 1, 287 mg of 3-methyl-but-2-enoic acid {2-[2-(4-1,2-benzisothiazol-3-yl-piperazin-1-yl)-ethyl]-4-fluoro-phenyl}-amide was isolated as a white powder in 100% purity @ 254 nm; LCMS (APCI): 439 $[M+H]^+$; mp 175° C.

Example 65

3-M ETHYL-BUT-2-ENOIC ACID {2-[2-(4-1,2-BENZISOTHIAZOL-3-YL-PIPERAZIN-1-YL)-ETHYL]-4,5-DIMETHOXY-PHENYL}-AMIDE

Starting from 2-[2-(4-1,2-benzisothiazol-3-yl-piperazin-1-yl)-ethyl]-4,5-dimethoxy phenylamine (300 mg, 0.75 mmol) and 3,3 dimethyl acryloyl chloride (87.7 μL, 0.79 mmol) and following the procedure as outlined in Example 1, 246 mg of 3-methyl-but-2-enoic acid {2-[2-(4-1,2-benzisothiazol-3-yl-piperazin-1-yl)-ethyl]-4,5-dimethoxy-phenyl}-amide was isolated as a white foam in 100% purity @ 254 nm; LCMS (APCI): 481 $[M+H]^+$; mp 58° C.

Preparation 19

{2-[2-(4-1,2-BENZISOTHIAZOL-3-YL-PIPERAZIN-1-YL)-ETHYL]-PHENYL}-METHYL-AMINE

2-[2-(4-1,2-Benzisothiazol-3-yl-piperazin-1-yl)-ethyl]-phenylamine (6.76 g, 20.0 mmol) was added to a suspension of sodium metal (2.3 g, 100 mmol) in methanol (30 mL) at rt. The resulting solution was then added to a suspension of paraformaldehyde (0.84 g) in methanol (20 mL). Suspension was warmed to reflux for 4 h. Reaction was cooled to room temperature followed by a careful quench with water (100 mL) and concentration of resulting suspension. The crude was diluted with water (100 mL) and extracted with methylene chloride (150 mL). The extract was dried over magnesium sulfate, filtered and concentrated to brown oil. The crude mixture was purified via medium pressure liquid chromatography using a 300 g silica gel Biotage cartridge eluting with a gradient of methylene chloride to (100:8:1) methylene choride: ethanol: ammonium hydroxide to yield pure {2-[2-(4-1,2-benzisothiazol-3-yl-piperazin-1-yl)-ethyl]-phenyl}-methyl-amine as an oil (3.73 g). Yield 53%; $^1H$ NMR (400 MHz, DMSO-$d_6$) δ 8.04 (d, J=8 Hz, 2H), 7.63 (d, J=8 Hz, 2H), 7.53 (t, J=7 Hz, 1H), 7.40 (t, J=8 Hz, 1H), 7.00 (t, J=9 Hz, 1H), 6.93 (d, J=7 Hz, 1H), 6.50 (t, J=8 Hz, 1H), 6.45 (d, J=8 Hz, 1H), 5.40 (m, 1H), 3.44 (t, J=5 Hz, 4H), 2.66 (m, 9H), 2.47(t, J=2 Hz, 2H).

Example 66

3-METHYL-BUT-2-ENOIC ACID {2-[2-(4-1,2-BENZISOTHIAZOL-3-YL-PIPERAZIN-1-YL)-ETHYL]-PHENYL}-METHYL-AMIDE

Starting from {2-[2-(4-1,2-benzisothiazol-3-yl-piperazin-1-yl)-ethyl]-phenyl}-methyl-amine (300 mg, 0.84 mmol) and 3,3 dimethyl acryloyl chloride (97 μL, 0.88 mmol) and following the procedure as outlined in Example 1, 403 mg of 3-methyl-but-2-enoic acid {2-[2-(4-1,2-benzisothiazol-3-yl-piperazin-1-yl)-ethyl]-phenyl}-methyl-amide was isolated as a low melting solid in 100% purity @ 254 nm; LCMS (APCI): 435 $[M+H]^+$.

Example 67

N-{2-[2-(4-1,2-BENZISOTHIAZOL-3-YL-PIPERAZIN-1-YL)-ETHYL]-4-FLUORO-PHENYL}-ACETAMIDE

Starting from 2-[2-(4-1,2-benzisothiazol-3-yl-piperazin-1-yl)-ethyl]-4-fluoro-phenylamine (142 mg, 0.4 mmol) and acetyl chloride (32.7 μL, 0.4 mmol) and following the procedure as outlined in Example 1, 41 mg of N-{2-[2-(4-1,2-benzisothiazol-3-yl-piperazin-1-yl)-ethyl]-4-fluoro-phenyl}-acetamide was isolated as a yellow foam in 100% purity @ 254 nm; LCMS (APCI): 399 $[M+H]^+$.

Example 68

1-{2-[2-(4-1,2-BENZISOTHIAZOL-3-YL-PIPERAZIN-1-YL)-ETHYL]-4-FLUORO-PHENYL}-3-O-TOLYL-UREA

Starting from 2-[2-(4-1,2-benzisothiazol-3-yl-piperazin-1-yl)-ethyl]-4-fluoro-phenylamine (142 mg, 0.4 mmol) and 2-tolyl isocyanate (57 μL, 0.4 mmol) and following the procedure as outlined in Example 60, 140 mg of 1-{2-[2-(4-1,2-benzisothiazol-3-yl-piperazin-1-yl)-ethyl]-4-fluoro-phenyl}-3-o-tolyl-urea was isolated as an off white powder in 98% purity @ 214 nm; LCMS (APCI): 490 $[M+H]^+$.

Example 69

1-{2-[2-(4-1,2-BENZISOTHIAZOL-3-YL-PIPERAZIN-1-YL)-ETHYL]-4-FLUORO-PHENYL}-3-(2-CHLORO-PHENYL)-UREA

Starting from 2-[2-(4-1,2-benzisothiazol-3-yl-piperazin-1-yl)-ethyl]-4-fluoro-phenylamine (142 mg, 0.4 mmol) and 2-chlorophenyl isocyanate (56 μL, 0.4 mmol) and following the procedure as outlined in Example 60, 120 mg of 1-{2-[2-(4-1,2-benzisothiazol-3-yl-piperazin-1-yl)-ethyl]-4-fluoro-phenyl}-3-(2-chloro-phenyl)-urea was isolated as an off white powder in 100% purity @ 254 nm; LCMS (APCI): 508 $[M-2H]^-$.

Preparation 20

4-[2-(4-1,2-BENZISOTHIAZOL-3-YL-PIPERAZIN-1-YL)-ETHYL]-2-BROMO-PHENYLAMINE

To a 2 dram vial was added 0.20 g (0.6 mmol) 4-[2-(4-1,2-benzisothiazol-3-yl-piperazin-1-yl)-ethyl]-phenylamine, 6.0 mL $CH_2Cl_2$, and 104 mg (0.6 mmol) N-bromosuccinimide. The reaction was stirred for 30 min at rt and then quenched with 1 M $Na_2SO_3$. The organic layer was separated, dried, and concentrated in vacuo. The deep red product was purified by MPLC to give 0.059 g (24% yield) of a clear, tacky liquid. MS (APCI): 419 $[M+H]^+$.

Example 70

N-{4-[2-(4-1,2-BENZISOTHIAZOL-3-YL-PIPERAZIN-1-YL)-ETHYL]-2-BROMO-PHENYL}-ACETAMIDE

A 2 dram vial was charged with 0.09 g (0.2 mmol) of 4-[2-(4-1,2-benzisothiazol-3-yl-piperazin-1-yl)-ethyl]-2-bromo-phenylamine and 0.87 mL $CH_2Cl_2$. This mixture was treated with 36 μL triethylamine (0.26 mmol) and 17 μL acetyl chloride and stirred at rt for 15 h. The reaction was quenched with aqueous 1M $NaHCO_3$, the organic layer separated, dried, and concentrated in vacuo. This gave a quantitative yield of the desired product as a white solid. MS (APCI): 461 $[M+H]^+$. $^1H$ NMR (400 MHz, $CDCl_3$) δ 7.89 (d, J=8 Hz, 1H), 7.77 (d, J=8 Hz, 1H), 7.43 (t, J=7.5 Hz, 1H), 7.32 (t, J=7.5 Hz, 1H), 7.26 (s, 1H), 6.95–6.93 (m, 1H), 6.7 (d, J=8 Hz, 1H), 3.98 (br s, 2H), 3.57–3.55 (m, 4H), 2.72–2.58 (m, 8H).

Example 71

N-{4-[2-(4-1,2-BENZISOTHIAZOL-3-YL-PIPERAZIN-1-YL)-ETHYL]-PHENYL}-ACETAMIDE

A round bottomed flask was charged with 0.528 g (1.5 mmol) (0.2-[2-(4-1,2-benzisothiazol-3-yl-piperazin-1-yl)-ethyl]-phenylamine, 6.2 mL $CH_2Cl_2$, 0.26 mL (1.8 mmol) triethylamine, and 0.15 mL (2 mmol) acetyl chloride. After 17 h at rt, the reaction was quenched with 1M NaHCO3. The organic layer was separated, dried, and concentrated in vacuo to give a white foam. This white foam was triturated with ether to give 0.36 g (61% yield) of the desired material as a white solid. MS (APCI): 381 $[M+H]^+$. $^1H$ NMR (400 MHz, $CDCl_3$) δ 7.89 (d, J=8 Hz, 1H), 7.9 (d, J=8 Hz, 1H), 7.47–7.24 (m, 4H), 7.18–7.14 (m, 3H), 3.59–3.56 (m, 4H), 2.84–2.63 (m, 8H), 2.15 (s, 3H).

Preparation 21

{2-[2-(4-1,2-BENZISOTHIAZOL-3-YL-PIPERAZIN-1-YL)-ETHYL]-PHENYL}-ISOPROPYL-AMINE

A round bottomed flask was charged with 4.9 g (0.015 mol) 2-[2-(4-1,2-Benzisothiazol-3-yl-piperazin-1-yl)-ethyl]-phenylamine, 50 mL $ClCH_2CH_2Cl$, 1.2 mL (0.016 mol) acetone, 0.93 mL (0.016 mol) HOAc, and 5.2 g (0.024 mol) $NaBH(OAc)_3$. After stirring for 15 h at rt the reaction was quenched with 50 mL 2M $K_2CO_3$. The organic layer was separated, dried and concentrated in vacuo to give 5.5 g (100% yield) of the desired material as a yellow-orange oil. MS (APCI): 381 $[M+H]^+$. $^1H$ NMR (400 MHz, $CDCl_3$) δ 7.90 (d, J=8 Hz, 1H), 7.70 (d, J=8 Hz, 1H), 7.47–7.42 (m, 1H), 7.35–7.31 (m, 1H), 7.03–7.00 (m, 2H), 6.54–6.50 (m, 2H), 3.61–3.55 (m, 5H), 2.75–2.71 (m, 6H), 2.65–2.60 (m, 2H), 1.18 (d, J=6 Hz, 6H).

Preparation 22

3-METHYL-2-NITROBENZYL BROMIDE

A round bottomed flask was charged with 5.0 g (0.029 mol) of 3-methyl-2-nitrobenzyl alcohol and 100 mL of anhydrous acetonitrile. The reaction solution was cooled to 0° C. and treated, portionwise, with 13.2 g (0.031 mol) triphenylphosphine perbromide ($Ph_3P—Br_2$). The reaction was allowed to warm to rt overnight at which point the solvent was removed and the resulting solids triturated with 50:50 ether:hexanes. The wash solvent was filtered through a fine frit and then concentrated to give a quantitative yield (7.03 g) of the desired material as a white solid. $^1H$ NMR (400 MHz, $CDCl_3$) δ 7.36–7.34 (m, 2H), 7.33–7.24 (m, 1H), 4.45 (s, 2H), 2.33 (s, 3H).

Preparation 23

3-METHYL-2-NITROBENZYL CYANIDE

A round bottomed flask was charged with 6.51 g (0.028 mol) of 3-methyl-2nitrobenzyl bromide, 120 mL 1:1 EtOH:$H_2O$, and 5.5 g KCN (0.084 mol). The reaction solution was heated to 60° C. for 2 h. The reaction was cooled and the volatiles removed in vacuo. The resulting solid was dissolved in 150 mL water and extracted with 300 mL ethyl acetate. The organic extracts were washed with brine, dried over $MgSO_4$, filtered, and concentrated. This gave 4.63 g (92% yield) of the desired material as a slightly yellow solid. $^1H$ NMR (400 MHz, $CDCl_3$) δ 7.45–7.41 (m, 2H), 7.33–7.31 (m,1H), 3.77 (s, 2H), 2.36 (s, 3H).

Preparation 24

3-METHYL-2-NITRO-PHENYLACETIC ACID

A 2 dram vial was charged with 0.1 g (0.5 mmol) 3-methyl-2-nitrobenzyl cyanide and 0.4 mL $H_2O$. To this reaction slurry was added, dropwise with stirring, 0.5 mL concentrated HCl followed by 50 drops of HOAc. The reaction mixture was then heated to 90° C. for 5 h. Upon cooling of the solution a white ppt formed. This white ppt was filtered, washed with water, and dried to give 0.076 g (70% yield) of light yellow crystals. MS (APCI): 195 $[M-H]^-$.

Preparation 25

3-METHYL-2-NITRO-PHENETHYL ALCOHOL

A round bottomed flask was charged with 1.2 g (6 mmol) 3-methyl-2-nitro-phenylacetic acid and 24 mL anhydrous THF. The reaction was cooled to 0° C. and then treated with 4.0 mL 2M $BH_3$-DMS in THF (7.8 mmol) over 5 m. The reaction was allowed to warm to rt overnight. The volatile solvents were removed in vacuo and the resulting material was partitioned between EtOAc/1 M $NaHCO_3$. The organic extracts were washed with brine, dried over $MgSO_4$, filtered, and concentrated in vacuo to give 1.06 g (95% yield) as a light, orange oil. $^1H$ NMR (400 MHz, $CDCl_3$) δ 7.32–7.16 (m, 3H), 3.84 (t, J=6.4 Hz, 2H), 2.81 (t, J=6.4 Hz, 2H), 2.30 (s, 3H).

Preparation 26

3-METHYL-2-NITRO PHENETHYL TOSYLATE

3-Methyl-2-nitrophenethyl tosylate was prepared according to the general method as outlined in Preparation 1 starting from 3-methyl-2-nitrophenethyl alcohol (1.06 g, 5.86 mmol) and tosyl chloride (1.34 g, 7 mmol). 2 g product was taken crude to the next step. Yield 100%; $^1H$ NMR (400 MHz, $CDCl_3$) δ 7.68 (d, 2H), 7.29 (m, 3H), 7.17 (t, 2H), 4.23 (t, J=6 Hz, 2H), 2.89 (t, J=6 Hz, 2H), 2.42 (s, 3H), 2.27 (s, 3H).

Preparation 27

3-{4-[2-(3-METHYL-2-NITRO-PHENYL)-ETHYL]-PIPERAZIN-1-YL}-1,2-BENZISOTHIAZOLE

3-{4-[2-(3-Methyl-2-nitro-phenyl)-ethyl]-piperazin-1-yl}-1,2-benzisothiazole was prepared according to the general method as outlined in Preparation 2 starting with 3-piperazin-1-yl-benzoisothiazole hydrochloride (1.71 g, 6.7 mmol) and 3-methyl-2-nitrophenethyl tosylate (1.8 g, 5.37 mmol). The product was isolated via column chromatography to afford 290 mg of brown oil. Yield 11%; MS (APCI): 383 $[M+H]^+$.

Preparation 28

2-[2-(4-1,2-BENZISOTHIAZOL-3-YL-PIPERAZIN-1-YL)-ETHYL]-6-METHYL-PHENYLAMINE

2-[2-(4-1,2-Benzisothiazol-3-yl-piperazin-1-yl)-ethyl]-6-methyl-phenylamine was prepared according to the general method as outlined in Preparation 3 starting from 3-{4-[2-(3-methyl-2-nitro-phenyl)-ethyl]-piperazin-1-yl}-1,2-benzisothiazole (290 mg, 0.76 mmol). The product was purified via column chromatography and isolated as a yellow oil (65 mg).

Yield 24%; MS (APCI): 353 $[M+H]^+$.

Example 72

N-{2-[2-(4-1,2-BENZISOTHIAZOL-3-YL-PIPERAZIN-1-YL)-ETHYL]-6-METHYL-PHENYL}-ACETAMIDE

Starting from 2-[2-(4-1,2-benzisothiazol-3-yl-piperazin-1-yl)-ethyl]-6-methyl-phenylamine (65 mg, 0.185 mmol) and acetyl chloride (14 µL, 0.194 mmol) and following the procedure as outlined in Example 1, 46 mg of N-{2-[2-(4-1,2-benzisothiazol-3-yl-piperazin-1-yl)-ethyl]-6-methyl-phenyl}-acetamide was isolated as a pink foam in 100% purity @ 254 nm; LCMS (APCI): 395 $[M+H]^+$.

Example 73

3-METHYL-BUT-2-ENOIC ACID {3-[2-(4-1,2-BENZISOTHIAZOL-3-YL-PIPERAZIN-1-YL)-ETHYL]-PHENYL}-AMIDE

Starting from {3-[2-(4-1,2-benzisothiazol-3-yl-piperazin-1-yl)-ethyl]-phenyl}-amine (338 mg, 1 mmol) and 3,3 dimethyl acryloyl chloride (116 µL, 1.05 mmol) and following the procedure as outlined in Example 1, 406 mg of 3-methyl-but-2-enoic acid {3-[2-(4-1,2-benzisothiazol-3-yl-piperazin-1-yl)-ethyl]-phenyl}-amide was isolated as a light yellow solid in 100% purity @ 254 nm; LCMS (APCI): 421 $[M+H]^+$.

Preparation 29

1-(3-BROMO-PROPYL)-2-NITRO-BENZENE AND 1-(3-BROMO-PROPYL)-4-NITRO-BENZENE (3-Bromo-propyl)-benzene (10 g) was dissolved in 60 mL methylene chloride. Ammonium nitrate (4.78 g) and trifluoroacetic acid (90.4 mL) was added slowly. The reaction was stirred at rt for 4 h and was concentrated. The residue was dissolved in water and stirred overnight. The water was decanted off. The oil was dissolved in ethyl acetate and washed with water and sat. NaCl. The organic layer was dried over sodium sulfate and concentrated. The residue was purified using an ISCO autocolumn eluting with 80% ethyl acetate in hexanes to afford a mixture of ortho and para isomers. Yield 65%; $^1H$ NMR (400 MHz, $CDCl_3$) δ 8.05 (d, J=8 Hz, 2H), 7.82 (d, J=8.0 Hz, 1H), 7.46 (d, J=7.5 Hz, 1H), 7.29 (m, 4H), 3.36 (t, J=6.59, 2H), 3.31 (t, J=6.59, 6.34 Hz, 2H), 2.94 (t, J=8.05, 7.08 Hz, 2H), 2.81 (t, J=7.81, 7.07 Hz, 2H), 2.09 (m, 4H).

Preparation 30

3-{4-[3-(2-NITRO-PHENYL)-PROPYL]-PIPERAZIN-1-YL}-1,2-BENZOISOTHIAZOLE AND 3-{4-[3-(4-NITRO-PHENYL)-PROPYL]-PIPERAZIN-1-YL}-1,2-BENZOISOTHIAZOLE

Excess dried, −325 mesh potassium carbonate (5.1 g) was diluted in 100 mL acetone. The mixture of ortho and para isomers of 1-(3-bromo-propyl)-2-nitro-benzene (6.0 g, 24.6 mmol) and 3-piperazin-1-yl-benzoisothiazole (6.47 g, 29.5 mmol) was added. The mixture stirred at reflux for 72 h. After cooling, the mixture was diluted in ethyl acetate and washed with water. The organic layer was dried over sodium sulfate, and concentrated. The residue was purified and isomers separated using an ISCO autocolumn eluting with 80% ethyl acetate in hexanes to afford each isomer. Yield 39%; MS (APCI): 383 $[M+H]^+$.

Preparation 31

2-[3-(4-1,2-BENZISOTHIAZOL-3-YL-PIPERAZIN-1-YL)-PROPYL]-PHENYLAMINE

3-{4-[3-(2-Nitro-phenyl)-propyl]-piperazin-1-yl}-1,2-benzoisothiazole (3.25 g, 8.5 mmol) was dissolved in 100 mL of THF treated with triethylamine (0.3 ml) and with wet Raney nickel (1.02 g). The resulting mixture was placed on a shaker type hydrogenator, purged with hydrogen, pressurized (29.8 psig) and shaken at room temperature for 16 hours. The resulting mixture was filtered to remove the catalyst then filtered a second time over celite before the filtrate was concentrated. The resultant solid was dried in vacuo (2.33 g, 6.61 mmol). Yield 78%; MS (APCI): 352 $[M+H]^+$.

Example 74

N-(2-[3-(4-1,2-BENZOISOTHIZOL-3-YL-PIPERAZIN-1-YL)-PROPYL]-PHENYL}-2-(3-METHOXY-PHENYL)-ACETAMIDE

Starting from 2-[3-(4-1,2-benzisothiazol-3-yl-piperazin-1-yl)-propyl]-phenylamine (200 mg) and 3-methoxyphenylacetyl chloride (0.088 mL) and following the procedure outlined in Example 1, 72 mg of N-(2-[3-(4-1,2-benzoisothizol-3-yl-piperazin-1-yl)-propyl]-phenyl}-2-(3-methoxyphenyl)-acetamide_was isolated in 100% purity @ 254 nm; LCMS (APCI): 501 $[M+H]^+$.

Example 75

N-{2-[3-(4,12-BENZOISOTHIAZOL-3-YL-PIPERAZIN-1-YL)-PROPYL]-PHENYL}-2-(4-CHLORO-PHENYL)-ACETAMIDE

N-{2-[3-(4,1,2-Benzoisothiazol-3-yl-piperazin-1-yl)-propyl]-phenyl}-2-(4-chloro-phenyl)-acetamide was prepared according to the procedure outlined in Example 1, starting with 2-[3-(4-1,2-benzisothiazol-3-yl-piperazin-1-yl)-propyl]-phenylamine (200 mg) and 4-(chloromethyl)benzoyl chloride (107 mg). The resultant white solid was purified using an ISCO autocolumn eluting with 80% ethyl acetate in hexanes. N-{2-[3-(4,1,2-Benzoisothiazol-3-yl-piperazin-1-yl)-propyl]-phenyl}-2-(4-chloro-phenyl)-acetamide was isolated in 100% purity @ 254 nm; LCMS (APCI): 505 $[M+H]^+$.

Example 76

N-{2-[3-(4-1,2-BENZOISOTHIAZOL-3-YL-PIPERAZIN-1-YL)-PROPYL]-PHENYL}-2-THIOPHEN-2-YL-ACETAMIDE

N-{2-[3-(4-1,2-Benzoisothiazol-3-yl-piperazin-1-yl)-propyl]-phenyl}-2-thiophen-2-yl-acetamide was prepared according to the procedure outlined in Example 1, starting with 2-[3-(4-1,2-benzisothiazol-3-yl-piperazin-1-yl)-propyl]-phenylamine (200 mg) and 2-thiopheneacetyl chloride (0.069 mL). The resultant white solid was purified using an ISCO autocolumn eluting with 80% ethyl acetate in hexanes. N-{2-[3-(4,1,2-Benzoisothiazol-3-yl-piperazin-1-yl)-propyl]-phenyl}-2-(4-chloro-phenyl)-acetamide was isolated in 100% purity @ 254 nm; LCMS (APCI): 477 $[M+H]^+$.

Example 77

N-{2-[3-(4-1,2-BENZISOTHIAZOL-3-YL-PIPERAZIN-1-YL)-PROPYL]-PHENYL}-2-FLUORO-BENZENESULFONAMIDE

N-{2-[3-(4-1,2-Benzisothiazol-3-yl-piperazin-1-yl)-propyl]-phenyl}-2-fluoro-benzenesulfonamide was prepared according to the procedure outlined in Example 44, starting with 2-[3-(4-1,2-benzisothiazol-3-yl-piperazin-1-yl)-propyl]-phenylamine (150 mg) and 2-fluorobenzenesulfonyl chloride (55 mg). The resultant white solid was purified using an ISCO autocolumn eluting with 100% ethyl acetate. N-{2-[3-(4-1,2-Benzisothiazol-3-yl-piperazin-1-yl)-propyl]-phenyl}-2-fluoro-benzenesulfonamide was isolated in 100% purity @ 254 nm; LCMS (APCI): 511 $[M+H]^+$.

Example 78

1,2-DIMETHYL-1H-IMIDAZOLE-4-SULFONIC ACID {2-[3-(4-1,2-BENZISOTHIAZOL-3-YL-PIPERAZIN-1-YL)-PROPYL]-PHENYL}-AMIDE 1,2-Dimethyl-1H-imidazole-4-sulfonic acid {2-[3-(4-1,2-benzisothiazol-3-yl-piperazin-1-yl)-propyl]-phenyl}-amide was prepared according to the procedure outlined in Example 44, starting with 2-[3-(4-1,2-benzisothiazol-3-yl-piperazin-1-yl)-propyl]-phenylamine (150 mg) and 1,2-dimethylbenzenesulfonyl chloride (55 mg). The resultant white solid was purified using an ISCO autocolumn eluting with 100% ethyl acetate to afford N-{2-[3-(4-1,2-benzisothiazol-3-yl-piperazin-1-yl)-propyl]-phenyl}-2-fluoro-benzenesulfonamide. MS (APCI): 511 $[M+H]^+$.

Example 79

1-{2-[3-(4-1,2-BENZISOTHIAZOL-3-YL-PIPERAZIN-1-YL)-PROPYL]-PHENYL}-3-(2,6-DIMETHYL-PHENYL)-UREA

1-{2-[3-(4-1,2-Benzisothiazol-3-yl-piperazin-1-yl)-propyl]-phenyl}-3-(2,6-dimethyl-phenyl)-urea was prepared according to the procedure outlined in Example 60, starting with 2-[3-(4-1,2-benzisothiazol-3-yl-piperazin-1-yl)-propyl]-phenylamine (100 mg) and 2,6-dimethylphenyl isocyanate (0.040 mL). The resultant white solid was recrystallized using isopropyl alcohol. 1-{2-[3-(4-1,2-benzisothiazol-3-yl-piperazin-1-yl)-propyl]-phenyl}-3-(2,6- dimethyl-phenyl)-urea was isolated in 100% purity @ 254 nm; LCMS (APCI): 500 $[M+H]^+$.

Example 80

1-{2-[3-(4-1,2-BENZISOTHIAZOL-3-YL-PIPERAZIN-1-YL)-PROPYL]-PHENYL}-3-PROPYL-UREA

1-{2-[3-(4-1,2-Benzisothiazol-3-yl-piperazin-1-yl)-propyl]-phenyl}-3-propyl-urea was prepared according to the procedure outlined in Example 60, starting with 2-[3-(4-1,2-benzisothiazol-3-yl-piperazin-1-yl)-propyl]-phenylamine (100 mg) and isopropyl isocyanate (0.026 mL). The resultant white solid was recrystallized using isopropyl alcohol. 1-{2-[3-(4-1,2-Benzisothiazol-3-yl-piperazin-1-yl)-propyl]-phenyl}-3-propyl-urea was isolated in 100% purity @ 254 nm; LCMS (APCI): 438 $[M+H]^+$.

Preparation 32

4-[3-(4-1,2-BENZISOTHIAZOL-3-YL-PIPERAZIN-1-YL)-PROPYL]-PHENYLAMINE

4-[3-(4-1,2-Benzisothiazol-3-yl-piperazin-1-yl)-propyl]-phenylamine was prepared according to the general method as outlined in Preparation 3 starting from 3-{4-[3-(4-nitro-phenyl)-propyl]-piperazin-1-yl}-1,2-benzoisothiazole (0.58 g, 1.52 mmol), 50 mL of THF treated with triethylamine (0.3 mL) and wet Raney nickel (0.56 g). The resultant solid was dried in vacuo (0.535 g, 1.52 mmol). Yield 100%; MS (APCI): 353 $[M+H]^+$.

Example 81

N-(4-[3-(4-1,2-BENZOISOTHIZOL-3-YL-PIPERAZIN-1-YL)-PROPYL]-PHENYL}-2-(3-METHOXY-PHENYL)-ACETAMIDE

Starting from 4-[3-(4-1,2-Benzisothiazol-3-yl-piperazin-1-yl)-propyl]-phenylamine (200 mg) and 3-methoxyphenylacetyl chloride (0.088 mL) and following the procedure outlined in Example 1, 166 mg of N-(4-[3-(4-1,2-benzoisothizol-3-yl-piperazin-1-yl)-propyl]-phenyl}-2-(3-methoxy-phenyl)-acetamide_was isolated in 100% purity @ 254 nm; LCMS (APCI): 501 $[M+H]^+$.

Example 82

N-{4-[3-(4,1,2-BENZOISOTHIAZOL-3-YL-PIPERAZIN-1-YL)-PROPYL]-PHENYL}-2-(4-CHLORO-PHENYL)-ACETAMIDE

N-{4-[3-(4,1,2-Benzoisothiazol-3-yl-piperazin-1-yl)-propyl]-phenyl}-2-(4-chloro-phenyl)-acetamide was prepared according to the procedure outlined in Example 1, starting with 4-[3-(4-1,2-benzisothiazol-3-yl-piperazin-1-yl)-propyl]-phenylamine (220 mg) and 4-(chloromethyl)benzoyl chloride (107 mg). The resultant white solid was purified using an ISCO autocolumn eluting with 80% ethyl acetate in hexanes. N-{2-[3-(4,1,2-Benzoisothiazol-3-yl-piperazin-1-yl)-propyl]-phenyl}-2-(4-chloro-phenyl)-acetamide was isolated in 100% purity @ 254 nm; LCMS (APCI): 505 $[M+H]^+$.

Example 83

N-{4-[3-(4-1,2-BENZOISOTHIAZOL-3-YL-PIPERAZIN-1-YL)-PROPYL]-PHENYL}-2-THIOPHEN-2-YL-ACETAMIDE

N-{4-[3-(4-1,2-Benzoisothiazol-3-yl-piperazin-1-yl)-propyl]-phenyl}-2-thiophen-2-yl-acetamide was prepared according to the procedure outlined in Example 1, starting with 4-[3-(4-1,2-benzisothiazol-3-yl-piperazin-1-yl)-propyl]-phenylamine (200 mg) and 2-thiopheneacetyl chloride (0.069 mL). The resultant white solid was purified using an ISCO autocolumn eluting with 80% ethyl acetate in hexanes. N-{2-[3-(4,1,2-Benzoisothiazol-3-yl-piperazin-1-yl)-propyl]-phenyl}-2-(4-chloro-phenyl)-acetamide was isolated in 100% purity @ 254 nm; LCMS (APCI): 477 $[M+H]^+$.

Example 84

N-{4-[3-(4-1,2-BENZISOTHIAZOL-3-YL-PIPERAZIN-1-YL)-PROPYL]-PHENYL}-2-FLUORO-BENZENESULFONAMIDE

N-{4-[3-(4-1,2-Benzisothiazol-3-yl-piperazin-1-yl)-propyl]-phenyl}-2-fluoro-benzenesulfonamide was prepared according to the procedure outlined in Example 44 starting with 4-[3-(4-1,2-benzisothiazol-3-yl-piperazin-1-yl)-propyl]-phenylamine (100 mg) and 2-fluorobenzenesulfonyl chloride (55 mg). The resultant white solid was purified using an ISCO autocolumn eluting with 100% ethyl acetate to afford N-{4-[3-(4-1,2-benzisothiazol-3-yl-piperazin-1-yl)-propyl]-phenyl}-2-fluoro-benzenesulfonamide. MS (APCI): 511 $[M+H]^+$.

Example 85

N-{4-[2-(4-1,2-BENZISOTHIAZOL-3-YL-PIPERAZIN-1-YL)-ETHYL]-PHENYL}-ACETAMIDE

4-[2-(4-Benzo[d]isothiazol-3-yl-piperazin-1-yl)-ethyl]-phenylamine was diluted to 0.20 M with anhydrous dichloromethane, then delivered to an 8 mL vial via pipette (0.20 mmol). To the amine solution was added base (0.4 M triethylamine in dichloromethane, 0.40 mmol). Isoxazole-5-carbonyl chloride was diluted to 0.20 M with dichloromethane, and added at rt (0.40 mmol). The solution was shaken overnight at rt. Polyamine scavenging resin was added (0.5 mmol). The solution was shaken overnight at rt, then filtered into an 8 mL vial. The filtrate was evaluated by MS, then concentrated using an HT-12 GeneVac. Crude was purified by HPLC (30×100 mm ODS-A C(18) 5u column). 4-[2-(4-Benzo[d]isothiazol-3-yl-piperazin-1-yl)-ethyl]-phenylamine was isolated in 94.5% purity @ 254 nm, LCMS (APCI): 434 $[M+H]^+$.

The amides of Examples 86–202 were synthesized in combinatorial library format following the steps outlined in Example 85 on a 0.15–0.25 mmol scale using 4-[2-(4-benzo[d]isothiazol-3-yl-piperazin-1-yl)-ethyl]-phenylamine, 3-[2-(4-benzo[d]isothiazol-3-yl-piperazin-1-yl)-ethyl]-phenylamine, or 2-[2-(4-benzo[d]isothiazol-3-yl-piperazin-1-yl)-ethyl]-phenylamine with appropriate acid chloride starting materials and N-methylmorpholine on polystyrene resin or triethylamine. The crude products were purified by HPLC (30×100 mm ODS-A C(18) 5u column).

Example 86

N-{4-[2-(4-1,2-BENZISOTHIAZOL-3-YL-PIPERAZIN-1-YL)-ETHYL]-PHENYL}-3-METHOXY-BENZAMIDE

Isolated in 100% purity @ 254 nm; LCMS (APCI): 473 [M+H]+

Example 87

N-{4-[2-(4-1,2-BENZISOTHIAZOL-3-YL-PIPERAZIN-1-YL)-ETHYL]-PHENYL}-BUTYRAMIDE

Isolated in 100% purity @ 254 nm; LCMS (APCI): 409 $[M+H]^+$

Example 88

THIOPHENE-2-CARBOXYLIC ACID {4-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 449 $[M+H]^+$

Example 89

N-{4-[2-(4-1,2-BENZISOTHIAZOL-3-YL-PIPERAZIN-1-YL)-ETHYL]-PHENYL}-ISOBUTYRAMIDE

Isolated in 100% purity @ 254 nm; LCMS (APCI): 409 $[M+H]^+$

Example 90

5-METHYL-ISOXAZOLE-3-CARBOXYLIC ACID {4-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 448 $[M+H]^+$

Example 91

N-{4-[2-(4-1,2-BENZISOTHIAZOL-3-YL-PIPERAZIN-1-YL)-ETHYL]-PHENYL}-2-(2,5-DIOXO-IMIDAZOLIDIN-4-YL)-ACETAMIDE

Isolated in 91% purity @ 254 nm; LCMS (APCI): 479 $[M+H]^+$

Example 92

5-CHLORO-1-METHYL-1H-PYRAZOLE-4-CARBOXYLIC ACID {4-[2-(4-1,2-BENZISOTHIAZOL-3-YL-PIPERAZIN-1-YL)-ETHYL]-PHENYL}-AMIDE

Isolated in 96% purity @ 254 nm; LCMS (APCI): 482 [M+H]+

Example 93

5-TERT-BUTYL-2-M ETHYL-2H-PYRAZOLE-3-CARBOXYLIC ACID {4-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 503 $[M+H]^+$

Example 94

4-METHYL-1,2,3-THIADIAZOLE-5-CARBOXYLIC ACID {4-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 465 $[M+H]^+$

Example 95

FURAN-2-CARBOXYLIC ACID {4-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 433 $[M+H]^+$

Example 96

5-METHYL-2-PHENYL-2H-1,2,3-TRIAZOLE-4-CARBOXYLIC ACID {4-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 524 $[M+H]^+$

Example 97

N-{4-[2-(4-1,2-BENZISOTHIAZOL-3-YL-PIPERAZIN-1-YL)-ETHYL]-PHENYL}-3-METHYL-BUTYRAMIDE

Isolated in 100% purity @ 254 nm; LCMS (APCI): 423 $[M+H]^+$

Example 98

CYCLOPENTANECARBOXYLIC ACID {4-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 435 [M+H]+

Example 99

N-{4-[2-(4-1,2-BENZISOTHIAZOL-3-YL-PIPERAZIN-1-YL)-ETHYL]-PHENYL}-4-FLUORO-BENZAMIDE

Isolated in 100% purity @ 254 nm; LCMS (APCI): 461 $[M+H]^+$

Example 100

N-{4-[2-(4-1,2-BENZISOTHIAZOL-3-YL-PIPERAZIN-1-YL)-ETHYL]-PHENYL}-BENZAMIDE

Isolated in 100% purity @ 254 nm; LCMS (APCI): 443 $[M+H]^+$

Example 101

N-{4-[2-(4-1,2-BENZISOTHIAZOL-3-YL-PIPERAZIN-1-YL)-ETHYL]-PHENYL}-2-CYCLOPENTYL-ACETAMIDE

Isolated in 100% purity @ 254 nm; LCMS (APCI): 449 $[M+H]^+$

Example 102

2,5-DIMETHYL-2H-PYRAZOLE-3-CARBOXYLIC ACID {4-[2-(4-1,2-BENZISOTHIAZOL-3-YL-PIPERAZIN-1-YL)-ETHYL]-PHENYL}-AMIDE

Isolated in 93% purity @ 254 nm; LCMS (APCI): 461 $[M+H]^+$

Example 103

N-{4-[2-(4-1,2-BENZISOTHIAZOL-3-YL-PIPERAZIN-1-YL)-ETHYL]-PHENYL}-2-FLUORO-BENZAMIDE

Isolated in 99% purity @ 254 nm; LCMS (APCI): 462 $[M+H]^+$

Example 104

N-{4-[2-(4-1,2-BENZISOTHIAZOL-3-YL-PIPERAZIN-1-YL)-ETHYL]-PHENYL}-3,5-DIMETHOXY-BENZAMIDE

Isolated in 99% purity @ 254 nm; LCMS (APCI): 503 $[M+H]^+$

Example 105

N-{4-[2-(4-1,2-BENZISOTHIAZOL-3-YL-PIPERAZIN-1-YL)-ETHYL]-PHENYL}-2-BENZYLOXY-ACETAMIDE

Isolated in 100% purity @ 254 nm; LCMS (APCI): 487 $[M+H]^+$

Example 106

N-{4-[2-(4-1,2-BENZISOTHIAZOL-3-YL-PIPERAZIN-1-YL)-ETHYL]-PHENYL}-2-BROMO-BENZAMIDE

Isolated in 100% purity @ 254 nm; LCMS (APCI): 522 $[M+H]^+$

Example 107

N-{4-[2-(4-1,2-BENZISOTHIAZOL-3-YL-PIPERAZIN-1-YL)-ETHYL]-PHENYL}-3-BROMO-BENZAMIDE

Isolated 100% purity @ 254 nm; LCMS (APCI): 522 $[M+H]^+$

Example 108

N-{4-[2-(4-1,2-BENZISOTHIAZOL-3-YL-PIPERAZIN-1-YL)-ETHYL]-PHENYL}-2,5-DIFLUORO-BENZAMIDE

Isolated in 99% purity @ 254 nm; LCMS (APCI): 479 $[M+H]^+$

Example 109

N-{4-[2-(4-1,2-BENZISOTHIAZOL-3-YL-PIPERAZIN-1-YL)-ETHYL]-PHENYL}-2,4-DICHLORO-BENZAMIDE

Isolated in 100% purity @ 254 nm; LCMS (APCI): 512 $[M+H]^+$

Example 110

N-{4-[2-(4-1,2-BENZISOTHIAZOL-3-YL-PIPERAZIN-1-YL)-ETHYL]-PHENYL}-4-FLUORO-3-TRIFLUOROMETHYL-BENZAMIDE

Isolated in 100% purity @ 254 nm; LCMS (APCI): 529 $[M+H]^+$

Example 111

N-{4-[2-(4-1,2-BENZISOTHIAZOL-3-YL-PIPERAZIN-1-YL)-ETHYL]-PHENYL}-2,4-DIFLUORO-BENZAMIDE

Isolated in 97% purity @ 254 nm; LCMS (APCI): 479 [M+H]+

Example 112

N-{4-[2-(4-1,2-BENZISOTHIAZOL-3-YL-PIPERAZIN-1-YL)-ETHYL]-PHENYL}-3-CYANO-BENZAMIDE

Isolated in 97% purity @ 254 nm; LCMS (APCI): 468 $[M+H]^+$

Example 113

N-{4-[2-(4-1,2-BENZISOTHIAZOL-3-YL-PIPERAZIN-1-YL)-ETHYL]-PHENYL}-4-TRIFLUOROMETHOXY-BENZAMIDE

Isolated in 100% purity @ 254 nm; LCMS (APCI): 527 $[M+H]^+$

Example 114

N-{4-[2-(4-1,2-BENZISOTHIAZOL-3-YL-PIPERAZIN-1-YL)-ETHYL]-PHENYL}-3-FLUORO-BENZAMIDE

Isolated in 99% purity @ 254 nm; LCMS (APCI): 461 $[M+H]^+$

Example 115

N-{4-[2-(4-1,2-BENZISOTHIAZOL-3-YL-PIPERAZIN-1-YL)-ETHYL]-PHENYL}-2-METHYL-BENZAMIDE

Isolated in 100% purity @ 254 nm; LCMS (APCI): 457 $[M+H]^+$

Example 116

N-{4-[2-(4-1,2-BENZISOTHIAZOL-3-YL-PIPERAZIN-1-YL)-ETHYL]-PHENYL}-2-METHOXY-BENZAMIDE

Isolated in 99% purity @ 254 nm; LCMS (APCI): 473 $[M+H]^+$

Example 117

N-{4-[2-(4-1,2-BENZISOTHIAZOL-3-YL-PIPERAZIN-1-YL)-ETHYL]-PHENYL}-4-TERT-BUTYL-BENZAMIDE

Isolated in 100% purity @ 254 nm; LCMS (APCI): 499 $[M+H]^+$

Example 118

N-{4-[2-(4-1,2-BENZISOTHIAZOL-3-YL-PIPERAZIN-1-YL)-ETHYL]-PHENYL}-3-PHENYL-PROPIONAMIDE

Isolated in 100% purity @ 254 nm; LCMS (APCI): 471 $[M+H]^+$

Example 119

N-{4-[2-(4-1,2-BENZISOTHIAZOL-3-YL-PIPERAZIN-1-YL)-ETHYL]-PHENYL}-2,4-DIMETHOXY-BENZAMIDE

Isolated in 99% purity @ 254 nm; LCMS (APCI): 503 $[M+H]^+$

Example 120

N-{4-[2-(4-1,2-BENZISOTHIAZOL-3-YL-PIPERAZIN-1-YL)-ETHYL]-PHENYL}-3,5-DIFLUORO-BENZAMIDE

Isolated in 100% purity @ 254 nm; LCMS (APCI): 479 $[M+H]^+$

Example 121

N-{4-[2-(4-1,2-BENZISOTHIAZOL-3-YL-PIPERAZIN-1-YL)-ETHYL]-PHENYL}-3-METHYL-BENZAMIDE

Isolated in 99% purity @ 254 nm; LCMS (APCI): 457 $[M+H]^+$

Example 122

N-{4-[2-(4-1,2-BENZISOTHIAZOL-3-YL-PIPERAZIN-1-YL)-ETHYL]-PHENYL}-2-(3,4-DIMETHOXY-PHENYL)-ACETAMIDE

Isolated in 100% purity @ 254 nm; LCMS (APCI): 517 $[M+H]^+$

Example 123

N-{4-[2-(4-1,2-BENZISOTHIAZOL-3-YL-PIPERAZIN-1-YL)-ETHYL]-PHENYL}-2-NITRO-BENZAMIDE

Isolated in 92% purity @ 254 nm; LCMS (APCI): 488 $[M+H]^+$

Example 124

PYRIDINE-2-CARBOXYLIC ACID {4-[2-(4-1,2-BENZISOTHIAZOL-3-YL-PIPERAZIN-1-YL)-ETHYL]-PHENYL}-AMIDE

Isolated in 98% purity @ 254 nm; LCMS (APCI): 444 [M+H]+

Example 125

N-{4-[2-(4-1,2-BENZISOTHIAZOL-3-YL-PIPERAZIN-1-YL)-ETHYL]-PHENYL}-3-FLUORO-4-METHYL-BENZAMIDE

Isolated in 99% purity @ 254 nm; LCMS (APCI): 475 $[M+H]^+$

Example 126

N-{4-[2-(4-1,2-BENZISOTHIAZOL-3-YL-PIPERAZIN-1-YL)-ETHYL]-PHENYL}-4-TRIFLUOROMETHYL-BENZAMIDE

Isolated in 100% purity @ 254 nm; LCMS (APCI): 511 $[M+H]^+$

Example 127

N-{4-[2-(4-1,2-BENZISOTHIAZOL-3-YL-PIPERAZIN-1-YL)-ETHYL]-PHENYL}-4-METHOXY-3-TRIFLUOROMETHYL-BENZAMIDE

Isolated in 100% purity @ 254 nm; LCMS (APCI): 541 $[M+H]^+$

Example 128

N-{4-[2-(4-1,2-BENZISOTHIAZOL-3-YL-PIPERAZIN-1-YL)-ETHYL]-PHENYL}-4-CHLORO-BENZAMIDE

Isolated in 99% purity @ 254 nm; LCMS (APCI): 478 $[M+H]^+$

Example 129

N-{4-[2-(4-1,2-BENZISOTHIAZOL-3-YL-PIPERAZIN-1-YL)-ETHYL]-PHENYL}-2-(4-CHLORO-PHENYL)-ACETAMIDE

Isolated in 100% purity @ 254 nm; LCMS (APCI): 492 $[M+H]^+$

Example 130

N-{4-[2-(4-1,2-BENZISOTHIAZOL-3-YL-PIPERAZIN-1-YL)-ETHYL]-PHENYL}-3,4-DIMETHYL-BENZAMIDE

Isolated in 100% purity @ 254 nm; LCMS (APCI): 471 $[M+H]^+$

Example 131

N-{4-[2-(4-1,2-BENZISOTHIAZOL-3-YL-PIPERAZIN-1-YL)-ETHYL]-PHENYL}-2,3-DIMETHYL-BENZAMIDE

Isolated in 100% purity @ 254 nm; LCMS (APCI): 471 $[M+H]^+$

Example 132

N-{4-[2-(4-1,2-BENZISOTHIAZOL-3-YL-PIPERAZIN-1-YL)-ETHYL]-PHENYL}-2-NAPHTHALEN-1-YL-ACETAMIDE

Isolated in 100% purity @ 254 nm; LCMS (APCI): 507 $[M+H]^+$

Example 133

N-{4-[2-(4-1,2-BENZISOTHIAZOL-3-YL-PIPERAZIN-1-YL)-ETHYL]-PHENYL}-4-BROMO-BENZAMIDE

Isolated in 89% purity @ 254 nm; LCMS (APCI): 522 $[M+H]^+$

Example 134

1,3-BENZODIOXOLE-5-CARBOXYLIC ACID {4-[2-(4-1,2-BENZISOTHIAZOL-3-YL-PIPERAZIN-1-YL)-ETHYL]-PHENYL}-AMIDE

Isolated in 95% purity @ 254 nm; LCMS (APCI): 487 $[M+H]^+$

Example 135

N-{4-[2-(4-1,2-BENZISOTHIAZOL-3-YL-PIPERAZIN-1-YL)-ETHYL]-PHENYL}-6-CHLORO-NICOTINAMIDE

Isolated in 98% purity @ 254 nm; LCMS (APCI): 479 $[M+H]^+$

Example 136

N-{4-[2-(4-1,2-BENZISOTHIAZOL-3-YL-PIPERAZIN-1-YL)-ETHYL]-PHENYL}-NICOTINAMIDE

Isolated in 100% purity @ 254 nm; LCMS (APCI): 444 $[M+H]^+$

Example 137

N-{4-[2-(4-1,2-BENZISOTHIAZOL-3-YL-PIPERAZIN-1-YL)-ETHYL]-PHENYL}-4-ETHYL-BENZAMIDE

Isolated in 100% purity @ 254 nm; LCMS (APCI): 471 [M+H]+

Example 138

N-{2-[2-(4-1,2-BENZISOTHIAZOL-3-YL-PIPERAZIN-1-YL)-ETHYL]-PHENYL}-2-FLUORO-BENZAMIDE

Isolated in 99% purity @ 254 nm; LCMS (APCI): 461 $[M+H]^+$

Example 139

N-{2-[2-(4-1,2-BENZISOTHIAZOL-3-YL-PIPERAZIN-1-YL)-ETHYL]-PHENYL}-2,4-DIFLUORO-BENZAMIDE

Isolated in 94% purity @ 254 nm; LCMS (APCI): 479 $[M+H]^+$

Example 140

N-{2-[2-(4-1,2-BENZISOTHIAZOL-3-YL-PIPERAZIN-1-YL)-ETHYL]-PHENYL}-3-PHENYL-PROPIONAMIDE

Isolated in 100% purity @ 254 nm; LCMS (APCI): 471 $[M+H]^+$

Example 141

N-{2-[2-(4-1,2-BENZISOTHIAZOL-3-YL-PIPERAZIN-1-YL)-ETHYL]-PHENYL}-4-CHLORO-BENZAMIDE

Isolated in 99% purity @ 254 nm; LCMS (APCI): 478 $[M+H]^+$

Example 142

1,3-BENZODIOXOLE-5-CARBOXYLIC ACID {2-[2-(4-1,2-BENZISOTHIAZOL-3-YL-PIPERAZIN-1-YL)-ETHYL]-PHENYL}-AMIDE

Isolated in 96% purity @ 254 nm; LCMS (APCI): 487 $[M+H]^+$

Example 143

N-{2-[2-(4-1,2-BENZISOTHIAZOL-3-YL-PIPERAZIN-1-YL)-ETHYL]-PHENYL}-6-CHLORO-NICOTINAMIDE

Isolated in 99% purity @ 254 nm; LCMS (APCI): 479 $[M+H]^+$

Example 144

N-{2-[2-(4-1,2-BENZISOTHIAZOL-3-YL-PIPERAZIN-1-YL)-ETHYL]-PHENYL}-NICOTINAMIDE

Isolated in 100% purity @ 254 nm; LCMS (APCI): 444 $[M+H]^+$

Example 145

N-{2-[2-(4-1,2-BENZISOTHIAZOL-3-YL-PIPERAZIN-1-YL)-ETHYL]-PHENYL}-4-ETHYL-BENZAMIDE

Isolated in 100% purity @ 254 nm; LCMS (APCI): 471 $[M+H]^+$

Example 146

N-{2-[2-(4-1,2-BENZISOTHIAZOL-3-YL-PIPERAZIN-1-YL)-ETHYL]-PHENYL}-2-BENZYLOXY-ACETAMIDE

Isolated in 97% purity @ 254 nm; LCMS (APCI): 487 $[M+H]^+$

Example 147

N-{2-[2-(4-1,2-BENZISOTHIAZOL-3-YL-PIPERAZIN-1-YL)-ETHYL]-PHENYL}-2-BROMO-BENZAMIDE

Isolated in 100% purity @ 254 nm; LCMS (APCI): 522 $[M+H]^+$

Example 148

N-{2-[2-(4-1,2-Benzisothiazol-3-yl-piperazin-1-yl)-ethyl]-phenyl}-3-bromo-benzamide Isolated in 94% purity @ 254 nm; LCMS (APCI): 521 $[M+H]^+$ Example 149

N-{2-[2-(4-1,2-BENZISOTHIAZOL-3-YL-PIPERAZIN-1-YL)-ETHYL]-PHENYL}-2,5-DIFLUORO-BENZAMIDE

Isolated in 97% purity @ 254 nm; LCMS (APCI): 479 $[M+H]^+$

Example 150

N-{2-[2-(4-1,2-BENZISOTHIAZOL-3-YL-PIPERAZIN-1-YL)-ETHYL]-PHENYL}-4-CYANO-BENZAMIDE

Isolated in 96% purity @ 254 nm; LCMS (APCI): 468 [M+H]+

Example 151

N-{2-[2-(4-1,2-BENZISOTHIAZOL-3-YL-PIPERAZIN-1-YL)-ETHYL]-PHENYL}-2,4-DICHLORO-BENZAMIDE

Isolated in 95% purity @ 254 nm; LCMS (APCI): 512 $[M+H]^+$

Example 152

N-{2-[2-(4-1,2-BENZISOTHIAZOL-3-YL-PIPERAZIN-1-YL)-ETHYL]-PHENYL}-4-FLUORO-3-TRIFLUOROMETHYL-BENZAMIDE

Isolated in 100% purity @ 254 nm; LCMS (APCI): 529 $[M+H]^+$

Example 153

N-{2-[2-(4-1,2-BENZISOTHIAZOL-3-YL-PIPERAZIN-1-YL)-ETHYL]-PHENYL}-3-CYANO-BENZAMIDE

Isolated in 96% purity @ 254 nm; LCMS (APCI): 468 $[M+H]^+$

Example 154

N-{2-[2-(4-1,2-BENZISOTHIAZOL-3-YL-PIPERAZIN-1-YL)-ETHYL]-PHENYL}-4-TRIFLUOROMETHOXY-BENZAMIDE

Isolated in 100% purity @ 254 nm; LCMS (APCI): 527 $[M+H]^+$

Example 155

N-{2-[2-(4-1,2-BENZISOTHIAZOL-3-YL-PIPERAZIN-1-YL)-ETHYL]-PHENYL}-3-FLUORO-BENZAMIDE

Isolated in 98% purity © 254 nm; LCMS (APCI): 461 $[M+H]^+$

Example 156

N-{2-[2-(4-1,2-BENZISOTHIAZOL-3-YL-PIPERAZIN-1-YL)-ETHYL]-PHENYL}-2-METHYL-BENZAMIDE

Isolated in 99% purity © 254 nm; LCMS (APCI): 457 $[M+H]^+$

Example 157

N-{2-[2-(4-1,2-BENZISOTHIAZOL-3-YL-PIPERAZIN-1-YL)-ETHYL]-PHENYL}-2-METHOXY-BENZAMIDE

Isolated in 100% purity @ 254 nm; LCMS (APCI): 473 $[M+H]^+$

Example 158

N-{2-[2-(4-1,2-BENZISOTHIAZOL-3-YL-PIPERAZIN-1-YL)-ETHYL]-PHENYL}-4-TERT-BUTYL-BENZAMIDE

Isolated in 100% purity @ 254 nm; LCMS (APCI): 499 $[M+H]^+$

Example 159

N-{2-[2-(4-1,2-BENZISOTHIAZOL-3-YL-PIPERAZIN-1-YL)-ETHYL]-PHENYL}-3,5-DIFLUORO-BENZAMIDE

Isolated in 98% purity @ 254 nm; LCMS (APCI): 479 $[M+H]^+$

Example 160

N-{2-[2-(4-1,2-BENZISOTHIAZOL-3-YL-PIPERAZIN-1-YL)-ETHYL]-PHENYL}-3-METHYL-BENZAMIDE

Isolated in 100% purity @ 254 nm; LCMS (APCI): 457 $[M+H]^+$

Example 161

N-{2-[2-(4-1,2-BENZISOTHIAZOL-3-YL-PIPERAZIN-1-YL)-ETHYL]-PHENYL}-2-(3,4-DIMETHOXY-PHENYL)-ACETAMIDE

Isolated in 100% purity @ 254 nm; LCMS (APCI): 517 $[M+H]^+$

Example 162

N-{2-[2-(4-1,2-BENZISOTHIAZOL-3-YL-PIPERAZIN-1-YL)-ETHYL]-PHENYL}-2-NITRO-BENZAMIDE

Isolated in 98% purity @ 254 nm; LCMS (APCI): 488 $[M+H]^+$

Example 163

PYRIDINE-2-CARBOXYLIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 444 [M+H]+

Example 164

N-{2-[2-(4-1,2-BENZISOTHIAZOL-3-YL-PIPERAZIN-1-YL)-ETHYL]-PHENYL}-3-FLUORO-4-METHYL-BENZAMIDE

Isolated in 100% purity @ 254 nm; LCMS (APCI): 475 $[M+H]^+$

Example 165

N-{2-[2-(4-1,2-BENZISOTHIAZOL-3-YL-PIPERAZIN-1-YL)-ETHYL]-PHENYL}-4-TRIFLUOROMETHYL-BENZAMIDE

Isolated in 100% purity @ 254 nm; LCMS (APCI): 511 $[M+H]^+$

Example 166

N-{2-[2-(4-1,2-BENZISOTHIAZOL-3-YL-PIPERAZIN-1-YL)-ETHYL]-PHENYL}-4-METHOXY-3-TRIFLUOROMETHYL-BENZAMIDE

Isolated in 100% purity @ 254 nm; LCMS (APCI): 541 $[M+H]^+$

Example 167

N-{2-[2-(4-1,2-BENZISOTHIAZOL-3-YL-PIPERAZIN-1-YL)-ETHYL]-PHENYL}-2-(4-CHLORO-PHENYL)-ACETAMIDE

Isolated in 100% purity @ 254 nm; LCMS (APCI): 492 $[M+H]^+$

Example 168

N-{2-[2-(4-1,2-BENZISOTHIAZOL-3-YL-PIPERAZIN-1-YL)-ETHYL]-PHENYL}-3,4-DIMETHYL-BENZAMIDE

Isolated in 100% purity @ 254 nm; LCMS (APCI): 471 $[M+H]^+$

Example 169

N-{2-[2-(4-1,2-BENZISOTHIAZOL-3-YL-PIPERAZIN-1-YL)-ETHYL]-PHENYL}-2,3-DIMETHYL-BENZAMIDE

Isolated in 96% purity @ 254 nm; LCMS (APCI): 471 $[M+H]^+$

Example 170

N-{2-[2-(4-1,2-BENZISOTHIAZOL-3-YL-PIPERAZIN-1-YL)-ETHYL]-PHENYL}-4-BROMO-BENZAMIDE

Isolated in 89% purity @ 254 nm; LCMS (APCI): 522 $[M+H]^+$

Example 171

N-{2-[2-(4-1,2-BENZISOTHIAZOL-3-YL-PIPERAZIN-1-YL)-ETHYL]-PHENYL}-4-METHYL-BENZAMIDE

Isolated in 100% purity @ 254 nm; LCMS (APCI): 457 $[M+H]^+$

Example 172

N-{3-[2-(4-1,2-BENZISOTHIAZOL-3-YL-PIPERAZIN-1-YL)-ETHYL]-PHENYL}-4-CHLORO-BENZAMIDE

Isolated in 100% purity @ 254 nm; LCMS (APCI): 478 $[M+H]^+$

Example 173

N-{3-[2-(4-1,2-BENZISOTHIAZOL-3-YL-PIPERAZIN-1-YL)-ETHYL]-PHENYL}-4-CHLORO-BENZAMIDE

Isolated in 98% purity @ 254 nm; LCMS (APCI): 479 $[M+H]^+$

Example 174

N-{3-[2-(4-1,2-BENZISOTHIAZOL-3-YL-PIPERAZIN-1-YL)-ETHYL]-PHENYL}-NICOTINAMIDE

Isolated in 100% purity @ 254 nm; LCMS (APCI): 444 $[M+H]^+$

Example 175

N-{3-[2-(4-1,2-BENZISOTHIAZOL-3-YL-PIPERAZIN-1-YL)-ETHYL]-PHENYL}-4-ETHYL-BENZAMIDE

Isolated in 100% purity © 254 nm; LCMS (APCI): 471 $[M+H]^+$

Example 176

N-{3-[2-(4-1,2-BENZISOTHIAZOL-3-YL-PIPERAZIN-1-YL)-ETHYL]-PHENYL}-2-BENZYLOXY-ACETAMIDE

Isolated in 100% purity @ 254 nm; LCMS (APCI): 487 [M+H]+

Example 177

N-{3-[2-(4-1,2-BENZISOTHIAZOL-3-YL-PIPERAZIN-1-YL)-ETHYL]-PHENYL}-2,5-DIFLUORO-BENZAMIDE

Isolated in 98% purity @ 254 nm; LCMS (APCI): 479 $[M+H]^+$

Example 178

N-{3-[2-(4-1,2-BENZISOTHIAZOL-3-YL-PIPERAZIN-1-YL)-ETHYL]-PHENYL}-4-CYANO-BENZAMIDE

Isolated in 95% purity @ 254 nm; LCMS (APCI): 468 $[M+H]^+$

Example 179

N-{3-[2-(4-1,2-BENZISOTHIAZOL-3-YL-PIPERAZIN-1-YL)-ETHYL]-PHENYL}-2,4-DICHLORO-BENZAMIDE

Isolated in 100% purity @ 254 nm; LCMS (APCI): 512 $[M+H]^+$

Example 180

N-{3-[2-(4-1,2-BENZISOTHIAZOL-3-YL-PIPERAZIN-1-YL)-ETHYL]-PHENYL}-4-FLUORO-3-TRIFLUOROMETHYL-BENZAMIDE

Isolated in 100% purity @ 254 nm; LCMS (APCI): 529 $[M+H]^+$

Example 181

N-{3-[2-(4-1,2-BENZISOTHIAZOL-3-YL-PIPERAZIN-1-YL)-ETHYL]-PHENYL}-3-CYANO-BENZAMIDE

Isolated in 100% purity @ 254 nm; LCMS (APCI): 468 $[M+H]^+$

Example 182

N-{3-[2-(4-1,2-BENZISOTHIAZOL-3-YL-PIPERAZIN-1-YL)-ETHYL]-PHENYL}-4-TRIFLUOROMETHOXY-BENZAMIDE

Isolated in 100% purity @ 254 nm; LCMS (APCI): 527 $[M+H]^+$

Example 183

N-{3-[2-(4-1,2-BENZISOTHIAZOL-3-YL-PIPERAZIN-1-YL)-ETHYL]-PHENYL}-3-FLUORO-BENZAMIDE

Isolated in 100% purity @ 254 nm; LCMS (APCI): 461 $[M+H]^+$

Example 184

N-{3-[2-(4-1,2-BENZISOTHIAZOL-3-YL-PIPERAZIN-1-YL)-ETHYL]-PHENYL}-2-METHYL-BENZAMIDE

Isolated in 100% purity @ 254 nm; LCMS (APCI): 457 $[M+H]^+$

Example 185

N-{3-[2-(4-1,2-BENZISOTHIAZOL-3-YL-PIPERAZIN-1-YL)-ETHYL]-PHENYL}-2-METHOXY-BENZAMIDE

Isolated in 99% purity @ 254 nm; LCMS (APCI): 473 $[M+H]^+$

Example 186

N-{3-[2-(4-1,2-BENZISOTHIAZOL-3-YL-PIPERAZIN-1-YL)-ETHYL]-PHENYL}-3-NITRO-BENZAMIDE

Isolated in 93% purity © 254 nm; LCMS (APCI): 488 $[M+H]^+$

Example 187

N-{3-[2-(4-1,2-BENZISOTHIAZOL-3-YL-PIPERAZIN-1-YL)-ETHYL]-PHENYL}-4-TERT-BUTYL-BENZAMIDE

Isolated in 100% purity @ 254 nm; LCMS (APCI): 499 $[M+H]^+$

Example 188

N-{3-[2-(4-1,2-BENZISOTHIAZOL-3-YL-PIPERAZIN-1-YL)-ETHYL]-PHENYL}-2,4-DIMETHOXY-BENZAMIDE

Isolated in 100% purity @ 254 nm; LCMS (APCI): 503 $[M+H]^+$

Example 189

N-{3-[2-(4-1,2-BENZISOTHIAZOL-3-YL-PIPERAZIN-1-YL)-ETHYL]-PHENYL}-3,5-DIFLUORO-BENZAMIDE

Isolated in 99% purity @ 254 nm; LCMS (APCI): 479 [M+H]+

Example 190

N-{3-[2-(4-1,2-BENZISOTHIAZOL-3-YL-PIPERAZIN-1-YL)-ETHYL]-PHENYL}-3-METHYL-BENZAMIDE

Isolated in 100% purity @ 254 nm; LCMS (APCI): 457 $[M+H]^+$

Example 191

N-{3-[2-(4-1,2-BENZISOTHIAZOL-3-YL-PIPERAZIN-1-YL)-ETHYL]-PHENYL}-2-(3,4-DIMETHOXY-PHENYL)-ACETAMIDE

Isolated in 99% purity @ 254 nm; LCMS (APCI): 517 $[M+H]^+$

Example 192

N-{3-[2-(4-1,2-BENZISOTHIAZOL-3-YL-PIPERAZIN-1-YL)-ETHYL]-PHENYL}-2-NITRO-BENZAMIDE

Isolated in 98% purity @ 254 nm; LCMS (APCI): 488 $[M+H]^+$

Example 193

PYRIDINE-2-CARBOXYLIC ACID {3-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 444 $[M+H]^+$

Example 194

N-{3-[2-(4-1,2-BENZISOTHIAZOL-3-YL-PIPERAZIN-1-YL)-ETHYL]-PHENYL}-3-FLUORO-4-METHYL-BENZAMIDE

Isolated in 99% purity @ 254 nm; LCMS (APCI): 475 $[M+H]^+$

Example 195

N-{3-[2-(4-1,2-BENZISOTHIAZOL-3-YL-PIPERAZIN-1-YL)-ETHYL]-PHENYL}-4-TRIFLUOROMETHYL-BENZAMIDE

Isolated in 100% purity @ 254 nm; LCMS (APCI): 511 $[M+H]^+$

Example 196

N-{3-[2-(4-1,2-BENZISOTHIAZOL-3-YL-PIPERAZIN-1-YL)-ETHYL]-PHENYL}-2-(4-CHLORO-PHENYL)-ACETAMIDE

Isolated in 100% purity @ 254 nm; LCMS (APCI): 492 $[M+H]^+$

Example 197

N-{3-[2-(4-1,2-BENZISOTHIAZOL-3-YL-PIPERAZIN-1-YL)-ETHYL]-PHENYL}-3,4-DIMETHYL-BENZAMIDE

Isolated in 100% purity @ 254 nm; LCMS (APCI): 471 $[M+H]^+$

Example 198

N-{3-[2-(4-1,2-BENZISOTHIAZOL-3-YL-PIPERAZIN-1-YL)-ETHYL]-PHENYL}-2,3-DIMETHYL-BENZAMIDE

Isolated in 100% purity @ 254 nm; LCMS (APCI): 471 $[M+H]^+$

Example 199

N-{3-[2-(4-1,2-BENZISOTHIAZOL-3-YL-PIPERAZIN-1-YL)-ETHYL]-PHENYL}-2-NAPHTHALEN-1-YL-ACETAMIDE

Isolated in 99% purity @ 254 nm; LCMS (APCI): 507 $[M+H]^+$

Example 200

N-{3-[2-(4-1,2-BENZISOTHIAZOL-3-YL-PIPERAZIN-1-YL)-ETHYL]-PHENYL}-2-FLUORO-BENZAMIDE

Isolated in 100% purity @ 254 nm; LCMS (APCI): 461 $[M+H]^+$

Example 201

N-{3-[2-(4-1,2-BENZISOTHIAZOL-3-YL-PIPERAZIN-1-YL)-ETHYL]-PHENYL}-2,4-DIFLUORO-BENZAMIDE

Isolated in 100% purity @ 254 nm; LCMS (APCI): 479 $[M+H]^+$

Example 202

N-{3-[2-(4-1,2-BENZISOTHIAZOL-3-YL-PIPERAZIN-1-YL)-ETHYL]-PHENYL}-3-PHENYL-PROPIONAMIDE

Isolated in 100% purity @ 254 nm; LCMS (APCI): 471 [M+H]+

Example 203

PYRAZINE-2-CARBOXYLIC ACID {4-[2-(4-1,2-BENZISOTHIAZOL-3-YL-PIPERAZIN-1-YL)-ETHYL]-PHENYL}-AMIDE

4-[2-(4-Benzo[d]isothiazol-3-yl-piperazin-1-yl)-ethyl]-phenylamine was diluted to 0.40 M with anhydrous dichloromethane, then delivered to an 8 mL vial via pipette (0.2 mmol). To the amine solution was added base (0.4 M triethylamine in dichloromethane, 0.20 mmol). Pyrazine-2-carbonyl chloride was diluted to 0.40 M with dichloromethane, and added at rt (0.2 mmol). The reaction was shaken overnight at rt, then evaluated by MS. The reaction was concentrated using an HT-12 GeneVac, then purified by HPLC (30×100 mm ODS-A C(18) 5u column). Pyrazine-2-carboxylic acid {4-[2-(4-1,2-benzisothiazol-3-yl-piperazin-1-yl)-ethyl]-phenyl}-amide was isolated in 88% purity @ 254 nm, LCMS (APCI): 445 $[M+H]^+$.

The amides of Examples 204–265 were synthesized in combinatorial library format following the steps outlined in Example 203 on a 0.20 mmol scale using 4-[2-(4-benzo[d]isothiazol-3-yl-piperazin-1-yl)-ethyl]-phenylamine, 3-[2-(4-benzo[d]isothiazol-3-yl-piperazin-1-yl)-ethyl]-phenylamine, or 2-[2-(4-benzo[d]isothiazol-3-yl-piperazin-1-yl)-ethyl]-phenylamine with appropriate acid chloride or chloroformate starting materials. The crude products were purified by HPLC (30×100 mm ODS-A C(18) 5u column).

Example 204

{4-[2-(4-1,2-BENZISOTHIAZOL-3-YL-PIPERAZIN-1-YL)-ETHYL]-PHENYL}-CARBAMIC ACID 2-METHOXY-ETHYL ESTER

Isolated in 97% purity @ 254 nm; LCMS (APCI): 441 $[M+H]^+$

Example 205

{4-[2-(4-1,2-BENZISOTHIAZOL-3-YL-PIPERAZIN-1-YL)-ETHYL]-PHENYL}-CARBAMIC ACID PROPYL ESTER

Isolated in 96% purity @ 254 nm; LCMS (APCI): 425 [M+H]+

Example 206

{4-[2-(4-1,2-BENZISOTHIAZOL-3-YL-PIPERAZIN-1-YL)-ETHYL]-PHENYL}-CARBAMIC ACID BENZYL ESTER

Isolated in 96% purity @ 254 nm; LCMS (APCI): 473 $[M+H]^+$

Example 207

{4-[2-(4-1,2-BENZISOTHIAZOL-3-YL-PIPERAZIN-1-YL)-ETHYL]-PHENYL}-CARBAMIC ACID BUT-2-YNYL ESTER

Isolated in 97% purity @ 254 nm; LCMS (APCI): 435 $[M+H]^+$

Example 208

{4-[2-(4-1,2-BENZISOTHIAZOL-3-YL-PIPERAZIN-1-YL)-ETHYL]-PHENYL}-CARBAMIC ACID VINYL ESTER

Isolated in 97% purity @ 254 nm; LCMS (APCI): 409 $[M+H]^+$

Example 209

{4-[2-(4-1,2-BENZISOTHIAZOL-3-YL-PIPERAZIN-1-YL)-ETHYL]-PHENYL}-CARBAMIC ACID ISOBUTYL ESTER

Isolated in 99% purity @ 254 nm; LCMS (APCI): 439 $[M+H]^+$

Example 210

{4-[2-(4-1,2-BENZISOTHIAZOL-3-YL-PIPERAZIN-1-YL)-ETHYL]-PHENYL}-CARBAMIC ACID BUTYL ESTER

Isolated in 100% purity @ 254 nm; LCMS (APCI): 439 $[M+H]^+$

Example 211

{4-[2-(4-1,2-BENZISOTHIAZOL-3-YL-PIPERAZIN-1-YL)-ETHYL]-PHENYL}-CARBAMIC ACID 4-METHOXY-PHENYL ESTER

Isolated in 91% purity @ 254 nm; LCMS (APCI): 489 $[M+H]^+$

Example 212

{4-[2-(4-1,2-BENZISOTHIAZOL-3-YL-PIPERAZIN-1-YL)-ETHYL]-PHENYL}-CARBAMIC ACID 2,2-DIMETHYL-PROPYL ESTER

Isolated in 100% purity @ 254 nm; LCMS (APCI): 453 $[M+H]^+$

Example 213

{4-[2-(4-1,2-BENZISOTHIAZOL-3-YL-PIPERAZIN-1-YL)-ETHYL]-PHENYL}-CARBAMIC ACID 2-METHOXY-PHENYL ESTER

Isolated in 99% purity @ 254 nm; LCMS (APCI): 489 $[M+H]^+$

Example 214

N-{2-[2-(4-1,2-BENZISOTHIAZOL-3-YL-PIPERAZIN-1-YL)-ETHYL]-PHENYL}-3-METHOXY-BENZAMIDE

Isolated in 99% purity @ 254 nm; LCMS (APCI): 473 $[M+H]^+$

Example 215

FURAN-2-CARBOXYLIC ACID {2-[2-(4-1,2-BENZISOTHIAZOL-3-YL-PIPERAZIN-1-YL)-ETHYL]-PHENYL}-AMIDE

Isolated in 89% purity @ 254 nm; LCMS (APCI): 433 $[M+H]^+$

Example 216

2,5-DICHLORO-THIOPHENE-3-CARBOXYLIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 518 $[M+H]^+$

Example 217

CYCLOPENTANECARBOXYLIC ACID {2-[2-(4-1,2-BENZISOTHIAZOL-3-YL-PIPERAZIN-1-YL)-ETHYL]-PHENYL}-AMIDE

Isolated in 94% purity @ 254 nm; LCMS (APCI): 435 $[M+H]^+$

Example 218

N-{2-[2-(4-1,2-BENZISOTHIAZOL-3-YL-PIPERAZIN-1-YL)-ETHYL]-PHENYL}-3-DIMETHYLAMINO-BENZAMIDE

Isolated in 93% purity @ 254 nm; LCMS (APCI): 485 [M+H]+

Example 219

N-{2-[2-(4-1,2-BENZISOTHIAZOL-3-YL-PIPERAZIN-1-YL)-ETHYL]-PHENYL}-4-FLUORO-BENZAMIDE

Isolated in 100% purity @ 254 nm; LCMS (APCI): 461 $[M+H]^+$

Example 220

N-{2-[2-(4-1,2-BENZISOTHIAZOL-3-YL-PIPERAZIN-1-YL)-ETHYL]-PHENYL}-BENZAMIDE

Isolated in 100% purity @ 254 nm; LCMS (APCI): 443 $[M+H]^+$

Example 221

N-{2-[2-(4-1,2-BENZISOTHIAZOL-3-YL-PIPERAZIN-1-YL)-ETHYL]-PHENYL}-2-CYCLOPENTYL-ACETAMIDE

Isolated in 100% purity @ 254 nm; LCMS (APCI): 449 $[M+H]^+$

Example 222

2,5-DIMETHYL-2H-PYRAZOLE-3-CARBOXYLIC ACID {2-[2-(4-1,2-BENZISOTHIAZOL-3-YL-PIPERAZIN-1-YL)-ETHYL]-PHENYL}-AMIDE

Isolated in 98% purity @ 254 nm; LCMS (APCI): 461 $[M+H]^+$

Example 223

THIOPHENE-2-CARBOXYLIC ACID {2-[2-(4-1,2-BENZISOTHIAZOL-3-YL-PIPERAZIN-1-YL)-ETHYL]-PHENYL}-AMIDE

Isolated in 87% purity @ 254 nm; LCMS (APCI): 449 $[M+H]^+$

Example 224

1-ACETYL-PIPERIDINE-4-CARBOXYLIC ACID {2-[2-(4-1,2-BENZISOTHIAZOL-3-YL-PIPERAZIN-1-YL)-ETHYL]-PHENYL}-AMIDE

Isolated in 88% purity @ 254 nm; LCMS (APCI): 492 $[M+H]^+$

Example 225

PYRAZINE-2-CARBOXYLIC ACID {2-[2-(4-1,2-BENZISOTHIAZOL-3-YL-PIPERAZIN-1-YL)-ETHYL]-PHENYL}-AMIDE

Isolated in 95% purity @ 254 nm; LCMS (APCI): 445 $[M+H]^+$

Example 226

P QUINOXALINE-2-CARBOXYLIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 495 $[M+H]^+$

Example 227

5-CHLORO-1-METHYL-1H-PYRAZOLE-4-CARBOXYLIC ACID {2-[2-(4-1,2-BENZISOTHIAZOL-3-YL-PIPERAZIN-1-YL)-ETHYL]-PHENYL}-AMIDE

Isolated in 94% purity @ 254 nm; LCMS (APCI): 482 $[M+H]^+$

Example 228

5-TERT-BUTYL-2-METHYL-2H-PYRAZOLE-3-CARBOXYLIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 503 $[M+H]^+$

Example 229

4-METHYL-1,2,3-THIADIAZOLE-5-CARBOXYLIC ACID {2-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 465 $[M+H]^+$

Example 230

5-METHYL-2-PHENYL-2H-1,2,3-TRIAZOLE-4-CARBOXYLIC ACID {2-[2-(4-1,2-BENZISOTHIAZOL-3-YL-PIPERAZIN-1-YL)-ETHYL]-PHENYL}-AMIDE

Isolated in 98% purity @ 254 nm; LCMS (APCI): 524 $[M+H]^+$

Example 231

N-{3-[2-(4-1,2-BENZISOTHIAZOL-3-YL-PIPERAZIN-1-YL)-ETHYL]-PHENYL}-3-METHOXY-BENZAMIDE

Isolated in 100% purity @ 254 nm; LCMS (APCI): 473 $[M+H]^+$

Example 232

FURAN-2-CARBOXYLIC ACID {3-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 433 $[M+H]^+$

Example 233

2,5-DICHLORO-THIOPHENE-3-CARBOXYLIC ACID {3-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 518 $[M+H]^+$

Example 234

N-{3-[2-(4-1,2-BENZISOTHIAZOL-3-YL-PIPERAZIN-1-YL)-ETHYL]-PHENYL}-3-METHYL-BUTYRAMIDE

Isolated in 99% purity @ 254 nm; LCMS (APCI): 423 $[M+H]^+$

Example 235

CYCLOPENTANECARBOXYLIC ACID {3-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 435 $[M+H]^+$

Example 236

N-{3-[2-(4-1,2-BENZISOTHIAZOL-3-YL-PIPERAZIN-1-YL)-ETHYL]-PHENYL}-3-DIMETHYLAMINO-BENZAMIDE

Isolated in 99% purity @ 254 nm; LCMS (APCI): 486 $[M+H]^+$

Example 237

N-{3-[2-(4-1,2-BENZISOTHIAZOL-3-YL-PIPERAZIN-1-YL)-ETHYL]-PHENYL}-4-FLUORO-BENZAMIDE

Isolated in 100% purity @ 254 nm; LCMS (APCI): 461 [M+H]+

Example 238

N-{3-[2-(4-1,2-BENZISOTHIAZOL-3-YL-PIPERAZIN-1-YL)-ETHYL]-PHENYL}-BENZAMIDE

Isolated in 100% purity @ 254 nm; LCMS (APCI): 443 $[M+H]^+$

Example 239

N-{3-[2-(4-1,2-BENZISOTHIAZOL-3-YL-PIPERAZIN-1-YL)-ETHYL]-PHENYL}-2-CYCLOPENTYL-ACETAMIDE

Isolated in 100% purity @ 254 nm; LCMS (APCI): 449 $[M+H]^+$

Example 240

2,5-DIMETHYL-2H-PYRAZOLE-3-CARBOXYLIC ACID {3-[2-(4-1,2-BENZISOTHIAZOL-3-YL-PIPERAZIN-1-YL)-ETHYL]-PHENYL}-AMIDE

Isolated in 97% purity @ 254 nm; LCMS (APCI): 461 $[M+H]^+$

Example 241

N-{3-[2-(4-1,2-BENZISOTHIAZOL-3-YL-PIPERAZIN-1-YL)-ETHYL]-PHENYL}-BUTYRAMIDE

Isolated in 100% purity @ 254 nm; LCMS (APCI): 409 $[M+H]^+$

Example 242

THIOPHENE-2-CARBOXYLIC ACID {3-[2-(4-1,2-BENZISOTHIAZOL-3-YL-PIPERAZIN-1-YL)-ETHYL]-PHENYL}-AMIDE

Isolated in 97% purity @ 254 nm; LCMS (APCI): 449 $[M+H]^+$

Example 243

N-{3-[2-(4-1,2-BENZISOTHIAZOL-3-YL-PIPERAZIN-1-YL)-ETHYL]-PHENYL}-ISOBUTYRAMIDE

Isolated in 93% purity @ 254 nm; LCMS (APCI): 409 $[M+H]^+$

Example 244

1-ACETYL-PIPERIDINE-4-CARBOXYLIC ACID {3-[2-(4-1,2-BENZISOTHIAZOL-3-YL-PIPERAZIN-1-YL)-ETHYL]-PHENYL}-AMIDE

Isolated in 96% purity @ 254 nm; LCMS (APCI): 492 $[M+H]^+$

Example 245

QUINOXALINE-2-CARBOXYLIC ACID {3-[2-(4-1,2-BENZISOTHIAZOL-3-YL-PIPERAZIN-1-YL)-ETHYL]-PHENYL}-AMIDE

Isolated in 97% purity @ 254 nm; LCMS (APCI): 495 $[M+H]^+$

Example 246

5-CHLORO-1-METHYL-1H-PYRAZOLE-4-CARBOXYLIC ACID {3-[2-(4-1,2-BENZISOTHIAZOL-3-YL-PIPERAZIN-1-YL)-ETHYL]-PHENYL}-AMIDE

Isolated in 92% purity @ 254 nm; LCMS (APCI): 482 $[M+H]^+$

Example 247

5-TERT-BUTYL-2-METHYL-2H-PYRAZOLE-3-CARBOXYLIC ACID {3-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 503 $[M+H]^+$

Example 248

4-METHYL-1,2,3-THIADIAZOLE-5-CARBOXYLIC ACID {3-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 465 $[M+H]^+$

Example 249

5-METHYL-2-PHENYL-2H-1,2,3-TRIAZOLE-4-CARBOXYLIC ACID {3-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 523 $[M+H]^+$

Example 250

{2-[2-(4-1,2-BENZISOTHIAZOL-3-YL-PIPERAZIN-1-YL)-ETHYL]-PHENYL}-CARBAMIC ACID 2-METHOXY-ETHYL ESTER

Isolated in 99% purity @ 254 nm; LCMS (APCI): 441 $[M+H]^+$

Example 251

{2-[2-(4-1,2-BENZISOTHIAZOL-3-YL-PIPERAZIN-1-YL)-ETHYL]-PHENYL}-CARBAMIC ACID PROPYL ESTER

Isolated in 100% purity @ 254 nm; LCMS (APCI): 425 $[M+H]^+$

Example 252

{2-[2-(4-1,2-BENZISOTHIAZOL-3-YL-PIPERAZIN-1-YL)-ETHYL]-PHENYL}-CARBAMIC ACID BENZYL ESTER

Isolated in 90% purity @ 254 nm; LCMS (APCI): 473 $[M+H]^+$

Example 253

{2-[2-(4-1,2-BENZISOTHIAZOL-3-YL-PIPERAZIN-1-YL)-ETHYL]-PHENYL}-CARBAMIC ACID BUT-2-YNYL ESTER

Isolated in 92% purity @ 254 nm; LCMS (APCI): 435 $[M+H]^+$

Example 254

{2-[2-(4-1,2-BENZISOTHIAZOL-3-YL-PIPERAZIN-1-YL)-ETHYL]-PHENYL}-CARBAMIC ACID VINYL ESTER

Isolated in 100% purity @ 254 nm; LCMS (APCI): 409 $[M+H]^+$

Example 255

{2-[2-(4-1,2-BENZISOTHIAZOL-3-YL-PIPERAZIN-1-YL)-ETHYL]-PHENYL}-CARBAMIC ACID ISOBUTYL ESTER

Isolated in 90% purity @ 254 nm; LCMS (APCI): 439 $[M+H]^+$

Example 256

{2-[2-(4-1,2-BENZISOTHIAZOL-3-YL-PIPERAZIN-1-YL)-ETHYL]-PHENYL}-CARBAMIC ACID BUTYL ESTER

Isolated in 99% purity @ 254 nm; LCMS (APCI): 439 [M+H]+

Example 257

{2-[2-(4-1,2-BENZISOTHIAZOL-3-YL-PIPERAZIN-1-YL)-ETHYL]-PHENYL}-CARBAMIC ACID 2,2-DIMETHYL-PROPYL ESTER

Isolated in 100% purity @ 254 nm; LCMS (APCI): 453 $[M+H]^+$

Example 258

{3-[2-(4-1,2-BENZISOTHIAZOL-3-YL-PIPERAZIN-1-YL)-ETHYL]-PHENYL}-CARBAMIC ACID 2-METHOXY-ETHYL ESTER

Isolated in 91% purity @ 254 nm; LCMS (APCI): 441 $[M+H]^+$

Example 259

{3-[2-(4-1,2-BENZISOTHIAZOL-3-YL-PIPERAZIN-1-YL)-ETHYL]-PHENYL}-CARBAMIC ACID PROPYL ESTER

Isolated in 97% purity @ 254 nm; LCMS (APCI): 425 $[M+H]^+$

Example 260

{3-[2-(4-1,2-BENZISOTHIAZOL-3-YL-PIPERAZIN-1-YL)-ETHYL]-PHENYL}-CARBAMIC ACID BENZYL ESTER

Isolated in 100% purity @ 254 nm; LCMS (APCI): 473 $[M+H]^+$

Example 261

{3-[2-(4-1,2-BENZISOTHIAZOL-3-YL-PIPERAZIN-1-YL)-ETHYL]-PHENYL}-CARBAMIC ACID BUT-2-YNYL ESTER

Isolated in 91% purity @ 254 nm; LCMS (APCI): 435 $[M+H]^+$

Example 262

{3-[2-(4-1,2-BENZISOTHIAZOL-3-YL-PIPERAZIN-1-YL)-ETHYL]-PHENYL}-CARBAMIC ACID VINYL ESTER

Isolated in 89% purity @ 254 nm; LCMS (APCI): 409 $[M+H]^+$

Example 263

{3-[2-(4-1,2-BENZISOTHIAZOL-3-YL-PIPERAZIN-1-YL)-ETHYL]-PHENYL}-CARBAMIC ACID ISOBUTYL ESTER

Isolated in 100% purity @ 254 nm; LCMS (APCI): 439 $[M+H]^+$

Example 264

{3-[2-(4-1,2-BENZISOTHIAZOL-3-YL-PIPERAZIN-1-YL)-ETHYL]-PHENYL}-CARBAMIC ACID BUTYL ESTER

Isolated in 100% purity @ 254 nm; LCMS (APCI): 439 $[M+H]^+$

Example 265

{3-[2-(4-1,2-BENZISOTHIAZOL-3-YL-PIPERAZIN-1-YL)-ETHYL]-PHENYL}-CARBAMIC ACID 2,2-DIMETHYL-PROPYL ESTER

Isolated in 100% purity @ 254 nm; LCMS (APCI): 453 $[M+H]^+$

Example 266

N-{2-[2-(4-BENZO[D]ISOTHIAZOL-3-YL-PIPERAZIN-1-YL)-ETHYL]-PHENYL}-N-METHYL-ACETAMIDE

{2-[2-(4-Benzo[d]isothiazol-3-yl-piperazin-1-yl)-ethyl]-phenyl}-methyl-amine was diluted to 0.20 M with anhydrous dichloroethane, then delivered to an 8 mL vial via pipette (0.20 mmol). To the amine solution was added base (0.4 M triethylamine in dichloroethane, 0.40 mmol). Acetyl chloride was diluted to 0.20 M with dichloroethane, and added at rt (0.2 mmol). The reaction was shaken overnight at 50° C., then evaluated by MS. Polyamine scavenging resin was added (0.5 mmol). The solution was shaken overnight at rt, then filtered into an 8 mL vial. The reaction was concentrated using an HT-12 GeneVac, then purified by HPLC (30×100 mm ODS-A C(18) 5u column). N-{2-[2-(4-Benzo[d]isothiazol-3-yl-piperazin-1-yl)-ethyl]-phenyl}-N-methyl-acetamide was isolated in 100% purity @ 254 nm, LCMS (APCI): 479 $[M+H]^+$.

Example 267

N-{2-[2-(4-BENZO[D]ISOTHIAZOL-3-YL-PIPERAZIN-1-YL)-ETHYL]-PHENYL}-N-ISOPROPYL-ACETAMIDE

{2-[2-(4-Benzo[d]isothiazol-3-yl-piperazin-1-yl)-ethyl]-phenyl}-isopropyl-amine was diluted to 0.20 M with anhydrous dichloroethane, then delivered to an 8 mL vial via pipette (0.20 mmol). To the amine solution was added base (0.4 M triethylamine in dichloroethane, 0.40 mmol). Acetyl chloride was diluted to 0.20 M with dichloroethane, and added at rt (0.2 mmol). The reaction was shaken three days, with the temperature ramped from 50° C. to 85° C. An additional 0.20 mmol of acetyl chloride was added after the second day. Polyamine scavenging resin was added (0.5 mmol). The solution was shaken overnight at room temperature, and filtered into an 8 mL vial. The reaction was concentrated via HT-12 GeneVac, then purified by HPLC (30×100 mm ODS-A C(18) 5u column). N-{2-[2-(4-Benzo[d]isothiazol-3-yl-piperazin-1-yl)-ethyl]-phenyl}-N-isopropyl-acetamide was isolated in 100% purity @ 254 nm, LCMS (APCI): 423 $[M+H]^+$.

Example 268

1-{4-[2-(4-1,2-BENZISOTHIAZOL-3-YL-PIPERAZIN-1-YL)-ETHYL]-PHENYL}-3-ETHYL-UREA

4-[2-(4-Benzo[d]isothiazol-3-yl-piperazin-1-yl)-ethyl]-phenylamine was diluted to 0.5 M with anhydrous dichloromethane, then delivered to an 8 mL vial via pipette (0.20 mmol). Ethyl isocyanate was diluted to 0.5 M with anhydrous dichloromethane, and added to the amine solution at rt (0.20 mmol). The solution was stirred overnight at 60° C. The reaction was evaluated by MS, then concentrated via HT-12 GeneVac. Crude was purified by HPLC (30×100 mm ODS-A C(18) 5u column). 4-[2-(4-Benzo[d]isothiazol-3-yl-piperazin-1-yl)-ethyl]-phenylamine was isolated in 100% purity @ 254 nm; LCMS (APCI): 410 $[M+H]^+$.

The ureas/thioureas of Examples 269–335 were synthesized in combinatorial library format using 4-[2-(4-benzo[d]isothiazol-3-yl-piperazin-1-yl)-ethyl]-phenylamine, 3-[2-(4-benzo[d]isothiazol-3-yl-piperazin-1-yl)-ethyl]-phenylamine, or 2-[2-(4-benzo[d]isothiazol-3-yl-piperazin-1-yl)-ethyl]-phenylamine with appropriate isocyanate/isothiocyantate starting materials on a 0.15–0.20 mmol scale in dichloromethane or dichloroethane, following the steps as outlined in Example 268. The crude products were purified by HPLC (30×100 mm ODS-A C(18) 5u column).

Example 269

1-{4-[2-(4-1,2-BENZISOTHIAZOL-3-YL-PIPERAZIN-1-YL)-ETHYL]-PHENYL}-3-BUTYL-UREA

Isolated in 100% purity @ 254 nm; LCMS (APCI): 438 $[M+H]^+$

Example 270

1-{4-[2-(4-1,2-BENZISOTHIAZOL-3-YL-PIPERAZIN-1-YL)-ETHYL]-PHENYL}-3-CYCLOPENTYL-UREA

Isolated in 100% purity @ 254 nm; LCMS (APCI): 450 $[M+H]^+$

Example 271

1-{4-[2-(4-1,2-BENZISOTHIAZOL-3-YL-PIPERAZIN-1-YL)-ETHYL]-PHENYL}-3-O-TOLYL-UREA

Isolated in 100% purity @ 254 nm; LCMS (APCI): 472 $[M+H]^+$

Example 272

1-{4-[2-(4-1,2-BENZISOTHIAZOL-3-YL-PIPERAZIN-1-YL)-ETHYL]-PHENYL}-3-(4-FLUORO-PHENYL)-UREA

Isolated in 97% purity @ 254 nm; LCMS (APCI): 476 $[M+H]^+$

Example 273

1-{4-[2-(4-1,2-BENZISOTHIAZOL-3-YL-PIPERAZIN-1-YL)-ETHYL]-PHENYL}-3-ETHYL-THIOUREA

Isolated in 96% purity @ 254 nm; LCMS (APCI): 426 [M+H]+

Exampl 274

1-{4-[2-(4-1,2-BENZISOTHIAZOL-3-YL-PIPERAZIN-1-YL)-ETHYL]-PHENYL}-3-CYCLOPENTYL-THIOUREA

Isolated in 100% purity @ 254 nm; LCMS (APCI): 466 $[M+H]^+$

Example 275

1-{4-[2-(4-1,2-BENZISOTHIAZOL-3-YL-PIPERAZIN-1-YL)-ETHYL]-PHENYL}-3-ISOPROPYL-UREA

Isolated in 100% purity @ 254 nm; LCMS (APCI): 424 $[M+H]^+$

Example 276

1-{4-[2-(4-1,2-BENZISOTHIAZOL-3-YL-PIPERAZIN-1-YL)-ETHYL]-PHENYL}-3-(4-DIMETHYLAMINO-PHENYL)-UREA

Isolated in 97% purity @ 254 nm; LCMS (APCI): 501 $[M+H]^+$

Example 277

1-{4-[2-(4-1,2-BENZISOTHIAZOL-3-YL-PIPERAZIN-1-YL)-ETHYL]-PHENYL}-3-PENTYL-UREA

Isolated in 94% purity @ 254 nm; LCMS (APCI): 452 $[M+H]^+$

Example 278

1-{4-[2-(4-1,2-BENZISOTHIAZOL-3-YL-PIPERAZIN-1-YL)-ETHYL]-PHENYL}-3-(2-PHENYL-CYCLOPROPYL)-UREA

Isolated in 100% purity @ 254 nm; LCMS (APCI): 498 $[M+H]^+$

Example 279

1-{4-[2-(4-1,2-BENZISOTHIAZOL-3-YL-PIPERAZIN-1-YL)-ETHYL]-PHENYL}-3-SEC-BUTYL-UREA

Isolated in 100% purity @ 254 nm; LCMS (APCI): 438 $[M+H]^+$

Example 280

1-{4-[2-(4-1,2-BENZISOTHIAZOL-3-YL-PIPERAZIN-1-YL)-ETHYL]-PHENYL}-3-METHYL-THIOUREA

Isolated in 93% purity @ 254 nm; LCMS (APCI): 412 $[M+H]^+$

Example 281

1-{4-[2-(4-1,2-BENZISOTHIAZOL-3-YL-PIPERAZIN-1-YL)-ETHYL]-PHENYL}-3-PROPYL-THIOUREA

Isolated in 100% purity @ 254 nm; LCMS (APCI): 440 $[M+H]^+$

Example 282

1-{4-[2-(4-1,2-BENZISOTHIAZOL-3-YL-PIPERAZIN-1-YL)-ETHYL]-PHENYL}-3-BUTYL-THIOUREA

Isolated in 100% purity @ 254 nm; LCMS (APCI): 454 $[M+H]^+$

Example 283

1-{4-[2-(4-1,2-BENZISOTHIAZOL-3-YL-PIPERAZIN-1-YL)-ETHYL]-PHENYL}-3-P-TOLYL-UREA

Isolated in 100% purity @ 254 nm; LCMS (APCI): 472 $[M+H]^+$

Example 284

1-{4-[2-(4-1,2-BENZISOTHIAZOL-3-YL-PIPERAZIN-1-YL)-ETHYL]-PHENYL}-3-(2-METHOXY-ETHYL)-THIOUREA

Isolated in 100% purity @ 254 nm; LCMS (APCI): 456 $[M+H]^+$

Example 285

1-{4-[2-(4-1,2-BENZISOTHIAZOL-3-YL-PIPERAZIN-1-YL)-ETHYL]-PHENYL}-3-PHENYL-THIOUREA

Isolated in 96% purity @ 254 nm; LCMS (APCI): 474 $[M+H]^+$

Example 286

1-{4-[2-(4-1,2-BENZISOTHIAZOL-3-YL-PIPERAZIN-1-YL)-ETHYL]-PHENYL}-3-(3-METHOXY-PHENYL)-UREA

Isolated in 100% purity @ 254 nm; LCMS (APCI): 488 [M+H]+

Example 287

1-ALLYL-3-{4-[2-(4-1,2-BENZISOTHIAZOL-3-YL-PIPERAZIN-1-YL)-ETHYL]-PHENYL}-UREA

Isolated in 100% purity @ 254 nm; LCMS (APCI): 422 $[M+H]^+$

Example 288

1-{4-[2-(4-1,2-BENZISOTHIAZOL-3-YL-PIPERAZIN-1-YL)-ETHYL]-PHENYL}-3-ISOPROPYL-UREA

Isolated in 99% purity @ 254 nm; LCMS (APCI): 424 $[M+H]^+$

Example 289

1-{4-[2-(4-1,2-BENZISOTHIAZOL-3-YL-PIPERAZIN-1-YL)-ETHYL]-PHENYL}-3-(2-FLUORO-PHENYL)-UREA

Isolated in 100% purity @ 254 nm; LCMS (APCI): 476 $[M+H]^+$

Example 290

1-{4-[2-(4-1,2-BENZISOTHIAZOL-3-YL-PIPERAZIN-1-YL)-ETHYL]-PHENYL}-3-BENZYL-UREA

Isolated in 100% purity @ 254 nm; LCMS (APCI): 472 $[M+H]^+$

Example 291

1-{4-[2-(4-1,2-BENZISOTHIAZOL-3-YL-PIPERAZIN-1-YL)-ETHYL]-PHENYL}-3-(3-CYANO-PHENYL)-UREA

Isolated in 100% purity @ 254 nm; LCMS (APCI): 483 $[M+H]^+$

Example 292

1-{2-[2-(4-1,2-BENZISOTHIAZOL-3-YL-PIPERAZIN-1-YL)-ETHYL]-PHENYL}-3-CYCLOPENTYL-UREA

Isolated in 100% purity @ 254 nm; LCMS (APCI): 450 $[M+H]^+$

Example 293

1-{2-[2-(4-1,2-BENZISOTHIAZOL-3-YL-PIPERAZIN-1-YL)-ETHYL]-PHENYL}-3-O-TOLYL-UREA

Isolated in 96% purity @ 254 nm; LCMS (APCI): 472 $[M+H]^+$

Example 294

1-{2-[2-(4-1,2-BENZISOTHIAZOL-3-YL-PIPERAZIN-1-YL)-ETHYL]-PHENYL}-3-(4-FLUORO-PHENYL)-UREA

Isolated in 95% purity @ 254 nm; LCMS (APCI): 476 $[M+H]^+$

Example 295

1-{2-[2-(4-1,2-BENZISOTHIAZOL-3-YL-PIPERAZIN-1-YL)-ETHYL]-PHENYL}-3-ETHYL-THIOUREA

Isolated in 100% purity @ 254 nm; LCMS (APCI): 426 $[M+H]^+$

Example 296

1-{2-[2-(4-1,2-BENZISOTHIAZOL-3-YL-PIPERAZIN-1-YL)-ETHYL]-PHENYL}-3-CYCLOPENTYL-THIOUREA

Isolated in 97% purity @ 254 nm; LCMS (APCI): 466 $[M+H]^+$

Example 297

1-{2-[2-(4-1,2-BENZISOTHIAZOL-3-YL-PIPERAZIN-1-YL)-ETHYL]-PHENYL}-3-ETHYL-UREA

Isolated in 100% purity @ 254 nm; LCMS (APCI): 410 $[M+H]^+$

Example 298

1-{2-[2-(4-1,2-BENZISOTHIAZOL-3-YL-PIPERAZIN-1-YL)-ETHYL]-PHENYL}-3-BUTYL-UREA

Isolated in 100% purity @ 254 nm; LCMS (APCI): 438 $[M+H]^+$

Example 299

1-{2-[2-(4-1,2-BENZISOTHIAZOL-3-YL-PIPERAZIN-1-YL)-ETHYL]-PHENYL}-3-P-TOLYL-UREA

Isolated in 96% purity @ 254 nm; LCMS (APCI): 472 $[M+H]^+$

Example 300

1-{2-[2-(4-1,2-BENZISOTHIAZOL-3-YL-PIPERAZIN-1-YL)-ETHYL]-PHENYL}-3-(3-METHOXY-PHENYL)-UREA

Isolated in 92% purity @ 254 nm; LCMS (APCI): 488 $[M+H]^+$

Example 301

1-ALLYL-3-{2-[2-(4-1,2-BENZISOTHIAZOL-3-YL-PIPERAZIN-1-YL)-ETHYL]-PHENYL}-UREA

Isolated in 98% purity @ 254 nm; LCMS (APCI): 422 $[M+H]^+$

Example 302

1-{2-[2-(4-1,2-BENZISOTHIAZOL-3-YL-PIPERAZIN-1-YL)-ETHYL]-PHENYL}-3-ISOPROPYL-UREA

Isolated in 98% purity @ 254 nm; LCMS (APCI): 424 $[M+H]^+$

Example 303

1-{2-[2-(4-1,2-BENZISOTHIAZOL-3-YL-PIPERAZIN-1-YL)-ETHYL]-PHENYL}-3-(2-FLUORO-PHENYL)-UREA

Isolated in 97% purity @ 254 nm; LCMS (APCI): 476 $[M+H]^+$

Example 304

1-{2-[2-(4-1,2-BENZISOTHIAZOL-3-YL-PIPERAZIN-1-YL)-ETHYL]-PHENYL}-3-BENZYL-UREA

Isolated in 100% purity @ 254 nm; LCMS (APCI): 472 $[M+H]^+$

Example 305

1-{2-[2-(4-1,2-BENZISOTHIAZOL-3-YL-PIPERAZIN-1-YL)-ETHYL]-PHENYL}-3-(3-CYANO-PHENYL)-UREA

Isolated in 94% purity @ 254 nm; LCMS (APCI): 483 $[M+H]^+$

Example 306

1-{2-[2-(4-1,2-BENZISOTHIAZOL-3-YL-PIPERAZIN-1-YL)-ETHYL]-PHENYL}-3-(4-DIMETHYLAMINO-PHENYL)-UREA

Isolated in 90% purity @ 254 nm; LCMS (APCI): 501 $[M+H]^+$

Example 307

1-{2-[2-(4-1,2-BENZISOTHIAZOL-3-YL-PIPERAZIN-1-YL)-ETHYL]-PHENYL}-3-PENTYL-UREA

Isolated in 97% purity @ 254 nm; LCMS (APCI): 452 $[M+H]^+$

Example 308

1-{2-[2-(4-1,2-BENZISOTHIAZOL-3-YL-PIPERAZIN-1-YL)-ETHYL]-PHENYL}-3-(2-PHENYL-CYCLOPROPYL)-UREA

Isolated in 100% purity @ 254 nm; LCMS (APCI): 498 $[M+H]^+$

Example 309

1-{2-[2-(4-1,2-BENZISOTHIAZOL-3-YL-PIPERAZIN-1-YL)-ETHYL]-PHENYL}-3-SEC-BUTYL-UREA

Isolated in 93% purity @ 254 nm; LCMS (APCI): 438 $[M+H]^+$

Example 310

1-{2-[2-(4-1,2-BENZISOTHIAZOL-3-YL-PIPERAZIN-1-YL)-ETHYL]-PHENYL}-3-PROPYL-THIOUREA

Isolated in 95% purity @ 254 nm; LCMS (APCI): 440 $[M+H]^+$

Example 311

1-{2-[2-(4-1,2-BENZISOTHIAZOL-3-YL-PIPERAZIN-1-YL)-ETHYL]-PHENYL}-3-(2-METHOXY-ETHYL)-THIOUREA

Isolated in 99% purity @ 254 nm; LCMS (APCI): 456 $[M+H]^+$

Example 312

3-(3-{2-[2-(4-1,2-BENZISOTHIAZOL-3-YL-PIPERAZIN-1-YL)-ETHYL]-PHENYL}-UREIDO)-PROPIONIC ACID ETHYL ESTER

Isolated in 98% purity @ 254 nm; LCMS (APCI): 482 [M+H]+

Example 313

1-{3-[2-(4-1,2-BENZISOTHIAZOL-3-YL-PIPERAZIN-1-YL)-ETHYL]-PHENYL}-3-ETHYL-UREA

Isolated in 100% purity @ 254 nm; LCMS (APCI): 410 $[M+H]^+$

Example 314

1-{3-[2-(4-1,2-BENZISOTHIAZOL-3-YL-PIPERAZIN-1-YL)-ETHYL]-PHENYL}-3-BUTYL-UREA

Isolated in 100% purity @ 254 nm; LCMS (APCI): 438 $[M+H]^+$

Example 315

1-{3-[2-(4-1,2-BENZISOTHIAZOL-3-YL-PIPERAZIN-1-YL)-ETHYL]-PHENYL}-3-CYCLOPENTYL-UREA

Isolated in 100% purity @ 254 nm; LCMS (APCI): 450 $[M+H]^+$

Example 316

1-{3-[2-(4-1,2-BENZISOTHIAZOL-3-YL-PIPERAZIN-1-YL)-ETHYL]-PHENYL}-3-O-TOLYL-UREA

Isolated in 100% purity @ 254 nm; LCMS (APCI): 472 $[M+H]^+$

Example 317

1-{3-[2-(4-1,2-BENZISOTHIAZOL-3-YL-PIPERAZIN-1-YL)-ETHYL]-PHENYL}-3-(4-FLUORO-PHENYL)-UREA

Isolated in 97% purity @ 254 nm; LCMS (APCI): 476 $[M+H]^+$

Example 318

1-{3-[2-(4-1,2-BENZISOTHIAZOL-3-YL-PIPERAZIN-1-YL)-ETHYL]-PHENYL}-3-ETHYL-THIOUREA

Isolated in 100% purity @ 254 nm; LCMS (APCI): 426 $[M+H]^+$

Example 319

1-{3-[2-(4-1,2-BENZISOTHIAZOL-3-YL-PIPERAZIN-1-YL)-ETHYL]-PHENYL}-3-CYCLOPENTYL-THIOUREA

Isolated in 100% purity @ 254 nm; LCMS (APCI): 466 $[M+H]^+$

Example 320

1-{3-[2-(4-1,2-BENZISOTHIAZOL-3-YL-PIPERAZIN-1-YL)-ETHYL]-PHENYL}-3-PROPYL-UREA

Isolated in 93% purity @ 254 nm; LCMS (APCI): 424 $[M+H]^+$

Example 321

1-{3-[2-(4-1,2-BENZISOTHIAZOL-3-YL-PIPERAZIN-1-YL)-ETHYL]-PHENYL}-3-P-TOLYL-UREA

Isolated in 90% purity @ 254 nm; LCMS (APCI): 472 $[M+H]^+$

Example 322

1-{3-[2-(4-1,2-BENZISOTHIAZOL-3-YL-PIPERAZIN-1-YL)-ETHYL]-PHENYL}-3-(3-METHOXY-PHENYL)-UREA

Isolated in 94% purity @ 254 nm; LCMS (APCI): 488 $[M+H]^+$

Example 323

1-ALLYL-3-{3-[2-(4-1,2-BENZISOTHIAZOL-3-YL-PIPERAZIN-1-YL)-ETHYL]-PHENYL}-UREA

Isolated in 100% purity @ 254 nm; LCMS (APCI): 422 $[M+H]^+$

Example 324

1-{3-[2-(4-1,2-BENZISOTHIAZOL-3-YL-PIPERAZIN-1-YL)-ETHYL]-PHENYL}-3-ISOPROPYL-UREA

Isolated in 100% purity @ 254 nm; LCMS (APCI): 424 $[M+H]^+$

Example 325

1-{3-[2-(4-1,2-BENZISOTHIAZOL-3-YL-PIPERAZIN-1-YL)-ETHYL]-PHENYL}-3-(2-FLUORO-PHENYL)-UREA

Isolated in 96% purity @ 254 nm; LCMS (APCI): 476 [M+H]+

Exampl 326

1-{3-[2-(4-1,2-BENZISOTHIAZOL-3-YL-PIPERAZIN-1-YL)-ETHYL]-PHENYL}-3-BENZYL-UREA

Isolated in 97% purity @ 254 nm; LCMS (APCI): 472 $[M+H]^+$

Example 327

1-{3-[2-(4-1,2-BENZISOTHIAZOL-3-YL-PIPERAZIN-1-YL)-ETHYL]-PHENYL}-3-(3-CYANO-PHENYL)-UREA

Isolated in 96% purity @ 254 nm; LCMS (APCI): 483 $[M+H]^+$

Example 328

1-{3-[2-(4-1,2-BENZISOTHIAZOL-3-YL-PIPERAZIN-1-YL)-ETHYL]-PHENYL}-3-PENTYL-UREA

Isolated in 92% purity @ 254 nm; LCMS (APCI): 458 $[M+H]^+$

Example 329

1-{3-[2-(4-1,2-BENZISOTHIAZOL-3-YL-PIPERAZIN-1-YL)-ETHYL]-PHENYL}-3-(2-PHENYL-CYCLOPROPYL)-UREA

Isolated in 100% purity @ 254 nm; LCMS (APCI): 498 $[M+H]^+$

Example 330

1-{(3-[2-(4-1,2-BENZISOTHIAZOL-3-YL-PIPERAZIN-1-YL)-ETHYL]-PHENYL}-3-SEC-BUTYL-UREA

Isolated in 92% purity @ 254 nm; LCMS (APCI): 438 $[M+H]^+$

Example 331

1-{3-[2-(4-1,2-BENZISOTHIAZOL-3-YL-PIPERAZIN-1-YL)-ETHYL]-PHENYL}-3-METHYL-THIOUREA

Isolated in 91% purity @ 254 nm; LCMS (APCI): 412 $[M+H]^+$

Example 332

1-{3-[2-(4-1,2-BENZISOTHIAZOL-3-YL-PIPERAZIN-1-YL)-ETHYL]-PHENYL}-3-PROPYL-THIOUREA

Isolated in 100% purity @ 254 nm; LCMS (APCI): 440 $[M+H]^+$

Example 333

1-{3-[2-(4-1,2-BENZISOTHIAZOL-3-YL-PIPERAZIN-1-YL)-ETHYL]-PHENYL}-3-BUTYL-THIOUREA

Isolated in 100% purity @ 254 nm; LCMS (APCI): 454 $[M+H]^+$

Example 334

1-{3-[2-(4-1,2-BENZISOTHIAZOL-3-YL-PIPERAZIN-1-YL)-ETHYL]-PHENYL}-3-(2-METHOXY-ETHYL)-THIOUREA

Isolated in 100% purity @ 254 nm; LCMS (APCI): 456 $[M+H]^+$

Example 335

3-(3-{3-[2-(4-1,2-BENZISOTHIAZOL-3-YL-PIPERAZIN-1-YL)-ETHYL]-PHENYL}-UREIDO)-PROPIONIC ACID ETHYL ESTER

Isolated in 100% purity @ 254 nm; LCMS (APCI): 482 $[M+H]^+$

The ureas/thioureas of Examples 336–354 were synthesized in combinatorial library format using 4-[2-(4-benzo[d]isothiazol-3-yl-piperazin-1-yl)-ethyl]-2-methyl-phenylamine, {2-[2-(4-benzo[d]isothiazol-3-yl-piperazin-1-yl)-ethyl]-phenyl}-methyl-amine, or {2-[2-(4-benzo[d]isothiazol-3-yl-piperazin-1-yl)-ethyl]-phenyl}-isopropyl-amine with appropriate isocyanate starting materials on a 0.20 mmol scale in dichloroethane, following the steps as outlined in Example 268. The crude products were purified by HPLC (30×100 mm ODS-A C(18) 5u column).

Example 336

1-{4-[2-(4-BENZO[D]ISOTHIAZOL-3-YL-PIPERAZIN-1-YL)-ETHYL]-2-METHYL-PHENYL}-3-P-TOLYL-UREA

Isolated in 100% purity @ 254 nm; LCMS (APCI): 486 $[M+H]^+$

Example 337

1-{4-[2-(4-BENZO[D]ISOTHIAZOL-3-YL-PIPERAZIN-1-YL)-ETHYL]-2-METHYL-PHENYL}-3-(4-FLUORO-PHENYL)-UREA

Isolated in 100% purity @ 254 nm; LCMS (APCI): 490 $[M+H]^+$

Example 338

1-{4-[2-(4-BENZO[D]ISOTHIAZOL-3-YL-PIPERAZIN-1-YL)-ETHYL]-2-METHYL-PHENYL}-3-BENZYL-UREA

Isolated in 100% purity @ 254 nm; LCMS (APCI): 486 $[M+H]^+$

Example 339

1-{4-[2-(4-BENZO[D]ISOTHIAZOL-3-YL-PIPERAZIN-1-YL)-ETHYL]-2-METHYL-PHENYL}-3-PROPYL-UREA

Isolated in 100% purity @ 254 nm; LCMS (APCI): 438 $[M+H]^+$

Example 340

1-{4-[2-(4-BENZO[D]ISOTHIAZOL-3-YL-PIPERAZIN-1-YL)-ETHYL]-2-METHYL-PHENYL}-3-ISOPROPYL-UREA

Isolated in 100% purity @ 254 nm; LCMS (APCI): 438 $[M+H]^+$

Example 341

1-{4-[2-(4-BENZO[D]ISOTHIAZOL-3-YL-PIPERAZIN-1-YL)-ETHYL]-2-METHYL-PHENYL}-3-CYCLOPENTYL-UREA

Isolated in 100% purity @ 254 nm; LCMS (APCI): 464 $[M+H]^+$

Example 342

1-{2-[2-(4-BENZO[D]ISOTHIAZOL-3-YL-PIPERAZIN-1-YL)-ETHYL]-PHENYL}-1-ISOPROPYL-3-P-TOLYL-UREA

Isolated in 100% purity @ 254 nm; LCMS (APCI): 514 $[M+H]^+$

Example 343

1-{2-[2-(4-BENZO[D]ISOTHIAZOL-3-YL-PIPERAZIN-1-YL)-ETHYL]-PHENYL}-3-(4-FLUORO-PHENYL)-1-ISOPROPYL-UREA

Isolated in 100% purity @ 254 nm; LCMS (APCI): 518 [M+H]+

Example 344

1-{2-[2-(4-BENZO[D]ISOTHIAZOL-3-YL-PIPERAZIN-1-YL)-ETHYL]-PHENYL}-3-BENZYL-1-ISOPROPYL-UREA

Isolated in 100% purity @ 254 nm; LCMS (APCI): 514 $[M+H]^+$

Example 345

1-{2-[2-(4-BENZO[D]ISOTHIAZOL-3-YL-PIPERAZIN-1-YL)-ETHYL]-PHENYL}-1-ISOPROPYL-3-PROPYL-UREA

Isolated in 100% purity @ 254 nm; LCMS (APCI): 466 $[M+H]^+$

Example 346

1-{2-[2-(4-BENZO[D]ISOTHIAZOL-3-YL-PIPERAZIN-1-YL)-ETHYL]-PHENYL}-13-DIISOPROPYL-UREA

Isolated in 100% purity @ 254 nm; LCMS (APCI): 466 $[M+H]^+$

Example 347

1-{2-[2-(4-BENZO[D]ISOTHIAZOL-3-YL-PIPERAZIN-1-YL)-ETHYL]-PHENYL}-3-CYCLOPENTYL-1-ISOPROPYL-UREA

Isolated in 100% purity @ 254 nm; LCMS (APCI): 492 $[M+H]^+$

Example 348

1-{2-[2-(4-BENZO[D]ISOTHIAZOL-3-YL-PIPERAZIN-1-YL)-ETHYL]-PHENYL}-1-METHYL-3-PROPYL-THIOUREA

Isolated in 100% purity @ 254 nm; LCMS (APCI): 454 $[M+H]^+$

Example 349

1-{2-[2-(4-BENZO[D]ISOTHIAZOL-3-YL-PIPERAZIN-1-YL)-ETHYL]-PHENYL}-1-METHYL-3-P-TOLYL-UREA

Isolated in 100% purity @ 254 nm; LCMS (APCI): 486 $[M+H]^+$

Example 350

1-{2-[2-(4-BENZO[D]ISOTHIAZOL-3-YL-PIPERAZIN-1-YL)-ETHYL]-PHENYL}-3-(4-FLUORO-PHENYL)-1-METHYL-UREA

Isolated in 100% purity @ 254 nm; LCMS (APCI): 490 $[M+H]^+$

Example 351

1-{2-[2-(4-BENZO[D]ISOTHIAZOL-3-YL-PIPERAZIN-1-YL)-ETHYL]-PHENYL}-3-BENZYL-1-METHYL-UREA

Isolated in 100% purity @ 254 nm; LCMS (APCI): 486 $[M+H]^+$

Example 352

1-{2-[2-(4-BENZO[D]ISOTHIAZOL-3-YL-PIPERAZIN-1-YL)-ETHYL]-PHENYL}-1-METHYL-3-PROPYL-UREA

Isolated in 100% purity @ 254 nm; LCMS (APCI): 438 $[M+H]^+$

Example 353

1-{2-[2-(4-BENZO[D]ISOTHIAZOL-3-YL-PIPERAZIN-1-YL)-ETHYL]-PHENYL}-3-ISOPROPYL-1-METHYL-UREA

Isolated in 100% purity @ 254 nm; LCMS (APCI): 438 $[M+H]^+$

Example 354

1-{2-[2-(4-BENZO[D]ISOTHIAZOL-3-YL-PIPERAZIN-1-YL)-ETHYL]-PHENYL}-3-CYCLOPENTYL-1-METHYL-UREA

Isolated in 100% purity @ 254 nm; LCMS (APCI): 464 $[M+H]^+$

Example 355

PROPANE-1-SULFONIC ACID {4-[2-(4-1,2-BENZISOTHIAZOL-3-YL-PIPERAZIN-1-YL)-ETHYL]-PHENYL}-AMIDE

4-[2-(4-Benzo[d]isothiazol-3-yl-piperazin-1-yl)-ethyl]-phenylamine was diluted to 0.3 M with anhydrous pyridine, then delivered to an 8 mL vial via pipette (0.225 mmol). Propane-1-sulfonyl chloride was diluted to 1.0 M with anhydrous dichloromethane, and added to the amine solution at rt (0.40 mmol). The solution was stirred overnight at 45° C. To the reaction mixture was added polyamine scavenging resin (0.30 mmol). The solution was stirred overnight at 45° C., then filtered into an 8 mL vial. The filtrate was evaluated by MS and concentrated via HT-12 GeneVac. Crude was purified by HPLC (30×100 mm ODS-A C(18) 5u column). Propane-1-sulfonic acid {4-[2-(4-1,2-benzisothiazol-3-yl-piperazin-1-yl)-ethyl]-phenyl}-amide was isolated in 100% purity @ 254 nm; LCMS (APCI): 445 $[M+H]^+$ The sulfonamides of Examples 356–448 were synthesized in combinatorial library format using appropriate sulfonyl chloride starting materials and 4-[2-(4-benzo[d]isothiazol-3-yl-piperazin-1-yl)-ethyl]-phenylamine on a 0.225 mmol scale and following the steps as outlined in Example 355. The crude products were purified by HPLC (30×100 mm ODS-A C(18) 5u column).

Example 356

PROPANE-1-SULFONIC ACID {4-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 445 $[M+H]^+$

Example 357

N-{4-[2-(4-1,2-BENZISOTHIAZOL-3-YL-PIPERAZIN-1-YL)-ETHYL]-PHENYL}-C-PHENYL-METHANESULFONAMIDE

Isolated in 100% purity @ 254 nm; LCMS (APCI): 493 $[M+H]^+$

Example 358

THIOPHENE-2-SULFONIC ACID {4-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 485 $[M+H]^+$

Example 359

N-{4-[2-(4-1,2-BENZISOTHIAZOL-3-YL-PIPERAZIN-1-YL)-ETHYL]-PHENYL}-2-FLUORO-BENZENESULFONAMIDE

Isolated in 100% purity @ 254 nm; LCMS (APCI): 497 $[M+H]^+$

Example 360

3,5-DIMETHYL-ISOXAZOLE-4-SULFONIC ACID {4-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 498 $[M+H]^+$

Example 361

DIMETHYLSULFAMIC ACID {4-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 446 $[M+H]^+$

Example 362

N-{4-[2-(4-1,2-BENZISOTHIAZOL-3-YL-PIPERAZIN-1-YL)-ETHYL]-PHENYL}-3-METHYL-BENZENESULFONAMIDE

Isolated in 100% purity @ 254 nm; LCMS (APCI): 493 $[M+H]^+$

Example 363

N-{4-[2-(4-1,2-BENZISOTHIAZOL-3-YL-PIPERAZIN-1-YL)-ETHYL]-PHENYL}-C-METHANESULFONYL-METHANESULFONAMIDE

Isolated in 100% purity @ 254 nm; LCMS (APCI): 495 $[M+H]^+$

Example 364

N-{4-[2-(4-1,2-BENZISOTHIAZOL-3-YL-PIPERAZIN-1-YL)-ETHYL]-PHENYL}-3-METHOXY-BENZENESULFONAMIDE

Isolated in 100% purity @ 254 nm; LCMS (APCI): 509 $[M+H]^+$

Example 365

N-{4-[2-(4-1,2-BENZISOTHIAZOL-3-YL-PIPERAZIN-1-YL)-ETHYL]-PHENYL}-4-CYANO-BENZENESULFONAMIDE

Isolated in 100% purity @ 254 nm; LCMS (APCI): 504 $[M+H]^+$

Example 366

5-CHLORO-THIOPHENE-2-SULFONIC ACID {4-[2-(4-1,2-BENZISOTHIAZOL-3-YL-PIPERAZIN-1-YL)-ETHYL]-PHENYL}-AMIDE

Isolated in 87% purity @ 254 nm; LCMS (APCI): 520 $[M+H]^+$

Example 367

N-{4-[2-(4-1,2-BENZISOTHIAZOL-3-YL-PIPERAZIN-1-YL)-ETHYL]-PHENYL}-2,4-DIFLUORO-BENZENESULFONAMIDE

Isolated in 92% purity @ 254 nm; LCMS (APCI): 515 $[M+H]^+$

Example 368

N-{4-[2-(4-1,2-BENZISOTHIAZOL-3-YL-PIPERAZIN-1-YL)-ETHYL]-PHENYL}-2-CHLORO-BENZENESULFONAMIDE

Isolated in 100% purity @ 254 nm; LCMS (APCI): 514 $[M+H]^+$

Example 369

N-{4-[2-(4-1,2-BENZISOTHIAZOL-3-YL-PIPERAZIN-1-YL)-ETHYL]-PHENYL}-2,5-DIMETHOXY-BENZENESULFONAMIDE

Isolated in 96% purity @ 254 nm; LCMS (APCI): 539 $[M+H]^+$

Example 370

NAPHTHALENE-2-SULFONIC ACID {4-[2-(4-1,2-BENZISOTHIAZOL-3-YL-PIPERAZIN-1-YL)-ETHYL]-PHENYL}-AMIDE

Isolated in 98% purity @ 254 nm; LCMS (APCI): 529 $[M+H]^+$

Example 371

N-{4-[2-(4-1,2-BENZISOTHIAZOL-3-YL-PIPERAZIN-1-YL)-ETHYL]-PHENYL}-4-TERT-BUTYL-BENZENESULFONAMIDE

Isolated in 99% purity @ 254 nm; LCMS (APCI): 535 $[M+H]^+$

Example 372

N-{4-[2-(4-1,2-BENZISOTHIAZOL-3-YL-PIPERAZIN-1-YL)-ETHYL]-PHENYL}-4-CHLORO-BENZENESULFONAMIDE

Isolated in 98% purity @ 254 nm; LCMS (APCI): 514 $[M+H]^+$

Example 373

N-{4-[2-(4-1,2-BENZISOTHIAZOL-3-YL-PIPERAZIN-1-YL)-ETHYL]-PHENYL}-4-ISOPROPYL-BENZENESULFONAMIDE

Isolated in 95% purity @ 254 nm; LCMS (APCI): 521 $[M+H]^+$

Example 374

N-(4-{4-[2-(4-1,2-BENZISOTHIAZOL-3-YL-PIPERAZIN-1-YL)-ETHYL]-PHENYLSULFAMOYL}-PHENYL)-ACETAMIDE

Isolated in 95% purity @ 254 nm; LCMS (APCI): 536 $[M+H]^+$

Example 375

BUTANE-1-SULFONIC ACID {4-[2-(4-1,2-BENZISOTHIAZOL-3-YL-PIPERAZIN-1-YL)-ETHYL]-PHENYL}-AMIDE

Isolated in 96% purity @ 254 nm; LCMS (APCI): 459 $[M+H]^+$

Example 376

N-{4-[2-(4-1,2-BENZISOTHIAZOL-3-YL-PIPERAZIN-1-YL)-ETHYL]-PHENYL}-BENZENE-SULFONAMIDE

Isolated in 100% purity @ 254 nm; LCMS (APCI): 479 $[M+H]^+$

Example 377

N-{4-[2-(4-1,2-BENZISOTHIAZOL-3-YL-PIPERAZIN-1-YL)-ETHYL]-PHENYL}-3-NITRO-BENZENESULFONAMIDE

Isolated in 100% purity @ 254 nm; LCMS (APCI): 524 $[M+H]^+$

Example 378

QUINOLINE-8-SULFONIC ACID {4-[2-(4-1,2-BENZISOTHIAZOL-3-YL-PIPERAZIN-1-YL)-ETHYL]-PHENYL}-AMIDE

Isolated in 95% purity @ 254 nm; LCMS (APCI): 530 $[M+H]^+$

Example 379

N-{4-[2-(4-1,2-BENZISOTHIAZOL-3-YL-PIPERAZIN-1-YL)-ETHYL]-PHENYL}-3-TRIFLUOROMETHYL-BENZENESULFONAMIDE

Isolated in 99% purity @ 254 nm; LCMS (APCI): 547 $[M+H]^+$

Example 380

N-{4-[2-(4-1,2-BENZISOTHIAZOL-3-YL-PIPERAZIN-1-YL)-ETHYL]-PHENYL}-2-TRIFLUOROMETHYL-BENZENESULFONAMIDE

Isolated in 100% purity @ 254 nm; LCMS (APCI): 547 $[M+H]^+$

Example 381

ETHANESULFONIC ACID {4-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 431 $[M+H]^+$

Example 382

PROPANE-2-SULFONIC ACID {4-[2-(4-1,2-BENZISOTHIAZOL-3-YL-PIPERAZIN-1-YL)-ETHYL]-PHENYL}-AMIDE

Isolated in 98% purity @ 254 nm; LCMS (APCI): 445 $[M+H]^+$

Example 383

1,3,5-TRIMETHYL-1H-PYRAZOLE-4-SULFONIC ACID {4-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 511 $[M+H]^+$

Example 384

1,2-DIMETHYL-1H-IMIDAZOLE-4-SULFONIC ACID {4-[2-(4-1,2-BENZISOTHIAZOL-3-YL-PIPERAZIN-1-YL)-ETHYL]-PHENYL}-AMIDE

Isolated in 98% purity @ 254 nm; LCMS (APCI): 496 $[M+H]^+$

Example 385

N-{4-[2-(4-1,2-BENZISOTHIAZOL-3-YL-PIPERAZIN-1-YL)-ETHYL]-PHENYL}-4-METHYL-BENZENESULFONAMIDE

Isolated in 100% purity @ 254 nm; LCMS (APCI): 493 $[M+H]^+$

Example 386

N-{4-[2-(4-1,2-BENZISOTHIAZOL-3-YL-PIPERAZIN-1-YL)-ETHYL]-PHENYL}-4-NITRO-BENZENESULFONAMIDE

Isolated in 94% purity @ 254 nm; LCMS (APCI): 524 $[M+H]^+$

Example 387

N-{4-[2-(4-1,2-BENZISOTHIAZOL-3-YL-PIPERAZIN-1-YL)-ETHYL]-PHENYL}-4-FLUORO-BENZENESULFONAMIDE

Isolated in 100% purity @ 254 nm; LCMS (APCI): 497 $[M+H]^+$

Example 388

N-{4-[2-(4-1,2-BENZISOTHIAZOL-3-YL-PIPERAZIN-1-YL)-ETHYL]-PHENYL}-4-METHOXY-BENZENESULFONAMIDE

Isolated in 100% purity @ 254 nm; LCMS (APCI): 509 $[M+H]^+$

Example 389

N-{2-[2-(4-1,2-BENZISOTHIAZOL-3-YL-PIPERAZIN-1-YL)-ETHYL]-PHENYL}-2-FLUORO-BENZENESULFONAMIDE

Isolated in 100% purity @ 254 nm; LCMS (APCI): 497 $[M+H]^+$

Example 390

N-{2-[2-(4-1,2-BENZISOTHIAZOL-3-YL-PIPERAZIN-1-YL)-ETHYL]-PHENYL}-4-CHLORO-BENZENESULFONAMIDE

Isolated in 100% purity @ 254 nm; LCMS (APCI): 514 $[M+H]^+$

Example 391

N-{2-[2-(4-1,2-BENZISOTHIAZOL-3-YL-PIPERAZIN-1-YL)-ETHYL]-PHENYL}-4-ISOPROPYL-BENZENESULFONAMIDE

Isolated in 100% purity @ 254 nm; LCMS (APCI): 521 $[M+H]^+$

Example 392

DIMETHYLSULFAMIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 446 $[M+H]^+$

Example 393

N-(4-{2-[2-(4-1,2-BENZISOTHIAZOL-3-YL-PIPERAZIN-1-YL)-ETHYL]-PHENYLSULFAMOYL}-PHENYL)-ACETAMIDE

Isolated in 91% purity @ 254 nm; LCMS (APCI): 536 $[M+H]^+$

Example 394

BUTANE-1-SULFONIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 459 $[M+H]^+$

Example 395

N-{2-[2-(4-1,2-BENZISOTHIAZOL-3-YL-PIPERAZIN-1-YL)-ETHYL]-PHENYL}-BENZENESULFONAMIDE

Isolated in 100% purity @ 254 nm; LCMS (APCI): 479 $[M+H]^+$

Example 396

N-{2-[2-(4-1,2-BENZISOTHIAZOL-3-YL-PIPERAZIN-1-YL)-ETHYL]-PHENYL}-3-NITRO-BENZENESULFONAMIDE

Isolated in 100% purity @ 254 nm; LCMS (APCI): 524 $[M+H]^+$

Example 397

QUINOLINE-8-SULFONIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 530 $[M+H]^+$

Example 398

N-{2-[2-(4-1,2-BENZISOTHIAZOL-3-YL-PIPERAZIN-1-YL)-ETHYL]-PHENYL}-3,4-DIMETHOXY-BENZENESULFONAMIDE

Isolated in 93% purity @ 254 nm; LCMS (APCI): 539 $[M+H]^+$

Example 399

N-{2-[2-(4-1,2-BENZISOTHIAZOL-3-YL-PIPERAZIN-1-YL)-ETHYL]-PHENYL}-3-TRIFLUOROMETHYL-BENZENESULFONAMIDE

Isolated in 98% purity @ 254 nm; LCMS (APCI): 547 $[M+H]^+$

Example 400

N-{2-[2-(4-1,2-BENZISOTHIAZOL-3-YL-PIPERAZIN-1-YL)-ETHYL]-PHENYL}-2-TRIFLUOROMETHYL-BENZENESULFONAMIDE

Isolated in 100% purity @ 254 nm; LCMS (APCI): 547 $[M+H]^+$

Example 401

ETHANESULFONIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 431 $[M+H]^+$

Example 402

PROPANE-2-SULFONIC ACID {2-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 445 $[M+H]^+$

Example 403

1,3,5-TRIMETHYL-1H-PYRAZOLE-4-SULFONIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 511 $[M+H]^+$

Example 404

1,2-DIMETHYL-1H-IMIDAZOLE-4-SULFONIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 497 $[M+H]^+$

Example 405

N-{2-[2-(4-1,2-BENZISOTHIAZOL-3-YL-PIPERAZIN-1-YL)-ETHYL]-PHENYL}-4-CYANO-BENZENESULFONAMIDE

Isolated in 100% purity @ 254 nm; LCMS (APCI): 504 $[M+H]^+$

Example 406

N-{2-[2-(4-1,2-BENZISOTHIAZOL-3-YL-PIPERAZIN-1-YL)-ETHYL]-PHENYL}-4-NITRO-BENZENESULFONAMIDE

Isolated in 100% purity @ 254 nm; LCMS (APCI): 524 $[M+H]^+$

Example 407

N-{2-[2-(4-1,2-BENZISOTHIAZOL-3-YL-PIPERAZIN-1-YL)-ETHYL]-PHENYL}-4-FLUORO-BENZENESULFONAMIDE

Isolated in 97% purity @ 254 nm; LCMS (APCI): 497 $[M+H]^+$

Example 408

N-{2-[2-(4-1,2-BENZISOTHIAZOL-3-YL-PIPERAZIN-1-YL)-ETHYL]-PHENYL}-4-METHOXY-BENZENESULFONAMIDE

Isolated in 100% purity @ 254 nm; LCMS (APCI): 509 $[M+H]^+$

Example 409

3,5-DIMETHYL-ISOXAZOLE-4-SULFONIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 498 $[M+H]^+$

Example 410

N-{2-[2-(4-1,2-BENZISOTHIAZOL-3-YL-PIPERAZIN-1-YL)-ETHYL]-PHENYL}-3-METHYL-BENZENESULFONAMIDE

Isolated in 100% purity @ 254 nm; LCMS (APCI): 493 $[M+H]^+$

Example 411

5-CHLORO-THIOPHENE-2-SULFONIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 520 $[M+H]^+$

Example 412

N-{2-[2-(4-1,2-BENZISOTHIAZOL-3-YL-PIPERAZIN-1-YL)-ETHYL]-PHENYL}-2,4-DIFLUORO-BENZENESULFONAMIDE

Isolated in 100% purity @ 254 nm; LCMS (APCI): 515 $[M+H]^+$

Example 413

N-{2-[2-(4-1,2-BENZISOTHIAZOL-3-YL-PIPERAZIN-1-YL)-ETHYL]-PHENYL}-2-CHLORO-BENZENESULFONAMIDE

Isolated in 92% purity @ 254 nm; LCMS (APCI): 514 $[M+H]^+$

Example 414

N-{2-[2-(4-1,2-BENZISOTHIAZOL-3-YL-PIPERAZIN-1-YL)-ETHYL]-PHENYL}-3-METHOXY-BENZENESULFONAMIDE

Isolated in 100% purity @ 254 nm; LCMS (APCI): 509 $[M+H]^+$

Example 415

THIOPHENE-2-SULFONIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 485 $[M+H]^+$

Example 416

N-{2-[2-(4-1,2-BENZISOTHIAZOL-3-YL-PIPERAZIN-1-YL)-ETHYL]-PHENYL}-2,5-DIMETHOXY-BENZENESULFONAMIDE

Isolated in 100% purity @ 254 nm; LCMS (APCI): 539 $[M+H]^+$

Example 417

NAPHTHALENE-2-SULFONIC ACID {2-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 529 $[M+H]^+$

Example 418

N-{2-[2-(4-1,2-BENZISOTHIAZOL-3-YL-PIPERAZIN-1-YL)-ETHYL]-PHENYL}-4-TERT-BUTYL-BENZENESULFONAMIDE

Isolated in 100% purity @ 254 nm; LCMS (APCI): 535 $[M+H]^+$

Example 419

PROPANE-1-SULFONIC ACID {2-[2-(4-1,2-BENZISOTHIAZOL-3-YL-PIPERAZIN-1-YL)-ETHYL]-PHENYL}-AMIDE

Isolated in 98% purity @ 254 nm; LCMS (APCI): 445 $[M+H]^+$

Example 420

N-{3-[2-(4-1,2-BENZISOTHIAZOL-3-YL-PIPERAZIN-1-YL)-ETHYL]-PHENYL}-4-CYANO-BENZENESULFONAMIDE

Isolated in 100% purity @ 254 nm; LCMS (APCI): 504 $[M+H]^+$

Example 421

N-{3-[2-(4-1,2-BENZISOTHIAZOL-3-YL-PIPERAZIN-1-YL)-ETHYL]-PHENYL}-4-NITRO-BENZENESULFONAMIDE

Isolated in 97% purity @ 254 nm; LCMS (APCI): 524 $[M+H]^+$

Example 422

N-{3-[2-(4-1,2-BENZISOTHIAZOL-3-YL-PIPERAZIN-1-YL)-ETHYL]-PHENYL}-4-FLUORO-BENZENESULFONAMIDE

Isolated in 98% purity @ 254 nm; LCMS (APCI): 497 $[M+H]^+$

Example 423

N-{3-[2-(4-1,2-BENZISOTHIAZOL-3-YL-PIPERAZIN-1-YL)-ETHYL]-PHENYL}-4-METHOXY-BENZENESULFONAMIDE

Isolated in 98% purity @ 254 nm; LCMS (APCI): 509 $[M+H]^+$

Example 424

3,5-DIMETHYL-ISOXAZOLE-4-SULFONIC ACID {3-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 498 $[M+H]^+$

Example 425

N-{3-[2-(4-1,2-BENZISOTHIAZOL-3-YL-PIPERAZIN-1-YL)-ETHYL]-PHENYL}-3-METHYL-BENZENESULFONAMIDE

Isolated in 98% purity @ 254 nm; LCMS (APCI): 493 $[M+H]^+$

Example 426

N-{3-[2-(4-1,2-BENZISOTHIAZOL-3-YL-PIPERAZIN-1-YL)-ETHYL]-PHENYL}-2,4-DIFLUORO-BENZENESULFONAMIDE

Isolated in 98% purity @ 254 nm; LCMS (APCI): 515 $[M+H]^+$

Example 427

N-{3-[2-(4-1,2-BENZISOTHIAZOL-3-YL-PIPERAZIN-1-YL)-ETHYL]-PHENYL}-2-CHLORO-BENZENESULFONAMIDE

Isolated in 100% purity @ 254 nm; LCMS (APCI): 514 $[M+H]^+$

Example 428

N-{3-[2-(4-1,2-BENZISOTHIAZOL-3-YL-PIPERAZIN-1-YL)-ETHYL]-PHENYL}-3-METHOXY-BENZENESULFONAMIDE

Isolated in 100% purity @ 254 nm; LCMS (APCI): 509 $[M+H]^+$

Example 429

THIOPHENE-2-SULFONIC ACID {3-[2-(4-1,2-BENZISOTHIAZOL-3-YL-PIPERAZIN-1-YL)-ETHYL]-PHENYL}-AMIDE

Isolated in 96% purity @ 254 nm; LCMS (APCI): 485 $[M+H]^+$

Example 430

N-{3-[2-(4-1,2-BENZISOTHIAZOL-3-YL-PIPERAZIN-1-YL)-ETHYL]-PHENYL}-2,5-DIMETHOXY-BENZENESULFONAMIDE

Isolated in 98% purity @ 254 nm; LCMS (APCI): 539 $[M+H]^+$

Example 431

NAPHTHALENE-2-SULFONIC ACID {3-[2-(4-1,2-BENZISOTHIAZOL-3-YL-PIPERAZIN-1-YL)-ETHYL]-PHENYL}-AMIDE

Isolated in 98% purity @ 254 nm; LCMS (APCI): 529 $[M+H]^+$

Example 432

N-{3-[2-(4-1,2-BENZISOTHIAZOL-3-YL-PIPERAZIN-1-YL)-ETHYL]-PHENYL}-4-TERT-BUTYL-BENZENESULFONAMIDE

Isolated in 98% purity @ 254 nm; LCMS (APCI): 535 $[M+H]^+$

Example 433

PROPANE-1-SULFONIC ACID {3-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 445 $[M+H]^+$

Example 434

N-{3-[2-(4-1,2-BENZISOTHIAZOL-3-YL-PIPERAZIN-1-YL)-ETHYL]-PHENYL}-2-FLUORO-BENZENESULFONAMIDE

Isolated in 98% purity @ 254 nm; LCMS (APCI): 497 $[M+H]^+$

Example 435

N-{3-[2-(4-1,2-BENZISOTHIAZOL-3-YL-PIPERAZIN-1-YL)-ETHYL]-PHENYL}-4-CHLORO-BENZENESULFONAMIDE

Isolated in 98% purity @ 254 nm; LCMS (APCI): 514 $[M+H]^+$

Example 436

N-{3-[2-(4-1,2-BENZISOTHIAZOL-3-YL-PIPERAZIN-1-YL)-ETHYL]-PHENYL}-4-ISOPROPYL-BENZENESULFONAMIDE

Isolated in 98% purity @ 254 nm; LCMS (APCI): 521 $[M+H]^+$

Example 437

DIMETHYLSULFAMIC ACID {3-[2-(4-1,2-BENZISOTHIAZOL-3-YL-PIPERAZIN-1-YL)-ETHYL]-PHENYL}-AMIDE

Isolated in 98% purity @ 254 nm; LCMS (APCI): 446 $[M+H]^+$

Exampl 438

BUTANE-1-SULFONIC ACID {3-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 459 $[M+H]^+$

Example 439

N-{3-[2-(4-1,2-BENZISOTHIAZOL-3-YL-PIPERAZIN-1-YL)-ETHYL]-PHENYL}-BENZENE-SULFONAMIDE

Isolated in 100% purity @ 254 nm; LCMS (APCI): 479 $[M+H]^+$

Example 440

N-{3-[2-(4-1,2-BENZISOTHIAZOL-3-YL-PIPERAZIN-1-YL)-ETHYL]-PHENYL}-3-NITRO-BENZENESULFONAMIDE

Isolated in 100% purity @ 254 nm; LCMS (APCI): 524 $[M+H]^+$

Example 441

QUINOLINE-8-SULFONIC ACID {3-[2-(4-1,2-BENZISOTHIAZOL-3-YL-PIPERAZIN-1-YL)-ETHYL]-PHENYL}-AMIDE

Isolated in 98% purity @ 254 nm; LCMS (APCI): 530 $[M+H]^+$

Example 442

N-{3-[2-(4-1,2-BENZISOTHIAZOL-3-YL-PIPERAZIN-1-YL)-ETHYL]-PHENYL}-3,4-DIMETHOXY-BENZENESULFONAMIDE

Isolated in 98% purity @ 254 nm; LCMS (APCI): 539 $[M+H]^+$

Example 443

N-{3-[2-(4-1,2-BENZISOTHIAZOL-3-YL-PIPERAZIN-1-YL)-ETHYL]-PHENYL}-3-TRIFLUOROMETHYL-BENZENESULFONAMIDE

Isolated in 97% purity @ 254 nm; LCMS (APCI): 547 $[M+H]^+$

Example 444

N-{3-[2-(4-1,2-BENZISOTHIAZOL-3-YL-PIPERAZIN-1-YL)-ETHYL]-PHENYL}-2-TRIFLUOROMETHYL-BENZENESULFONAMIDE

Isolated in 99% purity @ 254 nm; LCMS (APCI): 547 $[M+H]^+$

Example 445

ETHANESULFONIC ACID {3-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 431 $[M+H]^+$

Example 446

PROPANE-2-SULFONIC ACID {3-[2-(4-1,2-BENZISOTHIAZOL-3-YL-PIPERAZIN-1-YL)-ETHYL]-PHENYL}-AMIDE

Isolated in 100% purity @ 254 nm; LCMS (APCI): 445 $[M+H]^+$

Example 447

1,3,5-TRIMETHYL-1H-PYRAZOLE-4-SULFONIC ACID {3-[2-(4-1,2-BENZISOTHIAZOL-3-YL-PIPERAZIN-1-YL)-ETHYL]-PHENYL}-AMIDE

Isolated in 98% purity @ 254 nm; LCMS (APCI): 511 $[M+H]^+$

Example 448

1,2-DIMETHYL-1H-IMIDAZOLE-4-SULFONIC ACID {3-[2-(4-1,2-BENZISOTHIAZOL-3-YL-PIPERAZIN-1-YL)-ETHYL]-PHENYL}-AMIDE

Isolated in 99% purity @ 254 nm; LCMS (APCI): 497 $[M+H]^+$

The sulfonamides of Examples 449–499 were synthesized in combinatorial library format using 4-[2-(4-benzo[d]isothiazol-3-yl-piperazin-1-yl)-ethyl]-2-methyl-phenylamine, {2-[2-(4-benzo[d]isothiazol-3-yl-piperazin-1-yl)-ethyl]-phenyl}-methyl-amine, or {2-[2-(4-benzo[d]isothiazol-3-yl-piperazin-1-yl)-ethyl]-phenyl}-isopropylamine with appropriate sulfonyl chloride starting materials on a 0.20 mmol scale in pyridine at 50–85° C., following the steps as outlined in Example 355. The crude products were purified by HPLC (30×100 mm ODS-A C(18) 5u column).

Example 449

N-{4-[2-(4-BENZO[D]ISOTHIAZOL-3-YL-PIPERAZIN-1-YL)-ETHYL]-2-METHYL-PHENYL}-4-METHOXY-BENZENESULFONAMIDE

Isolated in 100% purity @ 254 nm; LCMS (APCI): 523 $[M+H]^+$

Example 450

N-{4-[2-(4-BENZO[D]ISOTHIAZOL-3-YL-PIPERAZIN-1-YL)-ETHYL]-2-METHYL-PHENYL}-4-METHYL-BENZENESULFONAMIDE

Isolated in 100% purity @ 254 nm; LCMS (APCI): 507 $[M+H]^+$

Example 451

N-{4-[2-(4-BENZO[D]ISOTHIAZOL-3-YL-PIPERAZIN-1-YL)-ETHYL]-2-METHYL-PHENYL}-2,5-DIMETHOXY-BENZENESULFONAMIDE

Isolated in 100% purity @ 254 nm; LCMS (APCI): 553 $[M+H]^+$

Example 452

THIOPHENE-2-SULFONIC ACID {4-[2-(4-BENZO[D]ISOTHIAZOL-3-YL-PIPERAZIN-1-YL)-ETHYL]-2-METHYL-PHENYL}-AMIDE

Isolated in 100% purity @ 254 nm; LCMS (APCI): 499 $[M+H]^+$

Example 453

N-{4-[2-(4-BENZO[D]ISOTHIAZOL-3-YL-PIPERAZIN-1-YL)-ETHYL]-2-METHYL-PHENYL}-METHANESULFONAMIDE

Isolated in 100% purity @ 254 nm; LCMS (APCI): 431 $[M+H]^+$

Example 454

N-{4-[2-(4-BENZO[D]ISOTHIAZOL-3-YL-PIPERAZIN-1-YL)-ETHYL]-2-METHYL-PHENYL}-3,4-DIMETHOXY-BENZENESULFONAMIDE

Isolated in 100% purity @ 254 nm; LCMS (APCI): 553 $[M+H]^+$

Example 455

N-{4-[2-(4-BENZO[D]ISOTHIAZOL-3-YL-PIPERAZIN-1-YL)-ETHYL]-2-METHYL-PHENYL}-BENZENESULFONAMIDE

Isolated in 100% purity @ 254 nm; LCMS (APCI): 493 $[M+H]^+$

Example 456

N-{4-[2-(4-BENZO[D]ISOTHIAZOL-3-YL-PIPERAZIN-1-YL)-ETHYL]-2-METHYL-PHENYL}-C-(4-CHLORO-PHENYL)-METHANESULFONAMIDE

Isolated in 92% purity @ 254 nm; LCMS (APCI): 542 $[M+H]^+$

Example 457

QUINOLINE-8-SULFONIC ACID {4-[2-(4-BENZO[D]ISOTHIAZOL-3-YL-PIPERAZIN-1-YL)-ETHYL]-2-METHYL-PHENYL}-AMIDE

Isolated in 100% purity @ 254 nm; LCMS (APCI): 544 $[M+H]^+$

Example 458

ETHANESULFONIC ACID {4-[2-(4-BENZO[D]ISOTHIAZOL-3-YL-PIPERAZIN-1-YL)-ETHYL]-2-METHYL-PHENYL}-AMIDE

Isolated in 100% purity © 254 nm; LCMS (APCI): 445 $[M+H]^+$

Example 459

1,3,5-TRIMETHYL-1H-PYRAZOLE-4-SULFONIC ACID {4-[2-(4-BENZO[D]ISOTHIAZOL-3-YL-PIPERAZIN-1-YL)-ETHYL]-2-METHYL-PHENYL}-AMIDE

Isolated in 100% purity @ 254 nm; LCMS (APCI): 525 $[M+H]^+$

Example 460

1,2-DIMETHYL-1H-IMIDAZOLE-4-SULFONIC ACID {4-[2-(4-BENZO[D]ISOTHIAZOL-3-YL-PIPERAZIN-1-YL)-ETHYL]-2-METHYL-PHENYL}-AMIDE

Isolated in 100% purity @ 254 nm; LCMS (APCI): 511 $[M+H]^+$

Example 461

NAPHTHALENE-2-SULFONIC ACID {4-[2-(4-BENZO[D]ISOTHIAZOL-3-YL-PIPERAZIN-1-YL)-ETHYL]-2-METHYL-PHENYL}-AMIDE

Isolated in 100% purity @ 254 nm; LCMS (APCI): 543 $[M+H]^+$

Exampl 462

N-{4-[2-(4-BENZO[D]ISOTHIAZOL-3-YL-PIPERAZIN-1-YL)-ETHYL]-2-METHYL-PHENYL}-2-FLUORO-BENZENESULFONAMIDE

Isolated in 100% purity @ 254 nm; LCMS (APCI): 511 $[M+H]^+$

Example 463

N-{4-[2-(4-BENZO[D]ISOTHIAZOL-3-YL-PIPERAZIN-1-YL)-ETHYL]-2-METHYL-PHENYL}-3-METHOXY-BENZENESULFONAMIDE

Isolated in 100% purity @ 254 nm; LCMS (APCI): 523 $[M+H]^+$

Example 464

N-{4-[2-(4-BENZO[D]ISOTHIAZOL-3-YL-PIPERAZIN-1-YL)-ETHYL]-2-METHYL-PHENYL}-3-METHYL-BENZENESULFONAMIDE

Isolated in 100% purity @ 254 nm; LCMS (APCI): 507 $[M+H]^+$

Example 465

5-CHLORO-THIOPHENE-2-SULFONIC ACID {4-[2-(4-BENZO[D]ISOTHIAZOL-3-YL-PIPERAZIN-1-YL)-ETHYL]-2-M ETHYL-PHENYL}-AMIDE

Isolated in 100% purity @ 254 nm; LCMS (APCI): 534 $[M+H]^+$

Example 466

N-{4-[2-(4-BENZO[D]ISOTHIAZOL-3-YL-PIPERAZIN-1-YL)-ETHYL]-2-METHYL-PHENYL}-2-CHLORO-BENZENESULFONAMIDE

Isolated in 100% purity @ 254 nm; LCMS (APCI): 528 $[M+H]^+$

Example 467

N-{2-[2-(4-BENZO[D]ISOTHIAZOL-3-YL-PIPERAZIN-1-YL)-ETHYL]-PHENYL}-4-CHLORO-N-ISOPROPYL-BENZENESULFONAMIDE

Isolated in 100% purity @ 254 nm; LCMS (APCI): 555 [M+H]+

Example 468

NAPHTHALEN E-2-SULFONIC ACID {2-[2-(4-BENZO[D]ISOTHIAZOL-3-YL-PIPERAZIN-1-YL)-ETHYL]-PHENYL}-ISOPROPYL-AMIDE

Isolated in 100% purity @ 254 nm; LCMS (APCI): 570 $[M+H]^+$

Example 469

N-{2-[2-(4-BENZO[D]ISOTHIAZOL-3-YL-PIPERAZIN-1-YL)-ETHYL]-PHENYL}-2-FLUORO-N-ISOPROPYL-BENZENESULFONAMIDE

Isolated in 100% purity @ 254 nm; LCMS (APCI): 539 $[M+H]^+$

Example 470

N-{2-[2-(4-BENZO[D]ISOTHIAZOL-3-YL-PIPERAZIN-1-YL)-ETHYL]-PHENYL}-N-ISOPROPYL-3-METHOXY-BENZENESULFONAMIDE

Isolated in 100% purity @ 254 nm; LCMS (APCI): 551 $[M+H]^+$

Example 471

N-{2-[2-(4-BENZO[D]ISOTHIAZOL-3-YL-PIPERAZIN-1-YL)-ETHYL]-PHENYL}-N-ISOPROPYL-3-METHYL-BENZENESULFONAMIDE

Isolated in 100% purity @ 254 nm; LCMS (APCI): 535 $[M+H]^+$

Example 472

N-{2-[2-(4-BENZO[D]ISOTHIAZOL-3-YL-PIPERAZIN-1-YL)-ETHYL]-PHENYL}-2-CHLORO-N-ISOPROPYL-BENZENESULFONAMIDE

Isolated in 100% purity @ 254 nm; LCMS (APCI): 556 $[M+H]^+$

Example 473

N-{2-[2-(4-BENZO[D]ISOTHIAZOL-3-YL-PIPERAZIN-1-YL)-ETHYL]-PHENYL}-N-ISOPROPYL-4-METHOXY-BENZENESULFONAMIDE

Isolated in 100% purity @ 254 nm; LCMS (APCI): 551 $[M+H]^+$

Example 474

N-{2-[2-(4-BENZO[D]ISOTHIAZOL-3-YL-PIPERAZIN-1-YL)-ETHYL]-PHENYL}-N-ISOPROPYL-4-METHYL-BENZENESULFONAMIDE

Isolated in 100% purity @ 254 nm; LCMS (APCI): 535 $[M+H]^+$

Example 475

N-{2-[2-(4-BENZO[D]ISOTHIAZOL-3-YL-PIPERAZIN-1-YL)-ETHYL]-PHENYL}-N-ISOPROPYL-2,5-DIMETHOXY-BENZENESULFONAMIDE

Isolated in 100% purity @ 254 nm; LCMS (APCI): 581 $[M+H]^+$

Example 476

THIOPHENE-2-SULFONIC ACID {2-[2-(4-BENZO[D]ISOTHIAZOL-3-YL-PIPERAZIN-1-YL)-ETHYL]-PHENYL}-ISOPROPYL-AMIDE

Isolated in 100% purity @ 254 nm; LCMS (APCI): 527 $[M+H]^+$

Example 477

N-{2-[2-(4-BENZO[D]ISOTHIAZOL-3-YL-PIPERAZIN-1-YL)-ETHYL]-PHENYL}-4-FLUORO-N-ISOPROPYL-BENZENESULFONAMIDE

Isolated in 100% purity @ 254 nm; LCMS (APCI): 539 $[M+H]^+$

Example 478

N-{2-[2-(4-BENZO[D]ISOTHIAZOL-3-YL-PIPERAZIN-1-YL)-ETHYL]-PHENYL}N-ISOPROPYL-3,4-DIMETHOXY-BENZENESULFONAMIDE

Isolated in 100% purity @ 254 nm; LCMS (APCI): 581 $[M+H]^+$

Example 479

N-{2-[2-(4-BENZO[D]ISOTHIAZOL-3-YL-PIPERAZIN-1-YL)-ETHYL]-PHENYL}N-ISOPROPYL-BENZENESULFONAMIDE

Isolated in 100% purity @ 254 nm; LCMS (APCI): 521 $[M+H]^+$

Example 480

QUINOLINE-8-SULFONIC ACID {2-[2-(4-BENZO[D]ISOTHIAZOL-3-YL-PIPERAZIN-1-YL)-ETHYL]-PHENYL}-ISOPROPYL-AMIDE

Isolated in 100% purity @ 254 nm; LCMS (APCI): 572 [M+H]+

Example 481

1,3,5-TRIMETHYL-1H-PYRAZOLE-4-SULFONIC ACID {2-[2-(4-BENZO[D]ISOTHIAZOL-3-YL-PIPERAZIN-1-YL)-ETHYL]-PHENYL}-ISOPROPYL-AMIDE

Isolated in 100% purity @ 254 nm; LCMS (APCI): 553 $[M+H]^+$

Example 482

12-DIMETHYL-1H-IMIDAZOLE-4-SULFONIC ACID {2-[2-(4-BENZO[D]ISOTHIAZOL-3-YL-PIPERAZIN-1-YL)-ETHYL]-PHENYL}-ISOPROPYL-AMIDE

Isolated in 100% purity @ 254 nm; LCMS (APCI): 539 $[M+H]^+$

Example 483

N-{2-[2-(4-BENZO[D]ISOTHIAZOL-3-YL-PIPERAZIN-1-YL)-ETHYL]-PHENYL}-4-CHLORO-N-METHYL-BENZENESULFONAMIDE

Isolated in 100% purity @ 254 nm; LCMS (APCI): 528 $[M+H]^+$

Example 484

NAPHTHALENE-2-SULFONIC ACID {2-[2-(4-BENZO[D]ISOTHIAZOL-3-YL-PIPERAZIN-1-YL)-ETHYL]-PHENYL}-METHYL-AMIDE

Isolated in 100% purity @ 254 nm; LCMS (APCI): 543 $[M+H]^+$

Example 485

N-{2-[2-(4-BENZO[D]ISOTHIAZOL-3-YL-PIPERAZIN-1-YL)-ETHYL]-PHENYL}-2-FLUORO-N-METHYL-BENZENESULFONAMIDE

Isolated in 100% purity @ 254 nm; LCMS (APCI): 511 [M+H]$^+$

Example 486

N-{2-[2-(4-BENZO[D]ISOTHIAZOL-3-YL-PIPERAZIN-1-YL)-ETHYL]-PHENYL}-3-METHOXY-N-METHYL-BENZENESULFONAMIDE

Isolated in 100% purity @ 254 nm; LCMS (APCI): 523 [M+H]$^+$

Example 487

N-{2-[2-(4-BENZO[D]ISOTHIAZOL-3-YL-PIPERAZIN-1-YL)-ETHYL]-PHENYL}-3,N-DIMETHYL-BENZENESULFONAMIDE Isolated in 100% purity @ 254 nm; LCMS (APCI): 507 [M+H]$^+$ Example 488

5-CHLORO-THIOPHENE-2-SULFONIC ACID {2-[2-(4-BENZO[D]ISOTHIAZOL-3-YL-PIPERAZIN-1-YL)-ETHYL]-PHENYL}-METHYL-AMIDE

Isolated in 100% purity © 254 nm; LCMS (APCI): 534 [M+H]$^+$

Example 489

N-{2-[2-(4-BENZO[D]ISOTHIAZOL-3-YL-PIPERAZIN-1-YL)-ETHYL]-PHENYL}-2-CHLORO-N-METHYL-BENZENESULFONAMIDE

Isolated in 100% purity @ 254 nm; LCMS (APCI): 528 [M+H]$^+$

Example 490

N-{2-[2-(4-BENZO[D]ISOTHIAZOL-3-YL-PIPERAZIN-1-YL)-ETHYL]-PHENYL}-4-METHOXY-N-METHYL-BENZENESULFONAMIDE

Isolated in 100% purity @ 254 nm; LCMS (APCI): 523 [M+H]$^+$

Example 491

N-{2-[2-(4-BENZO[D]ISOTHIAZOL-3-YL-PIPERAZIN-1-YL)-ETHYL]-PHENYL}-4,N-DIMETHYL-BENZENESULFONAMIDE

Isolated in 100% purity @ 254 nm; LCMS (APCI): 507 [M+H]$^+$

Example 492

N-{2-[2-(4-BENZO[D]ISOTHIAZOL-3-YL-PIPERAZIN-1-YL)-ETHYL]-PHENYL}-2,5-DIMETHOXY-N-METHYL-BENZENESULFONAMIDE

Isolated in 100% purity @ 254 nm; LCMS (APCI): 553 [M+H]$^+$

Example 493

THIOPHENE-2-SULFONIC ACID {2-[2-(4-BENZO[D]ISOTHIAZOL-3-YL-PIPERAZIN-1-YL)-ETHYL]-PHENYL}-METHYL-AMIDE

Isolated in 100% purity @ 254 nm; LCMS (APCI): 499 [M+H]$^+$

Example 494

N-{2-[2-(4-BENZO[D]ISOTHIAZOL-3-YL-PIPERAZIN-1-YL)-ETHYL]-PHENYL}-N-METHYL-METHANESULFONAMIDE

Isolated in 100% purity @ 254 nm; LCMS (APCI): 430 [M+H]$^+$

Example 495

N-{2-[2-(4-BENZO[D]ISOTHIAZOL-3-YL-PIPERAZIN-1-YL)-ETHYL]-PHENYL}-3,4-DIMETHOXY-N-METHYL-BENZENESULFONAMIDE

Isolated in 100% purity @ 254 nm; LCMS (APCI): 553 [M+H]$^+$

Example 496

N-{2-[2-(4-BENZO[D]ISOTHIAZOL-3-YL-PIPERAZIN-1-YL)-ETHYL]-PHENYL}-N-METHYL-BENZENESULFONAMIDE

Isolated in 100% purity @ 254 nm; LCMS (APCI): 493 [M+H]$^+$

Example 497

QUINOLINE-8-SULFONIC ACID {2-[2-(4-BENZO[D]ISOTHIAZOL-3-YL-PIPERAZIN-1-YL)-ETHYL]-PHENYL}-METHYL-AMIDE

Isolated in 100% purity @ 254 nm; LCMS (APCI): 543 [M+H]$^+$

Example 498

1,3,5-TRIMETHYL-1H-PYRAZOLE-4-SULFONIC ACID {2-[2-(4-BENZO[D]ISOTHIAZOL-3-YL-PIPERAZIN-1-YL)-ETHYL]-PHENYL}-METHYL-AMIDE

Isolated in 100% purity @ 254 nm; LCMS (APCI): 525 [M+H]$^+$

Example 499

1,2-DIMETHYL-1H-IMIDAZOLE-4-SULFONIC ACID {2-[2-(4-BENZO[D]ISOTHIAZOL-3-YL-PIPERAZIN-1-YL)-ETHYL]-PHENYL}-METHYL-AMIDE

Isolated in 100% purity @ 254 nm; LCMS (APCI): 511 $[M+H]^+$

2-FLUORO-4-IODO-PHENYLAMINE

2-Fluoroaniline (54 g, 486 mmol) was added to a vigorously stirred solution of sodium bicarbonate (41 g, 486 mmol) in water (250 mL). The suspension was warmed to 60° C. on an oil bath and iodine (123 g, 486 mmol) was added portion-wise. After complete addition, the dark mixture was stirred for an additional 3 h at 60° C. After cooling to rt, methylene chloride (300 mL) was added followed by saturated hydrogensulfite solution (300 mL). The biphasic system was vigorously stirred for an additional 10 min. The mixture was poured into a 2 L separatory funnel and the organic layer was released. The aqueous was further extracted with methylene chloride (3×200 mL) and the combined organics were washed with brine (200 mL) and dried over anhydrous sodium sulfate. After filtration, the solvent was removed to give a black crystalline solid. Hexane (300 mL) was added and the mixture was heated to reflux. The hexane was decanted from a black, insoluble syrup. The product crystallized from the hexane on cooling as fine yellow needles. 65 g (274 mmol) was isolated as a fine yellow solid. Yield: 56%; mp 53° C.; $^1H$ NMR (400 MHz, $CDCl_3$) δ 8.1 (t, J=8 Hz, 1H), 7.4 (d, J=6 Hz, 1H), 7.2 (d, J=6 Hz, 1H).

Preparation 34

N-(2-FLUORO-4-IODO-PHENYL)-ACETAMIDE

To a stirred solution of 2-fluoro-4-iodo-phenylamine (61 g, 257 mmol) in anhydrous pyridine (25 mL) was added drop-wise acetic anhydride (32.8 mL, 321 mmol) at such a rate to maintain the internal temperature between 10° C. and 20° C. At the end of the addition, the reaction was stirred for an additional 0.5 h at rt followed by heating on an oil bath (external temperature 50–60° C.). The reaction was monitored by thin layer chromatography. Once complete (ca. 1.5 h), the mixture was cooled and the reaction mixture solidified. The solid was slurried with cold ethanol (50 mL) and filtered. The solid was washed with cold ethanol (mL) and dried to a fine white crystalline material. The filtrate was concentrated and taken up in ethanol (20 mL) and cooled overnight. Further product was obtained. 63 g (226 mmol) was isolated as a fine white, crystalline solid. Yield: 88%; mp 153° C.; $^1H$ NMR (400 MHz, $CDCl_3$) δ 8.15 (t, J=8 Hz, 1H), 7.33 (br s, 1H), 7.49 (m, 2H), 2.24 (s, 3H, Me).

Preparation 35

N-(4-CYANO-2-FLUORO-PHENYL)-ACETAMIDE

N-(2-Fluoro-4-iodo-phenyl)-acetamide (63 g, 226 mmol) was dissolved in HPMA (100 mL). Copper(1) cyanide (20.6 g, 230 mmol) was added and the mixture heated to an external temperature of 153° C. for 5 h. The hot reaction mixture was poured into water (1 L) with stirring. A large amount of solid formed. The solid was filtered and washed with water (200 mL). The solid was extracted by heating in a flask with methylene chloride (500 mL) for 15 min. The solid was filtered off, washed with methylene chloride (3×100 mL). The combined organic extracts were washed with brine (200 mL), dried over anhydrous sodium sulfate, filtered and concentrated to give a brown-orange solid. Ethanol (100 mL) was added and the mixture heated to reflux. The solid did not all dissolve. The cooled mixture was filtered to give a light brown solid. The filtrate was concentrated to ½ volume and cooled overnight to give a further crop of solid. The combined solids were washed with cold ethanol (30 mL) and dried under vacuum to give 30 g (168 mmol). Yield: 75%; mp 173° C.; $^1H$ NMR (400 MHz, DMSO-$d_6$) δ 10.3 (br s, 1H, N$\underline{H}$), 8.3 (t, J=8.2 Hz, 1H), 7.9 (d, J=10.7 Hz, 1H), 7.67 (d, J=10.7 Hz, 1H), 2.16 (s, 3H, Me).

Preparation 36

N-(2-FLUORO-4-FORMYL-PHENYL)-ACETAMIDE

Stannous chloride (98%, 17.3 g, 91.5 mmol) was placed in a dry 3-neck 500 mL round bottom flask under argon. Anhydrous diethyl ether (100 mL) was added via cannula. The suspension was stirred as dry HCl gas was bubbled in until the solid dissolved. Anhydrous methylene chloride (100 mL) was added via cannula to homogenize the two layers and the solution was stirred for an additional 0.5 h while a continuous stream of dry HCl gas was bubbled through the solution. N-(4-Cyano-2-fluoro-phenyl)-acetamide (10.5 g, 58.7 mmol) was added and the suspension stirred at rt for an additional 3 h under a continuous stream of dry HCl gas. During this time a sticky, yellow solid formed which eventually crystallized. The reaction mixture was left standing overnight after the introduction of HCL was stopped. The residue was partioned between methylene chloride (100 mL) and water (100 mL) and the phases were separated. The aqueous phase was extracted with methylene chloride (100 mL) and the combined organic extracts were washed with brine (100 mL) and dried over anhydrous potassium carbonate (essential for purity of the product). Concentration of the solvent provided 10.5 g (57.7 mmol) of a crystalline residue. Yield: 98%; mp 133° C.; $^1H$ NMR (400 MHz, $CDCl_3$) δ 10.1 (s, 1H, N$\underline{H}$), 9.9 (s, 1H, C$\underline{H}$O), 8.39 (t, J=8.0 Hz, 1H), 7.76–7.72 (m, 2H), 2.18 (s, 3H, Me).

Preparation 37

N-(4-ACETYL-2-FLUORO-PHENYL)-ACETAMIDE

N-(2-Fluoro-4-formyl-phenyl)-acetamide (10.5 g, 57.7 mmol) was dissolved in anhydrous THF (200 mL) in a dry 3-neck 500 mL round bottom flask under argon. Stirring was achieved with an overhead stirrer. A solution of 3.0 M methylmagnesium bromide (103 mL, 309 mmol) was slowly added dropwise over a 10 min. period under argon. The mixture was heated overnight on a 60° C. oil bath. The reaction mixture was cooled and then poured onto saturated ammonium chloride (300 mL) in ice (200 g). The organic layer was decanted away. The aqueous layer was saturated with solid ammonium chloride and then extracted with methylene chloride (2×100 mL). The combined organic layers were dried over anhydrous sodium sulfate, filtered and concentrated to give an oil (9.4 g) which was directly used without further purification. The oil was dissolved in acetone (100 mL) and placed in a 21° C. water bath. A mixture of chromium (VI) oxide (5.1 g, 538 mmol), concentrated sulfuric acid (2.5 mL) and water (7.5 mL) was slowly added followed by water (75 mL). The dark brown solution was stirred for an additional 15 min. Saturated hydrogen sulfite solution (10 mL) was added and the green solution was extracted with methylene chloride (4×100 mL). The combined organic extracts were washed with brine (100 mL) and dried over anhydrous sodium sulfate. After filtration the solution was concentrated to give a yellow, brown residue. The residue was dissolved in boiling water (150 mL), decanted hot from a black insoluble oil and cooled. Crystallization provided 3.55 g (18.2 mmol) of the product as pale yellow needles. Yield: 32%; mp 149° C.; TLC (silica): $R_f$=0.5 (ethyl acetate).

Preparation 38

N-[4-(2-BROMO-ACETYL)-2-FLUORO-PHENYL]-ACETAMIDE

N-(4-Acetyl-2-fluoro-phenyl)-acetamide (3.55 g, 18.2 mmol) was dissolved in boiling chloroform (100 mL). Under reflux conditions, a solution of bromine (0.86 mL, 17.5 mmol) in chloroform (20 mL) was added. The reaction mixture was refluxed for an additional 20 min. then cooled, concentrated to give an orange residue. The residue was taken up in ethanol (50 mL) and then diethyl ether (20 mL) was added and the resulting solution cooled to 0° C. A yellow solid precipitated over 48 h and was collected by filtration, washed with cold ethanol (10 mL) and dried to give 2.40 g (8.77 mmol) of the desired product as a yellow powder. Yield: 48.2%; mp 184° C.; $^1$H NMR (400 MHz, DMSO-$d_6$) δ 10.15 (s, 1H, N<u>H</u>, 8.29 (t, J=8.0 Hz, 1H), 7.88–7.83 (m, 2H), 4.90 (s, 2H, $CH_2$), 2.17 (s, 3H, Me).

Preparation 39

N-[4-(2-BROMO-ETHYL)-2-FLUORO-PHENYL]-ACETAMIDE

Triethylsilane (1.60 mL, 10.017 mmol) was added via syringe to a stirred solution of N-[4-{2-bromo-acetyl)-2-fluoro-phenyl]-acetamide (1.1435 g, 4.172 mmol) in trifluoroacetic acid (14.0 mL) under nitrogen. The reaction was heated on an oil bath to 60° C. After 2.5 h, the reaction mixture was poured into ice water and allowed to warm to rt. The crude product was extracted with methylene chloride (2×75 mL). The combined organic extracts were washed with brine (50 mL), dried over anhydrous sodium sulfate, filtered and concentrated. The residue was crystallized from methanol and water to provide 0.6109 g (2.349 mmol) of the product as a white solid. Yield: 56%; MS (APCI): 260 $[M+H]^+$, 262 $[M+H+2]^+$; $^1$H NMR (400 MHz, $CDCl_3$) δ 8.22 (dd, J=8.3, 8.5 Hz, 1H), 7.30 (br s, 1H), 6.93–6.97 (m, 2H), 3.51 (t, J=7.3 Hz, 2H), 3.10 (t, J=7.3 Hz, 2H), 2.20 (s, 3H).

Example 500

N-{4-[2-(4-BENZO[D]ISOTHIAZOL-3-YL-PIPERAZIN-1-YL)-ETHYL]-2-FLUORO-PHENYL}-ACETAMIDE

N-[4-(2-Bromo-ethyl)-2-fluoro-phenyl]-acetamide (0.2609 g, 1.00 mmol), 3-piperazin-1-yl-benzo[d]isothiazole hydrochloride (0.3887 g, 1.52 mmol), potassium carbonate (0.2109 g, 1.53 mmol), potassium iodide (0.1662 g, 1.00 mmol) and acetonitrile (5.0 mL) were added to a Smith microwave reaction tube containing a magnetic stir bar and then crimped shut. The reaction was run on a Smith Personal Chemistry microwave at 140° C. for 0.5 h. After removing the crimped septum, the contents were transferred to a separatory funnel with water (10 mL) and extracted with methylene chloride (2×40 mL). The combined organic extracts were dried over anhydrous sodium sulfate, filtered and concentrated to give an oily residue. Purification by MPLC on a 40M silica gel cartridge using a linear gradient over 1 h of 0–3% methanol in methylene chloride provided 0.1230 g (0.309 mmol) of the product as an off-white solid after drying in vacuo. Several fractions containing product and a by-product (0.1487 g total) were discarded. Yield: 31%; MS (APCI): 399.2 $[M+H]^+$; Anal. Calcd. For $C_{21}H_{23}FN_4OS.0.25\ H_2O$: C, 62.59; H, 5.88; N, 13.90. Found: C, 62.72; H, 5.53; N, 13.53.

Preparation 40

N-(5-CHLORO-2-METHYL-PHENYL)-ACETAMIDE

5-Chloro-2-methyl-phenylamine (50 g, 353.11 mmol) was dissolved in dry THF (500 mL) followed by addition of triethylamine (61.53 mL, 441.39 mmol) and the whole heated to 60° C. To the stirring solution at 60° C. was added dropwise a solution of acetic anhydride (50 ml, 529.66 mmol) in dry THF (100 mL) and the reaction was stirred at 60° C. overnight. Upon cooling, the reaction was diluted with $H_2O$ (500 mL), ethyl acetate (250 mL) and the layers separated. The organics were washed with $H_2O$ (250 mL), 1N HCl (250 mL), sat $Na_2CO_3$ (250 mL), brine (250 mL), dried ($MgSO_4$) and concentrated to a solid (59.67 g, 324.97 mmol).

Yield 92%; $^1$H NMR (400 MHz, $CDCl_3$) δ 7.85 (s, 1H), 7.06–6.98 (m, 3H), 2.17 (s, 3H).

Preparation 41

N-[5-CHLORO-4-(2-CHLORO-ACETYL)-2-METHYL-PHENYL]-ACETAMIDE

To N-(5-Chloro-2-methyl-phenyl)-acetamide (30 g, 163.37 mmol) in carbondisulfide (1200 mL) was added chloroacetylchloride (19.50 mL, 245.05 mmol) followed by anhydrous aluminum chloride powder (65.35 g, 490.11 mmol) in one portion at rt. The reaction was heated to reflux for 3 h after which the reaction was cooled and the solvent decanted. The remaining residue was carefully hydrolyzed with cold $H_2O$ (500 mL) with vigorous stirring to give a white/gray solid suspension which was collected by filtration and dried in vacuo to give desire product (32.15 g, 123.6 mmol). Yield=76%; $^1$H NMR (400 MHz, $CDCl_3$) δ 8.28 (bs, 1H, NH), 7.47 (s, 1H), 7.24 (s, 1H), 4.73 (s, 2H), 2.25 (s, 3H).

Preparation 42

N-[5-CHLORO-4-(2-CHLORO-ETHYL)-2-METHYL-PHENYL]-ACETAMIDE

To a solution of N-[5-Chloro-4-(2-chloro-acetyl)-2-methyl-phenyl]-acetamide (10 g, 38.44 mmol) in trifluoroacetic acid (100 mL) at <20° C. was added portionwise, triethylsilane (15.35 mL, 96.1 mmol). The reaction was heated to 60° C. and stirred overnight. The reaction was cooled to rt and poured over ice/$H_2O$ and stirred for 30 min as a grey precipitate formed. The precipitate was collected by filtration and dried in vacuo overnight to give desired product (8.35 g, 33.92 mmol). Yield=88%; MS (APCI): 246 $[M+H]^+$. $^1H$ NMR (400 MHz, $CDCl_3$) δ 7.89 (s, 1H), 7.05 (s, 1H), 6.93 (bs, 1H, NH), 3.69 (t, J=7.26 Hz, 2H), 3.10 (t, J=7.26 Hz, 2H), 2.20 (d, J=4.48 Hz, 3H).

Preparation 43

N-[5-CHLORO-4-(2-CHLORO-ETHYL)-2-METHYL-PHENYL-N-METHYL-ACETAMIDE

To N-[5-Chloro-4-(2-chloro-ethyl)-2-methyl-phenyl]-acetamide (0.45 g, 2.126 mmol) in dry THF (25 mL) was added sodium hydride (60% dispersed in oil, 0.113 g, 2.834 mmol), with hydrogen evolution noted. After 10 min, iodomethane (0.176 mL, 2.834 mmol) was added dropwise at 0° C. The reaction was allowed to warm to rt and stir for 1.5 h. The reaction was diluted with methanol (5 mL), and concentrated to give a residue which was subjected to MPLC (50% ethyl acetate/Hexanes). Product collected as a clear and colorless oil (0.480 g, 2.125 mmol). Yield=100%. MS (APCI): 226 $[M+H]^+$; $^1H$ NMR (400 MHz, $CDCl_3$) δ 7.15–7.02 (m, 3H), 3.71 (t, J=7.29 Hz, 2H), 3.15 (s, 3H), 3.04 (t, J=7.29 Hz, 2H), 2.20 (s, 3H), 1.75 (s, 3H).

Preparation 44

3-PIPERAZIN-1-YL-1H-INDAZOLE

A neat mixture of 3-chloroindazole (15.72 g, 0.103 mol) and piperazine (46.00 g, 0.534 mol) was heated at 250° C. for 14 h in a stainless steel sealed vessel Upon cooling to room temperature, the viscous residue was partitioned between 1.0 N aqueous NaOH and methylene chloride. The organic layer was dried over magnesium sulfate, filtered, and the filtrate treated with 4.1 N HCl in dioxane which resulted in the precipitation of both products as a greenish-yellow gummy residue. The gum was collected and taken up in water where it was observed that the disubstituted piperazine precipitated out of solution. The precipitate was filtered off and the filtrate was concentrated in vacuo to give exclusively the monosubstituted piperazine, 3-piperazin-1-yl-1H-indazole, as a green foam. Yield, 19.03 g (77%). MS (APCI): 203 $[M+H]^+$, 201 $[M-H]^-$.

Example 501

N-{4-[2-(4-BENZO[D]ISOTHIAZOL-3-YL-PIPERAZIN-1-YL)-ETHYL]-5-CHLORO-2-METHYL-PHENYL}-N-METHYL-ACETAMIDE

N-[4-(2-chloro-ethyl)-2-methyl-phenyl]-N-methyl-acetamide (0.300 g, 1.153 mmol), 3-piperazin-1-yl-benzo[d]isothiazole hydrochloride (0.442 g, 1.729 mmol), potassium carbonate (0.237 g, 1.729 mmol), and potassium iodide (0.173 g, 1.153 mmol) in acetonitrile (3.5 mL) was subjected to 150° C. for 30 min. under microwave assistance using a Smith Personal Chemistry microwave. The reaction was diluted with $H_2O$ (50 mL) and $CH_2Cl_2$ (100 mL). The layers were separated and the organics washed with 1 N HCl (2×25 mL). The aqueous layer was made basic and extracted with $CH_2Cl_2$ (3×50 mL). The organics were dried ($MgSO_4$), and concentrated to a solid residue. The residue was subjected to chromatography (MeOH:$CH_2Cl_2$ 1:19) and collected as an amorphous residue and taken up in 1,4-dioxane and subjected to HCl gas for 10 min. The resulting solid was collected by filtration and dried at 50° C. under high vacuum overnight (0.770 g). 100% purity at 254 nm; LCMS (APCI): 409.2 $[M+H]^+$.

Preparation 45

N-[4-(2-CHLORO-ACETYL)-2-METHYL-PHENYL]-ACETAMIDE

N-[4-(2-Chloro-acetyl)-2-methyl-phenyl]-acetamide was prepared according to the general method as outlined in Preparation 41 starting with o-tolylacetamide (35 g, 234.6 mmol) and chloroacetyl chloride (23.34 mL, 293.25 mmol). After chromatographic separation of isomers ($CH_2Cl_2$/EtoAc/Hex, 85:10:5), the product was obtained as a solid (2.40 g, 10.63 mmol). Yield=4.5%. 100% purity at 254 nm; LCMS (APCI): 226.3 $[M+H]^+$; $^1H$ NMR (400 MHz, $CDCl_3$) δ 8.23 (bd, J=8.45 Hz, 1H), 7.81 (d, J=2.22 Hz, 1H), 7.78 (dd, J=2.22 Hz, J=8.45 Hz, 1H), 7.10 (bs, 1H), 4.67 (s, 2H), 2.33 (s, 3H), 2.25 (s, 3H).

Preparation 46

N-[4-(2-CHLORO-ETHYL)-2-METHYL-PHENYL]-ACETAMIDE

N-[4-(2-Chloro-ethyl)-2-methyl-phenyl]-acetamide was prepared according to the general method as outlined in Preparation 42 starting with N-[4-(2-chloro-acetyl)-2-methyl-phenyl]-acetamide (1.00 g, 4.43 mmol) to give a white solid with trace triethylsilanol contaminate (7% by NMR). Product was taken on as is for further use. 100% purity at 254 nm; LCMS (APCI) 212.3 $[M+H]^+$; $^1H$ NMR (400 MHz, $CDCl_3$) δ 7.62 (d, J=7.02 Hz, 1H), 7.06 (bs, 1H), 7.04–6.98 (bm, 2H), 3.65 (t, J=7.02 Hz, 2H), 2.98 (t, J=7.02 Hz, 2H), 2.21 (s, 3H), 2.16 (s, 3H), 0.95 (t, J=7.67 Hz, 0.48H, $Et_3SiOH$), 0.57 (q, J=7.67 Hz, 0.31H, $Et_3SiOH$).

Example 502

N-{4-[2-(4-1,2-BENZISOTHIAZOL-3-YL-PIPERAZIN-1-YL)-ETHYL]-2-METHYL-PHENYL}-ACETAMIDE

Starting from N-[4-(2-Chloro-ethyl)-2-methyl-phenyl]-acetamide (11.96 g, 56.5 mmol) and 3-piperazin-1-yl-benzo[d]isothiazole hydrochloride (16.58 g, 73.5 mmol), (N-{4-[2-(4-1,2-Benzisothiazol-3-yl-piperazin-1-yl)-ethyl]-2-methyl-phenyl}-acetamide was prepared according to the general method as outlined in Example 501. The titled product was obtained as an off-white solid, (19.04 g, 48.3 mmol). Yield=85%. 98.8% purity by HPLC; mp 176.5–178.° C.

Preparation 47

N-[4-(2-CHLORO-ETHYL)-2-METHYL-PHENYL]-N-METHYL-ACETAMIDE

N-[4-(2-Chloro-ethyl)-2-methyl-phenyl]-N-methyl-acetamide was prepared according to the general method as outlined in Preparation 43 starting from N-[4-(2-chloro-ethyl)-2-methyl-phenyl]-acetamide (0.450 g, 2.126 mmol) and iodomethane (0.176 ml, 2.834 mmol). After chromatographic purification, the product was isolated as a viscous oil (0.480 g, 2.125 mmol). Yield=100%. MS (APCI): 226 $[M+H]^+$; $^1H$ NMR (400 MHz, $CDCl_3$) δ 7.13(bs, 1H), 7.08 (bd, J=7.57 Hz, 1H), 7.05 (d, J=7.57 Hz, 1H), 3.71 (t, J=7.06 Hz, 1H), 3.15 (s, 3H), 3.04 (t, J=7.06 Hz, 2H), 2.20 (s, 3H), 1.75 (s, 3H).

Example 503

N-{4-[2-(4-BENZO[D]ISOTHIAZOL-3-YL-PIPERAZIN-1-YL)-ETHYL]-2-METHYL-PHENYL}-N-METHYL-ACETAMIDE

Starting with N-[4-(2-chloro-ethyl)-2-methyl-phenyl]-N-methyl-acetamide (0.226 g, 1.00 mmol) and 3-piperazin-1-yl-benzo[d]isothiazole hydrochloride (0.384 g, 1.50 mmol), and following the procedure outlined in Example 501, N-{4-[2-(4-benzo[d]isothiazol-3-yl-piperazin-1-yl)-ethyl]-2-methyl-phenyl}-N-methyl-acetamide was obtained as its hydrochloride salt (0.341 g, 0.41 mmol). Yield=71%;100% purity at 254 nm; LCMS (APCI): 409.2 $[M+H]^+$, $^1H$ NMR (400 MHz, DMSO-$d_6$) δ 8.12 (d, J=7.51 Hz, 1H), 8.08 (d, J=7.51 Hz, 1H), 7.57 (t, J=7.51 Hz, 1H), 7.44 (t, J=7.51 Hz, 1H), 7.26 (s, 1H), 7.24–7.19 (m, 2H), 4.07 (d, J=13.23 Hz, 2H), 3.65 (d, J=13.23 Hz, 2H), 3.53 (apparent t, J=12.21 Hz, 2H), 3.44–3.22 (m, 4H), 3.19–3.07 (m, 2H), 3.00 (s, 3H), 2.14 (s, 3H), 1.60 (s, 3H); Anal. Calcd for $C_{23}H_{29}N_4O_1S_1Cl_1$: C, 60.88; H, 6.49; N, 12.35. Found: C, 60.48; H, 6.59; N, 11.98.

Example 504

N-(4-{2-[4-(1H-INDAZOL-3-YL)-PIPERAZIN-1-YL]-ETHYL}-2-METHYL-PHENYL)-N-METHYL-ACETAMIDE HYDROCHLORIDE

Starting with N-[4-(2-chloro-ethyl)-2-methyl-phenyl]-N-methyl-acetamide (0.195 g, 0.863 mmol) and 3-piperazin-1-yl-1H-indazole hydrochloride (0.309 g, 1.24 mmol) and following the procedure as outlined in Example 501, N-(4-{2-[4-(1H-indazol-3-yl)-piperazin-1-yl]-ethyl}-2-methyl-phenyl)-N-methyl-acetamide was obtained as its hydrochloride salt (0.152 g, 0.388 mmol). Yield=45%. 100% purity @ 254 nm; LCMS (APCI): 392.3 $[M+H]^+$; $^1H$ NMR (400 MHz, DMSO-$d_6$) δ 12.19 (s, 1H), 10.57 (bs, 1H), 7.79 (d, J=8.91 Hz, 1H), 7.37 (d, J=8.91 Hz, 1H), 7.32–7.24 (m, 2H), 7.24–7.13 (m, 2H), 6.99 (t, J=6.93 Hz, 1H), 3.97 (bd, J=9.77 Hz, 2H), 3.64 (bm, 2H), 3.48 (bs, DMSO-$H_2O$), 3.44–3.24 (m, 6H), 3.10–3.02 (m, 2H), 3.00 (s, 3H), 2.47 (DMSO), 2.15 (s, 3H), 1.60 (s, 3H).

Preparation 48

N-[4-(2-CHLORO-ETHYL)-2-METHYL-PHENYL]-N-ETHYL-ACETAMIDE

N-[4-(2-Chloro-ethyl)-2-methyl-phenyl]-N-ethyl-acetamide was prepared according to the general method as outlined in Preparation 43 starting from N-[4-(2-chloro-ethyl)-2-methyl-phenyl]-acetamide (0.40 g, 1.89 mmol) and ethyliodide (0.189 mL, 2.36 mmol). After chromatographic purification, the product was isolated as a viscous oil (0.399 g, 1.66 mmol).

Yield=88%. MS (APCI): 240 $[M+H]^+$; $^1H$ NMR (400 MHz, $CDCl_3$) δ 7.14 (bs, 1H), 7.08 (bd, J=7.74 Hz, 1H), 7.01 (d, J=7.74 Hz, 1H), 4.06 (sextet, J=6.59 Hz, 1H), 3.71 (t, J=7.18 Hz, 2H), 3.22 (sextet, J=6.59 Hz, 1H), 3.04 (t, J=7.18 Hz, 2H), 2.20 (s, 3H), 1.70 (s, 3H), 1.1 (t, J=7.14 Hz, 3H).

Example 505

N-{4-[2-(4-BENZO[D]ISOTHIAZOL-3-YL-PIPERAZIN-1-YL)-ETHYL]-2-METHYL-PHENYL}-N-ETHYL-ACETAMIDE

Starting with N-[4-(2-chloro-ethyl)-2-methyl-phenyl]-N-ethyl-acetamide (0.169 g, 0.706 mmol) and 3-piperazin-1-yl-benzo[d]isothiazole hydrochloride (0.271 g, 1.059 mmol) and following the procedure as outlined in Example 501, N-{4-[2-(4-benzo[d]isothiazol-3-yl-piperazin-1-yl)-ethyl]-2-methyl-phenyl}-N-ethyl-acetamide (0.227 g, 0.494 mmol) was isolated in 100% purity @ 254 nm; LCMS (APCI): 423 $[M+H]^+$; $^1H$ NMR (400 MHz, DMSO-$d_6$) δ 11.37 (bs, 1H), 8.13 (d, J=7.84 Hz, 1H), 8.09 (d, J=7.84 Hz, 1H), 7.57 (t, J=7.12 Hz, 1H), 7.45 (t, J=7.12 Hz, 1H), 7.28 (s, 1H), 7.23–7.11 (m, 2H), 4.07 (bd, J=13.09 Hz, 2H), 3.88 (sextet, J=6.23 Hz, 1H), 3.66 (bd, J=11.22 Hz, 2H), 3.51 (bt, J=11.22 Hz, 2H), 3.45–3.37 (m, 2H), 3.35 (bs, DMSO-$H_2O$), 3.33–3.22 (m, 3H), 2.14 (s, 3H), 1.58 (s, 3H), 0.97 (t, J=7.11 Hz, 3H).

Example 506

N-(4-{2-[4-(1H-INDAZOL-3-YL)-PIPERAZIN-1-YL]-ETHYL}-2-METHYL-PHENYL)-N-ETHYL-ACETAMIDE HYDROCHLORIDE

Starting with N-[4-(2-chloro-ethyl)-2-methyl-phenyl]-N-ethyl-acetamide (0.355 g, 1.479 mmol) and 3-piperazin-1-yl-1H-indazole hydrochloride (0.530 g, 2.218 mmol) and following the procedure as outlined in Example 501, N-(4-{2-[4-(1H-indazol-3-yl)-piperazin-1-yl]-ethyl}-2-methyl-phenyl)-N-ethyl-acetamide hydrochloride (0.09 g, 0.222 mmol).

Yield=15%. 100% purity @ 254 nm; LCMS (APCI): 406.3 $[M+H]^+$; $^1H$ NMR (400 MHz, DMSO-$d_6$) δ 12.19 (s, 1H), 10.46 (bs, 1H), 7.79 (d, J=8.37 Hz, 1H), 7.37 (d, J=8.37 Hz, 1H), 7.32–7.25 (m, 2H), 7.21–7.13 (m, 2H), 6.99 (t, J=7.64 Hz, 1H), 3.97 (bd, J=9.26, 2H), 3.88 (sextet, J=7.13 Hz, 1H), 3.70–3.59 (m, 2H), 3.54 (bs, DMSO-$H_2O$), 3.47–3.35 (m, 2H), 3.33–3.21 (m, 4H), 3.18–3.00 (m, 3H), 2.15 (s, 3H), 1.58 (s, 3H), 0.97 (t, J=7.13 Hz, 3H).

Preparation 49

N-[4-(2-CHLORO-ETHYL)-2-METHYL-PHENYL]-N-PROPYL-ACETAMIDE

N-[4-(2-chloro-ethyl)-2-methyl-phenyl]-N-propyl-acetamide was prepared according to the general method as outlined in Preparation 43 starting from N-[4-(2-chloro-ethyl)-2-methyl-phenyl]-acetamide (0.400 g, 1.89 mmol) and iodopropane (0.230 mL, 2.36 mmol). After chromatographic purification, the product was isolated as a viscous oil (0.432 g, 1.701 mmol). Yield=90%. MS (APCI): 254 $[M+H]^+$; $^1H$ NMR (400 MHz, $CDCl_3D_2O$) δ 7.13 (bs, 1H), 7.07 (bd, J=7.77 Hz, 1H), 7.00 (d, J=7.77 Hz, 1H), 4.8 (bs, $H_2O$/D20), 4.03–3.91 (m, 1H), 3.71 (t, J=8.12 Hz, 2H), 3.11–2.99 (m, 3H), 2.20 (s, 3H), 1.72 (s, 3H), 1.64–1.41 (m, 2H), 0.87 (t, J=6.34 Hz, 3H).

Example 507

N-{4-[2-(4-BENZO[D]ISOTHIAZOL-3L-PIPERAZIN-1-YL)-ETHYL]-2-METHYL-PHENYL}-N-PROPYL-ACETAMIDE HYDROCHLORIDE

N-[4-(2-Chloro-ethyl)-2-methyl-phenyl]-N-propyl-acetamide (0.191 g, 0.753 mmol) was reacted with 3-piperazin-1-yl-benzo[d]isothiazole hydrochloride (0.289 g, 1.13 mmol) according to the method outlined in Example 501. The titled product was precipitated as its hydrochloride salt from dioxane/HCl (gas) treatment (0.250 g, 0.573 mmole). Yield=76%. 100% purity at 254 nm; LCMS (APCI): 437.3 $[M+H]^+$, $^1H$ NMR (400 MHz, DMSO-$d_6$) δ 10.59 (bs, 1H), 8.13 (d, J=8.44 Hz, 1H), 8.09 (d, J=8.44 Hz, 1H), 7.58 (t, J=7.14 Hz, 1H), 7.45 (t, J=7.14 Hz, 1H), 7.27 (s, 1H), 7.21–7.12 (m, 2H), 4.10 (bd, J=13.55 Hz, 2H), 3.87–3.77 (m, 1H), 3.67 (bd, J=11.74 Hz, 2H), 3.48–3.38 (m, 6H), 3.35 (bs, DMSO-$H_2O$), 3.10–2.92 (m, 3H), 2.15 (s, 3H), 1.58 (s, 3H), 1.38 (sextet, J=7.62 Hz, 2H), 0.79 (t, J=7.37 Hz, 3H).

Example 508

N-(4-{2-[4-(1H-INDAZOL-3-YL)-PIPERAZIN-1-YL]-ETHYL}-2-METHYL-PHENYL)-N-PROPYL-ACETAMIDE HYDROCHLORIDE

N-[4-(2-Chloro-ethyl)-2-methyl-phenyl]-N-propyl-acetamide (0.090 g, 0.355 mmole) was reacted with 3-piperazin-1-yl-1H-indazole hydrochloride (0.127 g, 0.532 mmol) according to the method outlined in Example 501. The titled product was precipitated as its hydrochloride salt from dioxane/HCl(gas) treatment (0.030 g, 0.071 mmol). Yield=20%. 100% purity at 254 nm; LCMS (APCI): 437.3 $[M+H]^+$, $^1H$ NMR (400 MHz, DMSO-$d_6$) δ 12.19 (s, 1H), 10.50 (s, 1H), 7.79 (d, J=8.55 Hz, 1H), 7.37 (d, J=8.55 Hz, 1H), 7.32–7.26 (m, 2H), 7.21–7.12 (m, 2H), 6.99 (t, J=7.48 Hz, 1H), 3.97 (bd, J=8.70 Hz, 2H), 3.87–3.77 (m, 1H), 3.65 (bd, J=7.25 Hz, 2H), 3.39 (bs, DMSO-$H_2O$), 3.31–3.21 (m, 6H), 3.10–2.92 (m, 3H), 2.14 (s, 3H), 1.58 (s, 3H), 1.39 (sextet, J=7.38 Hz, 2H), 0.79 (t, 7.38 Hz, 3H).

Preparation 50

N-(2,5-DIMETHYL-PHENYL)-ACETAMIDE

Starting with 2,5-dimethyl-phenylamine (20.00 g, 165.04 mmol) and following the procedure as outlined in Preparation 40, N-(2,5-dimethyl-phenyl)-acetamide was obtained (25.103 g, 153.798 mmol). Yield=93%. MS (APCI): 164.0 $[M+H]^+$; $^1H$ NMR (400 MHz, $CDCl_3$) δ 7.58 (s, 1H), 7.24 (s, CDCl3), 7.05 (d, J=7.00 Hz, 1H), 6.97–6.84 (bs, 1H, NH), 6.88 (d, J=7.00 Hz, 1H), 2.30 (s, 3H), 2.20 (s, 3H), 2.18 (s, 3H).

Preparation 51

N-[4-(2-CHLORO-ACETYL)-2,5-DIMETHYL-PHENYL}-ACETAMIDE

Starting with N-(2,5-dimethyl-phenyl)-acetamide (16.00 g, 98.02 mmol) and following the procedure as outlined in Preparation 41, N-[4-(2-Chloro-acetyl)-2,5-dimethyl-phenyl]-acetamide was obtained. (22.79 g, 95.08 mmol). Yield=97%. 100% purity at 254 nm; LCMS (APCI): 240.3 $[M+H]^+$, 206.3 $(M+H\text{-Chloride})^+$, $^1H$ NMR (400 MHz, DMSO-$d_6$) δ 9.34 (s, 1H), 7.71 (s, 1H), 7.51 (s, 1H), 5.02 (s, 2H), 3.31 (bs, DMSO-$H_2O$), 2.34 (s, 3H), 2.20 (s, 3H), 2.06 (s, 3H).

Preparation 52

N-[4-(2-CHLORO-ETHYL)-2,5-DIMETHYL-PHENYL]-ACETAMIDE

Starting with N-[4-(2-chloro-acetyl)-2,5-dimethyl-phenyl]-acetamide (5.00 g, 20.86 mmol) and following the procedure as outlined in Preparation 42, N-[4-(2-chlor Q-ethyl)-2,5-dimethyl-phenyl]-acetamide was obtained, (4.68 g, 20.75 mmol) with some triethylsilanol contamination (36% by NMR). This compound was taken on and used as is in further processes. Yield=99%. LCMS (APCI): 226.3 $[M+H]^+$, $^1H$ NMR (400 MHz, DMSO-$d_6$) δ 9.16 (s, 1H, NH), 7.13 (s, 1H), 7.00 (s, 1H), 3.74 (t, J=7.33 Hz, 2H), 3.30 (s, DMSO-$H_2O$), 2.92 (t, J=7.33 Hz, 2H), 2.47 (p, DMSO), 2.18 (s, 3H), 2.09 (s, 3H), 1.99 (s, 3H), 0.87 (t, J=7.90 Hz, 5H, $Et_3SiOH$), 0.46 (q, J=7.90 Hz, 3H, $Et_3SiOH$).

Example 509

N-{4-[2-BENZO[D]ISOTHIAZOL-3-YL-PIPERAZIN-1-YL)-ETHYL]-2,5-DIMETHYL-PHENYL}-ACETAMIDE

N-[4-(2-Chloro-ethyl)-2,5-dimethyl-phenyl]-acetamide (1.250 g, 5.54 mmol) was reacted with 3-piperazin-1-yl-benzo[d]isothiazole hydrochloride (2.125 g, 8.31 mmol) according to the method outlined in Example 501. The titled product was obtained as a solid (1.196 g, 2.927 mmol). Yield=53%. 100% purity at 254 nm; LCMS (APCI): 409.3 $[M+H]^+$, $^1H$ NMR (400 MHz, DMSO-$d_6$) δ 9.15 (s, 1H, NH), 8.03 (d, J=7.48 Hz, 2H), 7.53 (t, J=7.48 Hz, 1H), 7.40 (t, J=7.48 Hz, 1H), 7.09 (s, 1H), 6.96 (s, 1H), 3.49–3.38 (m, 4H), 2.73–2.61 (m, 6H), 2.53–2.44 (m, 2H), 2.47 (p, DMSO), 2.20 (s, 3H), 2.08 (s, 3H), 1.99 (s, 3H).

Example 510

N-(4-{2-[4-(1H-INDAZOL-3-YL)-PIPERAZIN-1-YL]-ETHYL}-2.5-DIMETHYL-PHENYL)-ACETAMIDE

N-[4-(2-Chloro-ethyl)-2,5-dimethyl-phenyl]-acetamide (0.142 g, 0.631 mmol) was reacted with 3-piperazin-1-yl-1H-indazole hydrochloride (0.226 g, 0.946 mmol) according to the method outlined in Example 501.

The titled product was precipitated as its hydrochloride salt from dioxane/HCl(gas) treatment (0.131 g, 0.334 mmol). Yield=53%. 100% purity at 254 nm; LCMS (APCI): 392.3 $[M+H]^+$, $^1H$ NMR (400 MHz, DMSO-$d_6$) δ 11.92 (s, 1H), 9.15 (s, 1H), 7.69 (d, J=8.47 Hz, 1H), 7.30 (d, J=8.47 Hz, 1H), 7.22 (t, J=6.59 Hz, 1H), 7.07 (s, 1H), 6.94 (s, 1H), 6.93 (t, J=6.59 Hz, 1H), 3.29 (bs, $H_2O$), 2.70–2.60 (m, 6H), 2.50–2.40 (m, 6H), 2.20 (s, 3H), 2.15 (s, 3H), 2.00 (s, 3H), 1.10 (s, 2H).

Example 511

N-(4-{2-[4-(1H-INDAZOL-3-YL)-PIPERAZIN-1-YL]-ETHYL}-2-M ETHYL-PHENYL)-ACETAMIDE

Starting with N-[4-(2-chloro-ethyl)-2-methyl-phenyl]-acetamide (0.194 g, 0.915 mmol) and 3-piperazin-1-yl-1H- indazole hydrochloride (0.328 g, 1.372 mmol), and following the procedure outlined in Example 501, N-(4-{2-[4-(1H-indazol-3-yl)-piperazin-1-yl]-ethyl}-2-methyl-phenyl)-acetamide was obtained as its hydrochloride salt (0.038 g, 0.101 mmol).

Yield=11%; 96% purity at 254 nm; LCMS (APCI): 378.3 $[M+H]^+$, $^1$H NMR (400 MHz, DMSO-$d_6$) δ12.20 (s, 1H), 10.46 (bs, 1H), 9.27 (s, 1H), 7.78 (d, J=8.19 Hz, 1H), 7.37 (d, J=8.19 Hz, 1H), 7.33 (d, J=8.19 Hz, 1H), 7.29 (t, J=7.61 Hz, 1H), 7.10 (s, 1H), 7.04 (d, J=8.19 Hz, 1H), 6.99 (t, J=7.61, 1H), 3.96 (bd, J=7.18 Hz, 2H), 3.89 (bs, $H_2O$), 3.63 (bd, J=7.18 Hz, 2H), 3.43–3.20 (m, 6H), 3.03–2.94 (m, 2H), 2.16 (s, 3H), 2.02 (s, 3H).

Preparation 53

4-[2-(4-BENZO[D]ISOTHIAZOL-3-YL-PIPERAZIN-1-YL)-ETHYL]-2-METHYL-PHENYLAMINE HYDROCHLORIDE

N-{4-[2-(4-Benzo[d]isothiazol-3-yl-piperazin-1-yl)-ethyl]-2-methyl-phenyl}-acetamide (1.760 g, 4.462 mmol) was heated to reflux in 1,4-dioxane (25 mL) and 25% aqueous potassium hydroxide (25 mL). After 20 days the reaction was complete and diluted with $H_2O$ (100 mL), and ethylacetate (100 mL). The layers were separated and the aqueous layer extracted with ethylacetate (3×50 mL). The organics were dried ($MgSO_4$) and concentrated to a residue. 4-[2-(4-Benzo[d]isothiazol-3-yl-piperazin-1-yl)-ethyl]-2-methyl-phenylamine was precipitated as its hydrochloride salt from dioxane/HCl(gas) treatment (1.572 g, 4.46 mmol). Yield=100%. 100% purity at 254 nM; LCMS (APCI): 353.3 $[M+H]^+$, $^1$H NMR (400 MHz, DMSO-$d_6$) δ 8.02 (d, J=8.92 Hz, 1H), 7.52 (t, J=7.3 Hz, 1H), 7.40 (t, J=7.30 Hz, 1H), 6.76 (s, 1H), 6.72 (d, J=7.30, 1H), 6.49 (d, J=7.30 Hz, 1H), 2.02 (bs, 1H), 3.46–3.20 (m, 5H), 3.14 (s, $H_2O$), 2.67–2.59 (m, 4H), 2.59–2.48 (m, 3H), 1.98 (s, 3H), 1.87 (s, 1H).

Example 512

N-{4-[2-(4-BENZO[D]ISOTHIAZOL-3-YL-PIPERAZIN-1-YL)-ETHYL]-2-METHYL-PHENYL}-BENZAMIDE HYDROCHLORIDE

To a solution of 4-[2-(4-benzo[d]isothiazol-3-yl-piperazin-1-yl)-ethyl]-2-methyl-phenylamine Hydrochloride (0.224 g, 0.6 mmol) in dry THF (30 mL) was added triethylamine (0.167 mL, 1.20 mmol), followed by dropwise addition of benzoyl chloride (0.07 mL, 0.6 mmol). The reaction was stirred vigorously under $N_2$ blanket at room temperature for 2 h. The reaction was quenched with $H_2O$ (25 mL) and diluted with ethylacetate (25 mL). The layers were separated and the organics washed with 1 N HCl (20 mL), sat. $Na_2CO_3$ (20 mL), brine (20 mL), dried ($MgSO_4$), and concentrated to a residue. After chromatographic purification (5% MeOH/$CH_2Cl_2$), N-{4-[2-(4-benzo[d]isothiazol-3-yl-piperazin-1-yl)-ethyl]-2-methyl-phenyl}-benzamide was precipitated as its hydrochloride salt from dioxane/HCl(gas) treatment (0.162 g, 0.355 mmol). Yield=59%. 100% purity at 254 nM; LCMS (APCI): 457.2 $[M+H]^+$, $^1$H NMR (400 MHz, DMSO-$d_6$) δ 10.81 (bs, 1H), 9.88 (s, 1H), 8.13 (d, J=8.36 Hz, 1H), 8.09 (d, J=8.36 Hz, 1H), 7.95 (d, J=8.36 Hz, 1H), 7.62–7.42 (m, 5H), 7.30 (d, J=8.02 Hz, 1H), 7.18 (s, 1H), 7.12 (d, J=8.02 Hz, 1H), 4.10 (bd, J=12.32 Hz, 2H), 3.68 (bd, J=12.32 Hz, 2H), 3.50–3.33 (m, 6H), 3.32 (s, $H_2O$), 3.10–3.00 (m, 2H), 2.47 (DMSO), 2.21 (s, 3H).

Example 513

N-{4-[2-(4-BENZO[D]ISOTHIAZOL-3-YL-PIPERAZIN-1-YL)-ETHYL]-2-METHYL-PHENYL}-ACRYLAMIDE

Starting with 4-[2-(4-benzo[d]isothiazol-3-yl-piperazin-1-yl)-ethyl]-2-methyl-phenylamine hydrochloride (0.60 g, 1.702 mmol) and acryloyl chloride (0.138 mL, 1.702 mmol) and following the procedure outlined in Example 512, N-{4-[2-(4-benzo[d]isothiazol-3-yl-piperazin-1-yl)-ethyl]-2-methyl-phenyl}-acrylamide (0.512 g, 1.259 mmol) was obtained. Yield=74%. 100% purity at 254 nM; LCMS (APCI): 407.3 $[M+H]^+$; $^1$H NMR (400 MHz, DMSO-$d_6$) δ 11.02 (bs, 1H), 9.50 (s, 1H), 8.11 (d, J=8.22 Hz, 1H), 8.07 (d, J=8.22 Hz, 1H), 7.55 (t, J=7.3 Hz, 1H), 7.45–7.37 (m, 2H), 7.11 (s, 1H), 7.05 (d, 7.63 Hz, 1H), 6.50 (dd, J=10.09, J=17.08, 1H), 6.18 (dd, J=2.13 Hz, J=17.08 Hz, 1H), 5.69 (dd, J=2.05 Hz, J=10.05 hz, 1H), 4.10–4.00 (m, 2H), 3.70–3.59 (m, 2H), 3.50–3.33 (m, 4H), 3.29–3.21 (m, 1H), 3.07–2.95 (m, 2H), 2.16 (s, 3H).

Example 514

N-{4-[2-(4-BENZO[D]ISOTHIAZOL-3-YL-PIPERAZIN-1-YL)-ETHYL]-2-METHYL-PHENYL}-2-METHYL-ACRYLAMIDE

Starting with 4-[2-(4-benzo[d]isothiazol-3-yl-piperazin-1-yl)-ethyl]-2-methyl-phenylamine hydrochloride (0.6 g, 1.702 mmol) and 2-methyl-acryloyl chloride (0.206 mL, 1.702 mmol) and following the procedure outlined in Example 512, N-{4-[2-(4-Benzo[d]isothiazol-3-yl-piperazin-1-yl)-ethyl]-2-methyl-phenyl}-2-methyl-acrylamide (0.521 g, 1.239 mmole) was obtained. Yield=73%. 100% purity at 254 nM; LCMS (APCI): 421.3 $[M+H]^+$; $^1$H NMR (400 MHz, DMSO-$d_6$) δ11.17 (bs, 1H), 9.32 (s, 1H), 8.10 d, J=7.88 Hz, 1H), 8.07 (d, J=7.88 Hz, 1H), 7.55 (t, J=7.88 Hz, 1H), 7.43 (t, J=7.88 Hz, 1H), 7.19 (d, J=7.88 Hz, 1H), 7.11 (s, 1H), 7.05 (d, J=7.88 Hz, 1H), 5.80 (s, 1H), 5.44 (s, 1H), 4.05 (bd, J=12.08 Hz, 2H), 3.63 (bd, J=12.08 Hz, 2H), 3.51–3.32 (m, 5H), 3.31 (s, $H_2O$), 3.29–3.22 (m, 1H), 3.07–2.98 (m, 2H), 2.12 (s, 3H), 1.90 (s, 3H).

Example 515

BUT-2-ENOIC ACID{4-[2-(4-BENZO[D]ISOTHIAZOL-3-YL-PIPERAZIN-1-YL)-ETHYL]-2-METHYL-PHENYL]AMIDE

Starting with 4-[2-(4-benzo[d]isothiazol-3-yl-piperazin-1-yl)-ethyl]-2-methyl-phenylamine hydrochlQride (0.60 g, 1.702 mmol) and 3-methyl-acryloyl chloride (0.163 mL, 1.702 mmol) and following the procedure outlined in Example 512, but-2-enoic acid{4-[2-(4-benzo[d]isothiazol-3-yl-piperazin-1-yl)-ethyl]-2-methyl-phenyl]amide (0.553 g, 1.315 mmol) was obtained. Yield=77%. 100% purity at 254 nM; LCMS (APCI): 421.3 $[M+H]^+$; $^1$H NMR (400 MHz, DMSO-$d_6$) δ 9.17 (s, 1H), 8.01 (d, J=8.53 Hz, 1H), 7.51 (t, J=8.01 Hz, 1H), 7.38 (t, J=8.01 Hz, 1H), 7.29 (d, J=8.01 Hz, 1H), 7.04 (s, 1H), 6.99 (d, J=8.01 Hz, 1H), 6.70 (dq, J=6.86 Hz, J=15.27 Hz, 1H), 6.15 (d, J=15.32 Hz, 1H), 3.44–3.35 (m, 4H), 3.29 (s, $H_2O$), 2.72-s.58 (m, 6H), 2.57–2.49 (m, 2H), 2.11 (s, 3H), 1.80 (d, J=6.89 Hz, 3H).

Example 516

3-METHYL-BUT-2-ENOIC ACID{4-[2-(4-BENZO[D]ISOTHIAZOL-3-YL-PIPERAZIN-1-YL)-ETHYL]-2-METHYL-PHENYL]AMIDE

Starting with 4-[2-(4-benzo[d]isothiazol-3-yl-piperazin-1-yl)-ethyl]-2-methyl-phenylamine hydrochloride (0.60 g, 1.702 mmol) and 3,3-dimethyl-acryloyl chloride (0.189 mL, 1.702 mmol) and following the procedure outlined in Example 512, 3-methyl-but-2-enoic acid{4-[2-(4-benzo[d]isothiazol-3-yl-piperazin-1-yl)-ethyl]-2-methyl-phenyl]amide (0.553 g, 1.261 mmol) was obtained. Yield=75%. 100% purity at 254 nM; LCMS (APCI): 435.3 $[M+H]^+$; $^1H$ NMR (400 MHz, DMSO-$d_6$) δ 9.05 (s, 1H), 8.00 (d, J=8.42 Hz, 2H), 7.50 (t, J=7.47 Hz, 1H), 7.38 (t, J=7.47 Hz, 1H), 7.26 (d, J=7.47 Hz, 1H), 7.02 (s, 1H), 6.97 (d, J=7.47 Hz, 1H), 5.90 (s, 1H), 3.44–3.36 (m, 4H), 3.30 (s, $H_2O$), 2.71–2.58 (m, 6H), 2.57–2.49 (m, 2H), 2.45 (p, DMSO), 2.11 (s, 3H), 2.07 (s, 3H), 1.80 (s, 3H).

Example 517

N-{4-[2-(4-BENZO[D]ISOTHIAZOL-3-YL-PEPERAZIN-1-YL)-ACETYL]-5-CHLORO-2-METHYL-PHENYL}-ACETAMIDE

To a solution of N-[5-Chloro-4-(2-chloro-acetyl)-2-methyl-phenyl]-acetamide (1.375 g, 5.286 mmol), in acetonitrile (50 mL) was added 3-piperazin-1-yl-benzo[d]isothiazole hydrochloride (1.352 g, 5.286 mmol), potassium iodide (1 eq), and potassium carbonate (1.5 eq). The reaction was stirred as a suspension at rt overnight. The reaction was diluted with $H_2O$ and the filtered. After drying at 50° C. under high vacuum overnight, N-{4-[2-(4-benzo[d]isothiazol-3-yl-peperazin-1-yl)-acetyl]-5-chloro-2-methyl-phenyl}-acetamide was collected as a white solid (2.034 g, 4.598 mmol). Yield=87%. 100% pure at 254 nM; LCMS (APCI): 443.3 $[M+H]^+$;

$^1H$ NMR (400 MHz, DMSO-$d_6$) δ 9.41 (s, 1H), 8.02 (d, J=8.80 Hz, 2H), 7.81 (s, 1H), 7.59 (s, 1H), 7.52 (t, J=7.34 Hz, 1H), 7.39 (t, J=7.34 Hz, 1H), 3.80 (s, 2H), 3.44–3.37 (m, 4H), 3.30 (s, H2O), 2.77–2.68 (m, 4H), 2.23 (s, 3H), 2.08 (s, 3H).

Example 518

N-{4-[2-(4-BENZO[D]ISOTHIAZOL-3-YL-PEPERAZIN-1-YL)-1-HYDROXY-ETHYL]-5-CHLORO-2-METHYL-PHENYL}-ACETAMIDE

To a suspension of N-{4-[2-(4-benzo[d]isothiazol-3-yl-peperazin-1-yl)-acetyl]-5-chloro-2-methyl-phenyl}-acetamide (0.750 g, 1.693 mmol) in ethanol (25 mL), was added sodium borohydride (0.096 g, 2.54 mmol). The reaction was stirred at rt for 2 h after which the reaction was complete. The reaction was diluted with $H_2O$ (50 mL) and stirred for 10 min. The white suspension was collected by filtration then taken up in MeOH (100 mL) and glacial acetic acid (5 mL). The solvents were stripped away and the MeOH/AcOH strip repeated (3×). The residue was taken up in $H_2O/CHCl_3$ and washed with 1N NaOH (3×50 mL), dried ($MgSO_4$), and concentrated to give N-{4-[2-(4-benzo[d]isothiazol-3-yl-peperazin-1-yl)-1-hydroxy-ethyl]-5-chloro-2-methyl-phenyl}-acetamide as a white solid (0.654 g, 1.47 mmol). Yield=87%. 100% purity at 254 nM. $^1H$ NMR (400 MHz, $CDCl_3$) δ 7.89 (d, J=8.03 Hz, 1H), 7.84 9s, 1H), 7.80 (d, J=8.03 Hz, 1H), 7.48–7.42 (m, 2H), 7.34 (t, J=7.59 Hz, 1H), 7.24 (s, $CDCl_3$), 7.10 (bs, 1H, NH), 5.15 (d, J=10.68 Hz, 1H), 3.66–3.51 (m, 4H), 3.04–2.96 (m, 2H), 2.83–2.75 (m, 1H), 2.75–2.66 (m, 2H), 2.36 (t, J=10.99 Hz, 1H), 2.21 (s, 3H), s.18 (s, 3H).

Preparation 54

N-(5-FLUORO-2-METHYL-PHENYL)-ACETAMIDE

Starting with 5-fluoro-2-methyl aniline (3.00 g, 23.97 mmol), and following the procedure as outlined in Preparation 40, N-(5-fluoro-2-methyl-phenyl)-acetamide (3.78 g, 22.6 mmol) was obtained. Yield=94%. MS (APCI): 167.9 $[M+H]^+$ Preparation 55

N-{4-(2-CHLORO-ACETYL)-5-FLUORO-2-METHYL-PHENYL}-ACETAMIDE

Starting with N-(5-fluoro-2-methyl-phenyl)-acetamide (3.50 g, 20.93 mmol) and following the procedure as outlined in Preparation 41, N-[4-(2-chloro-acetyl)-5-fluoro-2-methyl-phenyl]-acetamide (4.44 g, 18.21 mmol) was prepared. Yield=87%. MS (APCI): 244.0 $[M+H]^+$ Preparation 56

N-{4-[2-(4-BENZO[D]ISOTHIAZOL-3-YL-PEPERAZIN-1-YL)-ACETYL]-5-FLUORO-2-METHYL-PHENYL}-ACETAMIDE

Starting with N-[4-(2-chloro-acetyl)-5-fluoro-2-methyl-phenyl]-acetamide (3.00 g, 12.31 mmol), and following the procedure as outlined in Example 515, N-{4-[2-(4-benzo[d]isothiazol-3-yl-peperazin-1-yl)-acetyl]-5-fluoro-2-methyl-phenyl}-acetamide was prepared (3.25 g, 7.62 mmol).

Yield=62%. MS (APCI): 427 $[M+H]^+$; $^1H$ NMR (400 MHz, DMSO-$d_6$) δ 9.38 (s, 1H), 8.02 (d, J=8.23 Hz, 2H), 7.75 (d, J=13.72 Hz, 1H), 7.66 (d, J=8.40 Hz, 1H), 7.52 (t, J=7.56 Hz, 1H), 7.40 (t, J=7.56 Hz, 1H), 3.79 (s, 2H), 3.45–3.35 (m, 4H), 3.30 (s, $H_2O$), 2.76–2.66 (m, 4H), 2.24 (s, 3H), 2.12 (s, 3H).

Example 519

N-{4-[2-(4-BENZO[D]ISOTHIAZOL-3-YL-PEPERAZIN-1-YL)-1-HYDROXY-ETHYL]-5-FLUORO-2-METHYL-PHENYL}-ACETAMIDE

Starting with N-{4-[2-(4-benzo[d]isothiazol-3-yl-peperazin-1-yl)-acetyl]-5-fluoro-2-methyl-phenyl}-acetamide (3.11 g, 7.29 mmol), and following the procedure outlined in Example 518, N-{4-[2-(4-benzo[d]isothiazol-3-yl-peperazin-1-yl)-1-hydroxy-ethyl]-5-fluoro-2-methyl-phenyl}-acetamide (3.01 g, 7.02 mmol) was obtained. Yield=96%. 100% purity at 254 nM; LCMS (APCI): 429.2 $[M+H]^+$; $^1H$ NMR (400 MHz, DMSO-$d_6$) δ 9.24 (s, 1H), 8.02 (d, J=8.42 Hz, 2H), 7.52 (t, J=7.36 Hz, 1H), 7.39 (t, J=7.36 Hz, 1H), 7.35–7.25 (m, 2H), 5.20 (bs, 1H), 5.03–4.94 (m, 1H), 3.46–3.35 (m, 4H), 3.30 (s, $H_2O$), 2.74–2.64 (m, 4H), 2.61–2.52 (m, 1H), 2.16 (s, 3H), 2.04 (s, 3H).

Preparation 57

N-[5-(2-CHLORO-ACETYL)-2-ISOPROPYL-PHENYL]-ACETAMIDE, N-[2-(2-CHLORO-ACETYL)-5-ISOPROPYL-PHENYL]-ACETAMIDE, AND N-[4-(2-CHLORO-ACETYL)-3-ISOPROPYL-PHENYL]-ACETAMIDE

Starting with N-(2-Isopropyl-phenyl)-acetamide (3.54 g, 19.97 mmol) and following the procedure as outlined in Preparation 41, three regioisomers were obtained. N-[5-(2-Chloro-acetyl)-2-isopropyl-phenyl]-acetamide (0.61 g, 2.39 mmol) Yield=12%. 100% purity at 254 nM. LCMS (APCI): 254.3 $[M+H]^+$; $^1H$ NMR (400 MHz, DMSO-$d_6$) δ 9.51 (s, 1H), 7.81 (s, 1H), 7.77 (d, J=8.23 Hz, 1H), 7.45 (d, J=8.23 Hz, 1H), 5.11 (s, 2H), 3.30 (s, $H_2O$), 3.17 (heptet, 6.83 Hz, 1H), 2.04 (s, 3H), 1.12 (d, J=6.83 Hz, 6H). N-[2-(2-Chloro-acetyl)-5-isopropyl-phenyl]-acetamide. Yield=10%. 100% purity at 254 nm. LCMS (APCI): 254.3 $[M+H]^+$; $^1H$ NMR (400 MHz, DMSO-$d_6$) δ 10.79 (s, 1H), 7.98 (s, 1H), 7.79 (d, J=8.19 Hz, 1H), 7.08 (d, J=8.19 Hz, 1H), 5.06 (s, 2H), 3.36 (bs, $H_2O$), 2.89 (heptet, J=6.80 Hz, 1H), 2.47 (p, DMSO), 2.07 (s, 3H), 1.17 (d, J=6.80 Hz, 6H). N-[4-(2-Chloro-acetyl)-3-isopropyl-phenyl]-acetamide Yield=34%. 100% purity at 254 nm. LCMS (APCI): 254.3 $[M+H]^+$ Example 520

N-{5-[2-(4-BENZO[D]ISOTHIAZOL-3-YL-PIPERAZIN-1-YL)-ACETYL]-2-ISOPROPYL-PHENYL}-ACETAMIDE HYDROCHLORIDE

Starting with N-[5-(2-chloro-acetyl)-2-isopropyl-phenyl]-acetamide (0.50 g, 1.971 mmol), and 3-piperazin-1-yl-benzo[d]isothiazole hydrochloride (0.504 g, 1.971 mmol) and following the procedure as outlined in Example 517, N-{5-[2-(4-benzo[d]isothiazol-3-yl-piperazin-1-yl)-acetyl]-2-isopropyl-phenyl}-acetamide (0.480 g, 1.099 mmol) was obtained as its hydrochloride salt from treatment with dioxane/HCl(gas). Yield=56%. 100% purity at 254 nM. $^1H$ NMR (400 MHz, DMSO-$d_6$) δ 10.46 (bs, 1H), 9.63 (s, 1H), 8.12 (d, J=8.13 Hz, 1H), 8.09 (d, J=8.13 Hz, 1H), 7.90 (s, 1H), 7.79 (d, J=8.13 Hz, 1H), 7.61–7.52 (m, 2H), 7.45 (t, J=7.47 Hz, 1H), 5.13 (s, 2H), 4.12–4.01 (m, 2H), 3.67–3.49 (m, 8H), 3.40 (bs, $H_2O$), 3.37–3.30 (m, 1H), 3.23 (heptet, J=6.81 Hz, 1H), 2.07 (s, 3H), 1.14 (d, J=6.81 Hz, 6H).

Example 521

N-{2-[2-(4-BENZO[D]ISOTHIAZOL-3-YL-PIPERAZIN-1-YL)-ACETYL]-5-ISOPROPYL-PHENYL}-ACETAMIDE HYDROCHLORIDE

Starting with N-[2-(2-chloro-acetyl)-5-isopropyl-phenyl]-acetamide (0.30 g, 1.182 mmol), and 3-piperazin-1-yl-benzo[d]isothiazole hydrochloride (0.302 g, 1.182 mmol) and following the procedure as outlined in Example 517, N-{2-[2-(4-benzo[d]isothiazol-3-yl-piperazin-1-yl)-acetyl]-5-isopropyl-phenyl}-acetamide (0.375 g, 0.859 mmol) was obtained as its hydrochloride salt from treatment with dioxane/HCl(gas). Yield=73%. 100% purity at 254 nM. $^1H$ NMR (400 MHz, DMSO-$d_6$) δ 10.71 (s, 1H), 10.36 (bs, 1H), 8.14 (d, J=8.24 Hz, 1H), 8.09 (d, J=8.24 Hz, 1H), 7.78–7.72 (m, 2H), 7.58 (t, J=7.56 Hz, 1H), 7.45 (t, J=7.56 Hz, 1H), 7.18 (d, J=8.24 Hz, 1H), 5.00 (s, 2H), 4.13–4.01 (m, 2H), 3.68–3.44 (m, 6H), 3.40 (s, $H_2O$), 2.93 (heptet, J=6.95 Hz, 1H), 2.08 (s, 3H), 1.19 (d, J=6.95 Hz, 6H).

Example 522

N-{4-[2-(4-BENZO[D]ISOTHIAZOL-3-YL-PIPERAZIN-1-YL)-ACETYL]-3-ISOPROPYL-PHENYL}-ACETAMIDE HYDROCHLORIDE

Starting with N-[4-(2-chloro-acetyl)-3-isopropyl-phenyl]-acetamide (0.876 g, 3.453 mmol), and 3-piperazin-1-yl-benzo[d]isothiazole hydrochloride (0.883 g, 3.453 mmol) and following the procedure as outlined in Example 517, N-{4-[2-(4-benzo[d]isothiazol-3-yl-piperazin-1-yl)-acetyl]-3-isopropyl-phenyl}-acetamide (0.1.0 g, 2.302 mmol) was obtained as its hydrochloride salt from treatment with dioxane/HCl(gas). Yield=67%. 100% purity at 254 nM. $^1H$ NMR (400 MHz, DMSO-$d_6$) δ 10.44–10.29 (bm, 2H), 8.13 (d, J=8.49 Hz, 1H), 8.09 (d, J=8.49 Hz, 1H), 7.81 (d, J=9.12 Hz, 1H), 7.73–7.68 (m, 2H), 7.57 (t, J=7.49 Hz, 1H), 7.45 (t, J=7.49 Hz, 1H), 5.04 (s, 2H), 4.13–4.02 (m, 2H), 3.76–3.45 (m, 18H, $H_2O$), 2.06 (s, 3H), 1.18 (d, J=6.85 Hz, 6H).

Example 523

N-{4-[2-(4-BENZO[D]ISOTHIAZOL-3-YL-PIPERAZIN-1-YL)-ACETYL]-2-ISOPROPYL-PHENYL}-ACETAMIDE HYDROCHLORIDE

Starting with N-[4-(2-Chloro-acetyl)-2-isopropyl-phenyl]-acetamide (0.380 g, 1.498 mmole), and 3-piperazin-1-yl-benzo[d]isothiazole hydrochloride (0.383 g, 1.498 mmole, 1.0 eq) and following the procedure as outlined in Example 17, N-{4-[2-(4-Benzo[d]isothiazol-3-yl-piperazin-1-yl)-acetyl]-2-isopropyl-phenyl}-acetamide (0.360 g, 0.825 mmole) was obtained as its hydrochloride salt from treatment with dioxane/HCl(gas).

Yield=55%. 100% purity at 254 nM. $^1H$ NMR (400 MHz, DMSO-$d_6$) δ 10.36 (s, 2H), 10.42–10.26 (bs, 1H), 8.12 (d, J=8.19 Hz, 1H), 8.09 (d, J=8.19 Hz, 1H), 7.81 (d, J=8.46 Hz, 1H), 7.81 (d, J=8.46 Hz, 1H), 7.73–7.68 (m, 2H), 7.57 (t, J=7.49 Hz, 1H), 7.45 (t, J=7.49 Hz, 1H), 5.04 (s, 2H), 4.13–3.99 (m, 2H), 3.79–3.54 (m, 5H), 3.53 (s, MeOH), 3.49 (s, $H_2O$), 2.47 (p, DMSO), 2.06 (s, 3H), 1.18 (d, J=6.90 Hz, 6H).

Preparation 58

N-(2,6-DIMETHYL-PHENYL)-ACETAMIDE

Starting with 2,6-dimethyl aniline (5.00 mL, 41.26 mmol), and following the procedure outlined in Preparation 40, N-(2,6-dimethyl-phenyl)-acetamide (6.55 g, 40.11 mmol) was obtained. Yield=97%. MS (APCI): 164.0 $[M+H]^+$ Preparation 59

N-{3-(2-CHLORO-ACETYL)-2,6-DIMETHYL-PHENYL}-ACETAMIDE

Starting with N-(2,6-dimethyl-phenyl)-acetamide (2.50 g, 15.32 mmol) and following the procedure as outlined in Preparation 41, N-[3-(2-chloro-acetyl)-2,6-dimethyl-phenyl]-acetamide (3.404 g, 14.20 mmol) was obtained. Yield=93%. $^1H$ NMR (400 MHz, DMSO-$d_6$) δ 9.34 (s, 1H), 7.59 (d, J=7.83 Hz, 1H), 7.18 (d, J=7.83 Hz, 1H), 5.02 (s, 2H), 3.31 (s, $H_2O$), 2.15 (s, 3H), 2.14 (s, 3H), 2.03 (s, 3H).

Example 524

N-{3-[2-(4-BENZO[D]ISOTHIAZOL-3-YL-PIPERAZIN-1-YL)-ACETYL]-2,6-DIMETHYL-PHENYL}-ACETAMIDE HYDROCHLORIDE

Starting with N-[3-(2-chloro-acetyl)-2,6-dimethyl-phenyl]-acetamide (0.250 g, 1.04 mmol), and 3-piperazin-1-yl-benzo[d]isothiazole hydrochloride (0.290 g, 1.15 mmol) and following the procedure as outlined in Example 517, N-{3-[2-(4-benzo[d]isothiazol-3-yl-piperazin-1-yl)-acetyl]-2,6-dimethyl-phenyl}-acetamide (0.285 g, 0.67 mmol) was obtained as its hydrochloride salt from treatment with dioxane/HCl(gas). Yield=65%. 100% purity at 254 nM. $^1$H NMR (400 MHz, DMSO-$d_6$) δ 9.29 (s, 2H), 8.00 (d, J=8.04 Hz, 2H), 7.55–7.47 (m, 2H), 7.38 (t, J=8.04 Hz, 1H), 7.14 (t, J=8.04 Hz, 1H), 3.76 (s, 2H), 4.13–3.99 (m, 2H), 3.42–3.36 (m, 4H), 3.28 (s, $H_2O$), 2.45 (p, DMSO), 2.14–2.11 (m, 6H), 2.01 (s, 3H).

Preparation 60

6-[2-(4-1,2-Benzoisothiazol-3-yl-piperazin-1-yl)-ethyl]-2-methyl-Pyridin-3-ylamine and 6-[2-(4-1,2-Benzoisothiazol-3-yl-piperazin-1-yl)-ethyl]-2-methyl-pyridin-5-ylamine A round bottomed flask was charged with 5 g (22.8 mmol) of 3-(1-piperazinyl)-1,2-benzisothiazole and 20 mL dimethylformamide dimethylacetal. The solution was heated to 90° C. for 20 h and then concentrated in vacuo. The resulting yellow solid was treated with 3.76 g (2,6-dimethyl-3-nitropyridine in 22 mL DMF and heated to 100° C. for 48 h. The reaction was then cooled and concentrated in vacuo. This crude reaction product was dissolved in 90 mL dichloroethane and 1.9 mL (33 mmol) HOAc, cooled to 0° C., and treated with 9.4 g (44 mmol) $NaBH(OAc)_3$. The reaction was allowed to warm to rt overnight and then stirred for 90 h. The reaction was quenched with 200 mL $K_2CO_3$ and 100 mL $CH_2Cl_2$. The organic extracts were dried over $MgSO_4$, filtered, and concentrated in vacuo to give 15.5 g of a red liquid. This red liquid was crudely purified by filtration chromatography to give 5.3 g of a crude mixture of the desired nitro compounds as an approximate 1:1 mixture. This crude mixture was hydrogenated (50 psi) for ~65 h in 100 mL THF:triethylamine (19:1) using RaNi catalyst. The reaction was filtered and concentrated to give 5 g of crude material which was purified by $SiO_2$ chromatography using a gradient of EtOAc to 10% MeOH/EtOAc. This purification gave 0.30 g of isomer A and 0.46 g of isomer B, both as orange oils. Additionally, 1.1 g of a fraction containing both isomers was isolated. Isomer A: MS (APCI): 354 $[M+H]^+$. Isomer B: MS (APCI): 354 $[M+H]^+$.

Example 525

N-{6-[2-(4-1,2-BENZISOTHIAZOL-3-YL-PIPERAZIN-1-YL)-ETHYL]-2-METHYL-PYRIDIN-3-YL}-ACETAMIDE

A 2 dram vial was charged with 0.1004 g (0.28 mmol) of isomer B and 3 mL $CH_2Cl_2$. To this solution was added 83 μL (2.1 eq, 0.59 mmol) $Et_3N$ and 22 μL (1.1 eq, 0.31 mmol) $CH_3COCl$. The reaction was stirred for 8 h at rt at which time it was quenched with 2 mL 1 M $NaHCO_3$ and filtered through a 1.0 μM PTFE filter. Concentration of the resulting solution gave 0.098 g of the crude, desired product as a white solid. This crude material was purified by gravity chromatography ($SiO_2$, 10% MeOH/EtOAc) to give 0.0536 g (48% yield) of the purified material. This product was identified as N-{6-[2-(4-1,2-Benzisothiazol-3-yl-piperazin-1-yl)-ethyl]-2-methyl-pyridin-3-yl}-acetamide by $^1$H NMR (ROESY). $^1$H NMR (400 MHz, $CDCl_3$) δ ppm 2.2 (s, 3H), 2.5 (s, 3H), 2.7 (s, 4H), 2.8 (s, 2H), 3.0 (s, 2H) 3.6 (s, 4H), 7.0 (d, J=8.3 Hz, 1H), 7.2 (s, 1H), 7.3 (m, 1H), 7.4 (td, J=7.5, 1.1 Hz, 1H), 7.8 (d, J=8.1 Hz, 1H), 7.9 (d, J=8.1 Hz, 1H), 8.0 (d, J=8.3 Hz, 1H). [M+H]+=396.

Example 526

N-{6-[2-(4-1,2-BENZISOTHIAZOL-3-YL-PIPERAZIN-1-YL)-ETHYL]-2-METHYL-PYRIDIN-5-YL}-ACETAMIDE

Isomer A (0.0949 g) was submitted to the same reaction conditions and purification methods to yield 0.0874 g (quantitative yield) of the desired material as an orange oil. $^1$H NMR (ROESY) experiments provided evidence that this product was N-{6-[2-(4-1,2-Benzisothiazol-3-yl-piperazin-1-yl)-ethyl]-2-methyl-pyridin-5-yl}-acetamide. $^1$H NMR (400 MHz, $CDCl_3$) δ ppm 2.2 (s, 3H), 2.5 (s, 3H), 2.8 (s, 6H), 3.0 (s, 2H), 3.6 (s, 4 H), 7.0 (d, J=8.3 Hz, 1H), 7.3 (t, J=7.6 Hz, 1H), 7.4 (t, J=7.6 Hz, 1H), 7.8 (d, J=8.1 Hz, 1H), 7.8 (d, J=8.1 Hz, 1H), 8.1 (d, J=8.3 Hz, 1H), 10.2 (s, 1H). $[M+H]^{30}$ =396.

Example 527

2-{4-[2-(4-BENZO[D]ISOTHIAZOL-3-YL-PIPERAZIN-1-YL)-ETHYL]-PHENYL}-2,3-DIHYDRO-ISOINDOL-1-ONE

4-[2-(4-Benzo[d]isothiazol-3-yl-piperazin-1-yl)-ethyl]-phenylamine (338.4 mg, 1.0 mmol) was reacted at reflux for 30 min with o-phthaldialdehyde (147.5 mg, 1.1 mmol) and a catalytic amount of acetic acid (57 μL, 0.1 mmol) in acetonitrile (100 mL) to give the title compound. The product obtained was purified by elution through a flash column (silica gel 40, 230–400 mesh, 100:8:1, $CH_2Cl$: EtOH:$NH_4OH$) to give a yellow crystalline material, yield=245 mg (53.9%). mp 175.9° C. MS (APCI): 455 $[M+H]^+$. $^1$H-NMR (dmso-$d_6$, δ): 2.59 (m, 2H) 2.66 (m, 4H) 2.77 (m, 2H) 3.43 (m, 4H) 4.98 (s, 2H) 7.30 (d, J=8.79 Hz, 2H) 7.40 (dd, J=8.67, 7.45 Hz, 1H) 7.52 (m, 2H) 7.64 (m, 2H) 7.77 (m, 3H) 8.03 (d, J=9.28 Hz, 2H).

Example 528

2-{3-[2-(4-BENZO[D]ISOTHIAZOL-3-YL-PIPERAZIN-1-YL)-ETHYL]-PHENYL}-2,3-DIHYDRO-ISOINDOL-1-ONE

2-{3-[2-(4-Benzo[d]isothiazol-3-yl-piperazin-1-yl)-ethyl]-phenyl}-2,3-dihydro-isoindol-1-one was prepared according to the general method as outlined in Example 527 starting from 3-[2-(4-Benzo[d]isothiazol-3-yl-piperazin-1-yl)-ethyl]-phenylamine, yield=108 mg (39%). mp 154.5–155.3° C. MS (APCI): 455 $[M+H]^+$. $^1$H-NMR (dmso-$d_6$, δ): 2.63 (dd, J=9.04, 6.84 Hz, 2H) 2.68 (m, 4H) 2.81 (m, 2H) 3.43 (s, 1H) 3.44 (d, J=6.35 Hz, 3H) 5.01 (s, 2H) 7.06 (d, J=7.57 Hz, 1H) 7.33 (t, J=7.82 Hz, 1H) 7.41 (t, J=8.06 Hz, 1H) 7.52 (d, J=8.06 Hz, 2H) 7.64 (s, 2H) 7.76 (m, 3H) 8.03 (d, J=8.06 Hz, 2H).

EXAMPLE 529

2-{2-[2-(4-BENZO[D]ISOTHIAZOL-3-YL-PIPERAZIN-1-YL)-ETHYL]-PHENYL}-2,3-DIHYDRO-ISOINDOL-1-ONE

2-{2-[2-(4-Benzo[d]isothiazol-3-yl-piperazin-1-yl)-ethyl]-phenyl}-2,3-dihydro-isoindol-1-one was prepared according to the general method as outlined in Example 527 starting from 2-[2-(4-Benzo[d]isothiazol-3-yl-piperazin-1-yl)-ethyl]-phenylamine, yield=192 mg (42.3%). mp 207.6–208° C. MS (APCI): 455 $[M+H]^+$.

EXAMPLE 530

2-{4-[2-(4-BENZO[D]ISOTHIAZOL-3-YL-PIPERAZIN-1-YL)-ETHOXY]-PHENYL}-2,3-DIHYDRO-ISOINDOL-1-ONE

2-{4-[2-(4-Benzo[d]isothiazol-3-yl-piperazin-1-yl)-ethoxy]-phenyl}-2,3-dihydro-isoindol-1-one was prepared according to the general method as outlined in example 527 starting from 4-[2-(4-Benzo[d]isothiazol-3-yl-piperazin-1-yl)-ethoxy]-phenylamine, yield=222 mg (47.2%). mp 166.4–166.6° C. MS (APCI): 471 $[M+H]^+$.

The invention claimed is:

1. A compound of the formula 1

1

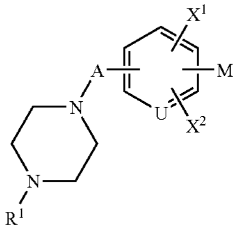

wherein M is (i)

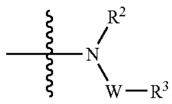

or (ii)

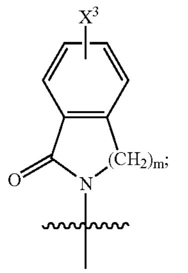

$R^1$ is 1,2-benzisothiazoyl, 1,2-benzisothiazoyl-1-oxide, 1,2-benzisothiazoyl-1-dioxide, or 1,2-benzisoxazolyl, and wherein said $R^1$ can optionally be substituted by one to four substituents, independently selected from halo, cyano, nitro, $(C_1–C_6)$alkyl optionally substituted with from one to three fluorine atoms and $(C_1–C_6)$ alkoxy optionally substituted with from one to three fluorine atoms, and wherein the point of attachment of $R^1$ to the piperazine nitrogen of formula 1 is a carbon atom of the heterocyclic ring of $R^1$;

A is $—(CH_2)_nCH_2—$, wherein n is an integer from one to three;

U is carbon or nitrogen;

m is 1 or 2;

each of $X^1$, $X^2$ and $X^3$ is, independently, hydrogen, halo, $(C_1–C_6)$alkyl optionally substituted with from one to three fluorine atoms and $(C_1–C_6)$alkoxy optionally substituted with from one to three fluorine atoms;

$R^2$ is hydrogen, $(C_1–C_6)$alkyl, aryl$(C_1–C_6)$alkyl, $(C_1–C_6)$ alkenyl, heteroaryl, or heteroaryl$(C_1–C_6)$alkyl, and where the aryl and heteroaryl moieties of the foregoing $R^2$ groups may be optionally substituted with one or two substituents independently selected from halo, $(C_1–C_6)$alkyl optionally substituted with from one to three fluorine atoms and $(C_1–C_6)$alkoxy optionally substituted with from one to three fluorine atoms;

W is —C(O)—, —C(O)O—, —C(O)NH—, $—S(O)_2—$, or $—S(O_2)N(R^4)—$, wherein the hyphen ("-") to the left of each of the foregoing moieties represents the bond to $NR^2$ in structural formula 1, and the hyphen ("-") to the right of each of the foregoing moieties represents the bond to $R^3$ in structural formula 1; and $R^3$ is selected, independently, from $(C_1–C_6)$alkyl, aryl $(C_1–C_6)$alkyl, heteroaryl, and heteroaryl$(C_1–C_6)$alkyl, wherein the aryl and heteroaryl moieties of the foregoing $R^3$ and $R^4$ groups can be optionally be substituted with one or two substituents independently selected from halo, $(C_1–C_6)$alkyl optionally substituted with from one to three fluorine atoms and $(C_1–C_6)$alkoxy optionally substituted with from one to three fluorine atoms;

$R^4$ is selected, independently, from $(C_1–C_6)$alkyl, aryl $(C_1–C_6)$alkyl, $(C_1–C_6)$alkenyl, heteroaryl, and heteroaryl$(C_1–C_6)$alkyl, wherein the aryl and heteroaryl moieties of the foregoing $R^3$ and $R^4$ groups can be optionally be substituted with one or two substituents independently selected from halo, $(C_1–C_6)$alkyl optionally substituted with from one to three fluorine atoms and $(C_1–C_6)$alkoxy optionally substituted with from one to three fluorine atoms;

or a pharmaceutically acceptable salt thereof.

2. A compound according to claim 1 wherein $R^1$ is 1,2-benzisothiazolyl.

3. A compound according to claim 1 wherein U is carbon.

4. A compound according to claim 1 wherein U is nitrogen.

5. A compound according to claim 1 wherein A is $CH_2CH_2$.

6. A compound according to claim 1 wherein W is $—S(O)_2N(CH_3)—$.

7. A compound according to claim 1 wherein W is —C(O)— or —C(O)NH—.

8. A compound according to claim 1 wherein $R^2$ is hydrogen, methyl or ethyl.

9. A compound according to claim 1 wherein $X^1$ and $X^2$ is hydrogen.

10. A compound according to claim 1 wherein W is —CO— and $R^3$ is $(C_1–C_3)$alkyl.

11. A compound according to claim 1, that is selected from the following compounds and their pharmaceutically acceptable salts:

N-{2-[2-(4-1,2-Benzisothiazol-3-yl-piperazin-1-yl)-ethyl]-phenyl}-2-(2,5-dimethoxy-phenyl)-acetamide;

N-{4-[2-(4-1,2-Benzisothiazol-3-yl-piperazin-1-yl)-ethyl]-5-chloro-2-methyl-phenyl}-acetamide;

1-{3-[2-(4-1,2-Benzisothiazol-3-yl-piperazin-1-yl)-ethyl]-phenyl}-3-p-tolyl-urea;

1-{2-[2-(4-1,2-Benzisothiazol-3-yl-piperazin-1-yl)-ethyl]-phenyl}-3-o-tolyl-urea;

1-{4-[2-(4-1,2-Benzisothiazol-3-yl-piperazin-1-yl)-ethyl]-phenyl}-3-cyclopentyl-urea;

N-{2-[2-(4-1,2-Benzisothiazol-3-yl-piperazin-1-yl)-ethyl]-phenyl}-2-(3-methoxy-phenyl)-acetamide;

N-{2-[2-(4-1,2-Benzisothiazol-3-yl-piperazin-1-yl)-ethyl]-phenyl}-2-fluoro-benzenesulfonamide;

1,2-Dimethyl-1H-imidazole-4-sulfonic acid {2-[2-(4-1,2-benzisothiazol-3-yl-piperazin-1-yl)-ethyl]-phenyl}-amide;

N-{4-[2-(4-1,2-Benzisothiazol-3-yl-piperazin-1-yl)-ethyl]-phenyl}-benzenesulfonamide;

N-{4-[2-(4-1,2-Benzisothiazol-3-yl-pipe razin-1-yl)-ethyl]-2-methyl-phenyl}-acetamide;

N-{4-[2-(4-1,2-Benzisothiazol-3-yl-piperazin-1-yl)-ethyl]-5-chloro-2-methyl-phenyl}-N-methyl-acetamide;

N-{4-[2-(4-1,2-Benzisothiazol-3-yl-piperazin-1-yl)-ethyl]-2,5-dimethyl-phenyl}-acetamide;

N-{4-[2-(4-1,2-Benzisothiazol-3-yl-piperazin-1-yl)-ethyl]-2-methyl-phenyl}-N-methyl-acetamide;

N-{4-[2-(4-1,2-Benzisothiazol-3-yl-piperazin-1-yl)-ethyl]-2-methyl-phenyl}-N-ethyl-acetamide;

N-{4-[3-(4-1,2-Benzisothiazol-3-yl-piperazin-1-yl)-propyl]-phenyl}-2-thiophen-2-yl-acetamide;

N-{2-[2-(4-1,2-Benzisothiazol-3-yl-piperazin-1-yl)-ethyl]-phenyl}-2-benzyloxy-acetamide;

N-{2-[2-(4-1,2-Benzisothiazol-3-yl-piperazin-1-yl)-ethyl]-phenyl}-2-(4-methoxy-phenyl)-acetamide;

N-{4-[2-(4-1,2-Benzisothiazol-3-yl-piperazin-1-yl)-ethyl]-phenyl}-2,5-dimethoxy-benzenesulfonamide;

N-{2-[2-(4-1,2-Benzisothiazol-3-yl-piperazin-1-yl)-ethyl]-phenyl}-2-(4-chloro-phenyl)-acetamide;

N-{2-[2-(4-1,2-Benzisothiazol-3-yl-piperazin-1-yl)-ethyl]-4,5-dimethoxy-phenyl}-2-(4-chloro-phenyl)-acetamide;

1-{3-[2-(4-1,2-Benzisothiazol-3-yl-piperazin-1-yl)-ethyl]-phenyl}-3-benzyl-urea; and N-{2-[2-(4-Benzo[d]isothiazol-3-yl-piperazin-1-yl-ethyl]-6-methyl-pyridin-3-yl}-2-(4-chloro-phenyl)-acetamide.

12. A pharmaceutical composition comprising a compound according to claim 1, or a pharmaceutically acceptable salt thereof, and a pharmaceutically acceptable carrier.

13. A method for treating a disorder or condition selected from schizophrenia and bipolar disorder in a mammal, including a human, comprising administering to a mammal in need of such treatment an amount of a compound according to claim 1, or a pharmaceutically acceptable salt thereof that is effective for treating such disorder or condition.

14. A method according to claim 13, wherein the disorder or condition being treated is schizophrenia.

* * * * *